(12) United States Patent
Noronha et al.

(10) Patent No.: US 8,030,487 B2
(45) Date of Patent: Oct. 4, 2011

(54) 2-AMINO—5-SUBSTITUTED PYRIMIDINE INHIBITORS

(75) Inventors: Glenn Noronha, Fort Worth, TX (US); Jianguo Cao, San Diego, CA (US); Colleen Gritzen, Vista, CA (US); Chi Ching Mak, San Diego, CA (US); Andrew McPherson, San Diego, CA (US); Ved P. Pathak, San Diego, CA (US); Joel Renick, San Diego, CA (US); Richard M. Soll, San Diego, CA (US); Binqi Zeng, San Diego, CA (US); Elena Dneprovskaia, San Diego, CA (US)

(73) Assignee: TargeGen, Inc., San Diego, CA (US)

( * ) Notice: Subject to any disclaimer, the term of this patent is extended or adjusted under 35 U.S.C. 154(b) by 964 days.

(21) Appl. No.: 11/772,572

(22) Filed: Jul. 2, 2007

(65) Prior Publication Data
US 2008/0027070 A1     Jan. 31, 2008

Related U.S. Application Data

(60) Provisional application No. 60/819,170, filed on Jul. 7, 2006.

(51) Int. Cl.
| | |
|---|---|
| C07D 239/42 | (2006.01) |
| C07D 401/12 | (2006.01) |
| C07D 401/14 | (2006.01) |
| C07D 403/12 | (2006.01) |
| C07D 403/14 | (2006.01) |
| A61K 31/505 | (2006.01) |
| A61K 31/506 | (2006.01) |
| A61P 19/02 | (2006.01) |
| A61P 35/00 | (2006.01) |

(52) U.S. Cl. ......... 544/320; 544/330; 514/272; 514/275
(58) Field of Classification Search .................. 544/320, 544/330; 514/272, 275
See application file for complete search history.

(56) References Cited

U.S. PATENT DOCUMENTS

| | | | |
|---|---|---|---|
| 6,378,526 B1 | 4/2002 | Bowman et al. | |
| 7,528,143 B2 * | 5/2009 | Noronha et al. ............ | 514/275 |
| 2003/0134838 A1 | 7/2003 | Bornemann et al. | |
| 2004/0106615 A1 | 6/2004 | Cochran et al. | |
| 2004/0167198 A1 | 8/2004 | Wrasidlo et al. | |
| 2005/0234083 A1 | 10/2005 | Chamberlain et al. | |
| 2005/0239852 A1 | 10/2005 | Ciufolini et al. | |
| 2006/0247250 A1 * | 11/2006 | Cao et al. ................ | 514/252.14 |
| 2006/0292203 A1 * | 12/2006 | Dellamary et al. ......... | 424/427 |
| 2007/0072862 A1 * | 3/2007 | Dimauro et al. ............ | 514/248 |
| 2007/0149508 A1 | 6/2007 | Noronha et al. | |
| 2007/0161615 A1 | 7/2007 | Andrews et al. | |

FOREIGN PATENT DOCUMENTS

| | | |
|---|---|---|
| WO | WO 0046203 A2 * | 8/2000 |
| WO | WO-02/064096 A2 | 8/2002 |
| WO | WO-02/064096 A3 | 8/2002 |
| WO | WO-03/066601 A1 | 8/2003 |
| WO | WO-2006/101977 A2 | 9/2006 |
| WO | WO-2006/101977 A3 | 9/2006 |
| WO | WO-2006/133411 A1 | 12/2006 |
| WO | WO-2007/056023 A2 | 5/2007 |
| WO | WO-2007/056023 A3 | 5/2007 |
| WO | WO-2007/056075 A2 | 5/2007 |
| WO | WO-2007/056075 A3 | 5/2007 |
| WO | WO-2008/008234 A1 | 1/2008 |

OTHER PUBLICATIONS

Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Powell et al., British Journal of Dermatology, 141" 802-810, 1999.*
Golub et al., Science, 286, 531-537, 1999.*
Cecil Textbook of Medicine, edited by Bennet, J.C., and Plum F., 20th edition,vol. 1, 1004-1010, 1996.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
West, Anthony R., Solid State Chemistry and its Applications, Wiley, New York, 1988, pp. 358 & 365.*
Vippagunta et al., Advanced Drug Delivery Reviews 48: 3-26, 2001.*
Krause, D. S. et al. (Jul. 14, 2005). "Tyrosine Kinases as Targets for Cancer Therapy," *N. Eng. J. Med.* 353(2):172-187.
Shah, N. P. et al. (Jul. 16, 2004). "Overriding Imatinib Resistance with a Novel ABL Kinase Inhibitor," *Science* 305:399-401.
International Search Report mailed on Sep. 21, 2006, for PCT Patent Application No. PCT/US06/009518, filed on Mar. 15, 2006, 2 pages.
Written Opinion mailed on Sep. 21, 2006, for PCT Patent Application No. PCT/US06/009518, filed on Mar. 15, 2006, 4 pages.
International Search Report mailed on Sep. 18, 2006, on for PCT Patent Application No. PCT/US06/022480, filed on Jun. 7, 2006, one page.

(Continued)

*Primary Examiner* — Venkataraman Balasubramanian
(74) *Attorney, Agent, or Firm* — Morrison & Foerster LLP

(57) ABSTRACT

Compounds having the general structure (A) are provided. The compounds of the invention are capable of inhibiting kinases, such as members of the Src kinase family, Vegfr and various other specific receptor and non-receptor kinases.

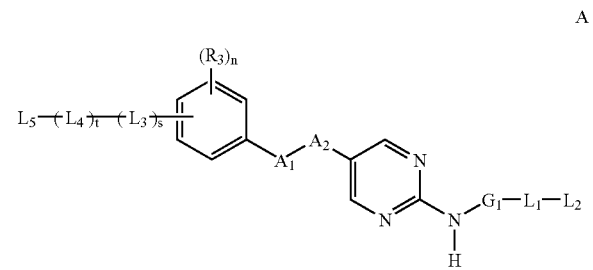

34 Claims, No Drawings

OTHER PUBLICATIONS

Written Opinion mailed on Sep. 18, 2006, for PCT Patent Application No. PCT/US06/022480, filed on Jun. 7, 2006, 3 pages.
International Search Report mailed on Jul. 25, 2007, for PCT Patent Application No. PCT/US06/42838, filed on Oct. 31, 2006, 2 pages.
Written Opinion mailed on Jul. 25, 2007, for PCT Patent Application No. PCT/US06/42838, filed on Oct. 31, 2006, 4 pages.
International Search Report mailed on Jul. 30, 2007, for PCT Patent Application No. PCT/US06/042697, filed Oct. 31, 2006, 2 pages.
Written Opinion mailed on mailed on Jul. 30, 2007, for PCT Patent Application No. PCT/US06/042697, filed Oct. 31, 2006, 4 pages.
International Search Report mailed on Dec. 4, 2007, for PCT Patent Application No. PCT/US07/15357, filed on Jul. 2, 2007, 2 pages.
Written Opinion mailed on Dec. 4, 2007, for PCT Patent Application No. PCT/US07/15357, filed on Jul. 2, 2007, 6 pages.
Non Final Office Action issued on Jan. 12, 2009, for U.S. Appl. No. 11/377,234, filed Mar. 15, 2006, 6 pages.
Non Final Office Action issued on Jul. 23, 2008, for U.S. Appl. No. 11/377,234, filed Mar. 15, 2006, 23 pages.
Non Final Office Action issued Dec. 22, 2008, for U.S. Appl. No. 11/591,252 filed Oct. 31, 2006, 20 pages.
Non Final Office Action issued Jun. 23, 2008, for U.S. Appl. No. 11/591,252 filed Oct. 31, 2006, 21 pages.

* cited by examiner

2-AMINO—5-SUBSTITUTED PYRIMIDINE INHIBITORS

CROSS-REFERENCE TO RELATED APPLICATIONS

This application claims priority under 35 U.S.C. §119(e) to U.S. Patent Application Ser. No. 60/819,170 filed Jul. 7, 2006, which is herein incorporated by reference in its entirety.

FIELD OF THE INVENTION

The present invention relates generally to the use of pyrimidine-based compounds to treat a variety of disorders, diseases and pathologic conditions, and, more specifically, to the use of 2-amino-5-substituted pyrimidine inhibitors of kinases to treat various disorders.

BACKGROUND

Protein kinases are families of enzymes that catalyze the phosphorylation of specific residues in proteins, and may be broadly classified into tyrosine or serine/threonine kinases based on the amino acids phosphorylated. This covalent post-translational modification is a pivotal component of normal cellular communication and maintenance of homeostasis. Tyrosine kinase signaling pathways normally prevent deregulated proliferation or contribute to sensitivity towards apoptotic stimuli. These signaling pathways are often genetically or epigenetically altered in cancer cells to impart a selection advantage to the cancer cells. Understandably therefore, aberrant enhanced signaling emanating from tyrosine kinase endows these enzymes a dominating oncoprotein status, resulting in the malfunctioning of the signaling network. Inappropriate kinase activity arising from mutation, over-expression, or inappropriate regulation, dys-regulation, mis-regulation or de-regulation, as well as over- or under-production of growth factors or cytokines has been implicated in many diseases, including but not limited too cancer, cardiovascular diseases, allergies, asthma and other respiratory diseases, autoimmune diseases, inflammatory diseases, bone diseases, metabolic disorders, and neurological and neurodegenerative disorders such as Alzheimer's disease, and to various blinding ocular diseases.

Transmembrane receptor protein kinases exhibit an extracellular domain, capable of ligand binding. These ligand binding mechanisms trigger activation of the kinase catalytic domain which initiates a cascade of signals that controls intracellular functions. Examples of receptor protein kinase are growth factors such as EGF, FGF, VEGF, PDGF and IGF. Nonreceptor protein kinases can be found in many compartments of a cell from inner-cell surface membranes to the cell nucleus.

Several families of tyrosine kinases can function in each of the responses to various stimuli and pathways, and biological cellular responses relating to cell growth, cell differentiation, survival, apoptosis, mitogenesis, cell cycle control, and cell mobility. Additional complexity results from extensive cross-talk between different receptor kinase pathways. One family of cytoplasmic tyrosine kinases capable of communicating with a large number of different receptors is the Src protein tyrosine kinase family. The c-Src proto-oncogene can play a role in the development, growth, progression, and metastasis of a wide variety of human cancers. Src over-activation, in the form of elevated kinase activity and protein expression levels, has been demonstrated in several major cancer types, including colon, breast, pancreatic, lung, and brain carcinomas. Src kinase modulates signal transduction through multiple oncogenic pathways, including EGFR, Her2/neu, PDGFR, FGFR, and VEGFR. There are structural and functional interactions between the Src family kinases and cellular receptors, and from Src family kinases on receptor-induced biological activities regulated by these kinases.

There is a body of evidence linking kinase mis-regulation, dysregulation and mutation to a variety of oncological indications. Kinases have been implicated in ocular diseases, not limited to, but including age related macular degeneration, diabetic macular edema and proliferative diabetic retinopathy.

Biochemically, cellular stimuli that lead to Src activation result in increased association between Src and the cytoskeleton. As a result, Src mediates the phosphorylation of many intracellular substrates such as EGFR, FAK, PYK2, paxillin, Stat3, and cyclin D. The biological effects of these interactions affect cell motility, adhesion, cell cycle progression, and apoptosis and might have some connection to the disease related effects stated above. Thus, Src plays a role in responses to regional hypoxia, limited nutrients, and internal cellular effects to self-destruct.

Increased c-Src TK activity results in breakdown of the E-cadherin-mediated epithelial cell-cell adhesion, which can be restored by Src inhibition. Intimate connections between increased VEGF activity, Src activity, and cellular barrier function related to vascular leak have been also demonstrated. Inhibition of Src results in decrease in vascular leak when exogenous VEGF is administered in in vivo studies. Examples where excessive vascular permeability leads to particularly deleterious effects include pulmonary edema, cerebral edema, and cardiac edema.

Since the activation and perhaps over-expression of Src has been implicated in cancer, osteoporosis, stroke, myocardial infarction, and vascular leak, among others, a small molecule inhibitor of c-Src can be beneficial for the treatment of several disease states. VEGFR inhibition has been shown to be validated for disease states involving angiogenesis, various cancers and in back of the eye diseases as exemplified by acute macular degeneration (AMD), diabetic macular edema (DME) and proliferative diabetic retinopathy (PDR), all blinding eye diseases that afflicts large numbers of people. Dual Src and VEGFR inhibitors thus have the potential for multiple utility in several different disease states.

SUMMARY

The present invention provides methods of use for certain chemical compounds such as kinase inhibitors for treatment of various diseases, disorders, and pathologies, for example, cancer, and vascular disorders, such as myocardial infarction (MI), stroke, or ischemia, and in ocular diseases and disorders such as acute macular degeneration, diabetic retinopathy, diabetic macular edema, cancer, and glaucoma. In addition, the compounds described of this invention may be beneficial for treatment of the diseases where disorders affect cell motility, adhesion, and cell cycle progression, and in addition, diseases with related hypoxic conditions, osteoporosis and conditions which result from, or are related to, increases in vascular permeability, inflammation or respiratory distress, tumor growth, invasion, angiogenesis, metastases and apoptosis.

According to embodiments of the invention, examples of some kinase inhibitors that can be used to bring about beneficial therapeutic results include inhibitors of Src kinase, and Vegfr kinase.

According to one embodiment of the invention, compounds having structure (A) are provided:

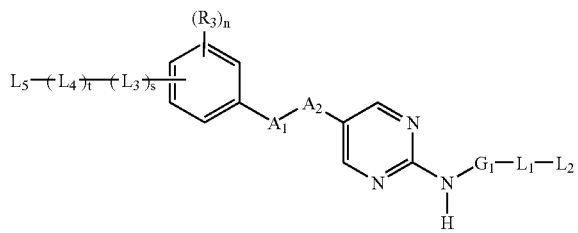

A

In the compounds of the structure (A), $L_1$ is any of O, SO, $SO_2$, $SO_2$-alkyl, $SO_2NH$, CO, C(O)NH, $SO_2NH$-alkyl, CO-alkyl, C(O)NH-alkyl, OC(O), C(O)O, optionally substituted alkyl, branched alkyl, aminoalkyl, alkoxy, or hydroxyalkyl;

$L_2$ is any of H, optionally substituted alkyl, branched alkyl, aminoalkyl, hydroxyalkyl, cycloalkyl, or heterocycle; or when $G_1$ is heteroaryl or H, $L_1$ or $L_2$ or both $L_1$ and $L_2$ can be absent;

$A_1$ is any of a bond, $NR_a$, C(O), S(O), $S(O)_2$, $P(O)_2$, O, S, and $C(R_a)_2$, wherein if $A_1$ is a bond, then the phenyl ring is directly connected to the group $A_2$;

$A_2$ is any of $NR_a$, C(O), S(O), $S(O)_2$, $P(O)_2$, O, and S; and the connectivity between the phenyl ring, $A_1$, $A_2$ and the pyrimidine ring are chemically correct;

$R_a$ is any of H, lower alkyl, branched alkyl, hydroxyalkyl, aminoalkyl, thioalkyl, alkylhydroxyl, alklythiol, and alkylamino;

$R_3$, for each occurrence, is any of hydrogen, alkyl, branched alkyl, alkoxy, halogen, $CF_3$, cyano, substituted alkyl, hydroxyl, alklylhydroxyl, thiol, alkylthiol, thioalkyl, amino, and aminoalkyl;

n is an integer having value between 0 and 4 inclusive;

$L_3$ and $L_4$ are each, independently, any of NH, $NR_a$, $NHCH_2$, $NHCHR_a$, $NHC(R_a)_2$, N(O), C(O), S(O), $S(O)_2$, $OS(O)_2$, O, $CH_2$, $CHR_a$, $(CR_a)_2$, P(O), OP, OP(O), $OP(O)_2$, P(O)NH, $P(O)NR_a$, $P(O)_2NH$, C(O)NH, C(O) $NR_a$, NHC(O), $NR_aC(O)$, NHS(O), $NR_aS(O)$, $NHS(O)_2$, $NR_aS(O)_2$, NHP(O), and $NR_aP(O)_2$;

each of s and t is an integer independently having the value of 0 or 1, with the proviso that if s=0, then t=1, and if t=0, then s=1; and $L_5$ is any of lower alkyl, branched alkyl, $CF_3$, cycloalkyl, optionally substituted aryl, optionally substituted heteroaryl, bicyclic aryl, bicyclic heteroaryl, bicyclic with one of the rings being aryl or heteroaryl and the other ring being non-aryl, and bicyclic with both rings being nonaryl; and wherein an optionally substituted aryl or heteroaryl, independently for each occurrence, can be substituted on 1, 2, 3, or 4 carbons by alkyl, branched alkyl, alkoxy, halogen, $CF_3$, cyano, substituted alkyl, hydroxyl, thiol, alkylthiol, thioalkyl, amino, and aminoalkyl.

In another embodiment, there are provided pharmaceutical compositions including at least one compound of structure (A) and a pharmaceutically acceptable carrier therefore.

In yet another embodiment, there are provided articles of manufacture including packaging material and a pharmaceutical composition contained within the packaging material, wherein the packaging material includes a label which indicates that the pharmaceutical composition can be used for treatment of disorders associated with compromised vasculostasis and wherein the pharmaceutical composition includes at least one compound of structure (A).

In another embodiment, there are provided articles of manufacture including packaging material and a pharmaceutical composition contained within the packaging material, wherein the packaging material includes a label which indicates that the pharmaceutical composition can be used for treatment of disorders associated with vascular permeability leakage or compromised vasculostasis selected from myocardial infarction, stroke, congestive heart failure, an ischemia or reperfusion injury, cancer, arthritis or other arthropathy, retinopathy or vitreoretinal disease, macular degeneration, autoimmune disease, vascular leakage syndrome, inflammatory disease, edema, transplant rejection, burn, or acute or adult respiratory distress syndrome (ARDS) and wherein the pharmaceutical composition includes at least one compound of structure (A).

In another embodiment, there are provided methods of treating a disorder associated with compromised vasculostasis, including the administration of a therapeutically effective amount of at least one compound of structure 1 or pharmaceutically acceptable salts, hydrates, solvates, crystal forms and individual diastereomers thereof, to a subject in need of such treatment.

In yet another embodiment, there are provided methods of treating a disorder associated with compromised vasculostasis including the administration of a therapeutically effective amount of at least one compound of structure (A), or pharmaceutically acceptable salts, hydrates, solvates, crystal forms and individual diastereomers thereof, in combination with an anti-inflammatory, chemotherapeutic agent, immunomodulatory agent, therapeutic antibody or a protein kinase inhibitor, to a subject in need of such treatment.

In another embodiment, there are provided methods of treating a subject having or at risk of having myocardial infarction including administering to the subject a therapeutically effective amount of at least one compound of structure (A), thereby treating the subject.

In another embodiment, there are provided methods of treating a subject having or at risk of having vascular leakage syndrome (VLS) including administering to the subject a therapeutically effective amount of at least one compound of structure (A), thereby treating the subject.

In another embodiment, there are provided methods of treating a subject having or at risk of having cancer including administering to the subject a therapeutically effective amount of at least one compound of structure (A), thereby treating the subject.

In another embodiment, there are provided methods of treating a subject having or at risk of having stroke including administering to the subject a therapeutically effective amount of at least one compound of structure (A), thereby treating the subject.

In another embodiment, there are provided methods of treating a subject having or at risk of having ARDS including administering to the subject a therapeutically effective amount of at least one compound of structure (A), thereby treating the subject.

In another embodiment, there are provided methods of treating a subject having or at risk of having burns including administering to the subject a therapeutically effective amount of at least one compound of structure (A), thereby treating the subject.

In another embodiment, there are provided methods of treating a subject having or at risk of having arthritis including administering to the subject a therapeutically effective amount of at least one compound of structure (A), thereby treating the subject.

In another embodiment, there are provided methods of treating a subject having or at risk of having edema including administering to the subject a therapeutically effective amount of at least one compound of structure (A), thereby treating the subject.

In another embodiment, there are provided methods of treating a subject having or at risk of having vascular leakage syndrome (VLS) including administering to the subject a therapeutically effective amount of at least one compound of structure (A), thereby treating the subject.

In another embodiment, there are provided methods of treating a subject having or at risk of having retinopathy or vitreoretinal disease including administering to the subject a therapeutically effective amount of at least one compound of structure (A), thereby treating the subject.

In another embodiment, there are provided methods of treating a subject having or at risk of having ischemic or reperfusion related tissue injury or damage, including administering to the subject a therapeutically effective amount of at least one compound of structure (A), thereby treating the subject.

In another embodiment, there are provided methods of treating a subject having or at risk of having an autoimmune disease, including administering to the subject a therapeutically effective amount of at least one compound of structure (A), thereby treating the subject.

In another embodiment, there are provided methods of treating a subject having or at risk of having transplant rejection, including administering to the subject a therapeutically effective amount of at least one compound of structure (A), thereby treating the subject.

In another embodiment, there are provided methods of treating a subject having or at risk of having inflammatory disease, including administering to the subject a therapeutically effective amount of at least one compound of structure (A), thereby treating the subject.

In another embodiment, there are provided processes for making a pharmaceutical composition including combining a combination of at least one compound of structure (A) or its pharmaceutically acceptable salts, hydrates, solvates, crystal forms salts and individual diastereomers thereof and a pharmaceutically acceptable carrier.

DETAILED DESCRIPTION

The following terminology and definitions apply as used in the present application, generally in conformity with the terminology recommended by the International Union of Pure and Applied Chemistry (IUPAC):

The term "heteroatom" refers to any atom other than carbon, for example, N, O, or S.

The term "aromatic" refers to a cyclically conjugated molecular entity with stability, due to delocalization, significantly greater than that of a hypothetical localized structure, such as the Kekule structure.

The term "heterocyclic," when used to describe an aromatic ring, refers to the aromatic rings containing at least one heteroatom, as defined above.

The term "heterocyclic," when not used to describe an aromatic ring, refers to cyclic (i.e., ring-containing) groups other than aromatic groups, the cyclic group being formed by between 3 and about 14 carbon atoms and at least one heteroatom described above.

The term "substituted heterocyclic" refers, for both aromatic and non-aromatic structures, to heterocyclic groups further bearing one or more substitutents described below.

The term "alkyl" refers to a monovalent straight or branched chain hydrocarbon group having from one to about 12 carbon atoms, for example, methyl, ethyl, n-propyl, iso-propyl, n-butyl, iso-butyl, tert-butyl, n-pentyl (also known as n-amyl), n-hexyl, and the like. The term "lower alkyl" refers to alkyl groups having from 1 to about 6 carbon atoms.

The term "substituted alkyl" refers to alkyl groups further bearing one or more substitutents such as hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, aldehyde, acyl, oxyacyl, carboxyl, sulfonyl, sulfonamide, sulfuryl, and the like.

The term "alkenyl" refers to straight-chained or branched hydrocarbyl groups having at least one carbon-carbon double bond, and having between about 2 and about 12 carbon atoms, and the term "substituted alkenyl" refers to alkenyl groups further bearing one or more substitutents described above.

The term "alkynyl" refers to straight-chained or branched hydrocarbyl groups having at least one carbon-carbon triple bond, and having between about 2 and about 12 carbon atoms, and the term "substituted alkynyl" refers to alkynyl groups further bearing one or more substitutents described above.

The term "aryl" refers to aromatic groups having between about 5 and about 14 carbon atoms and the term "substituted aryl" refers to aryl groups further bearing one or more substitutents described above.

The term "heteroaryl" refers to aromatic rings, where the ring structure is formed by between 3 and about 14 carbon atoms and by at least one heteroatom described above, and the term "substituted heteroaryl" refers to heteroaryl groups further bearing one or more substitutents described above.

The term "alkoxy" refers to the moiety —O-alkyl, wherein alkyl is as defined above, and the term "substituted alkoxy" refers to alkoxy groups further bearing one or more substitutents described above.

The term "cycloalkyl" refers to alkyl groups having between 3 and about 8 carbon atoms arranged as a ring, and the term "substituted cycloalkyl" refers to cycloalkyl groups further bearing one or more substitutents described above.

The term "alkylaryl" refers to alkyl-substituted aryl groups and the term "substituted alkylaryl" refers to alkylaryl groups further bearing one or more substitutents described above.

The term "arylalkyl" refers to aryl-substituted alkyl groups and the term "substituted arylalkyl" refers to arylalkyl groups further bearing one or more substitutents described above.

The term "arylalkenyl" refers to aryl-substituted alkenyl groups and the term "substituted arylalkenyl" refers to arylalkenyl groups further bearing one or more substitutents described above.

The term "arylalkynyl" refers to aryl-substituted alkynyl groups and the term "substituted arylalkynyl" refers to arylalkynyl groups further bearing one or more substitutents described above.

The term "arylene" refers to divalent aromatic groups having between 5 and about 14 carbon atoms and the term "substituted arylene" refers to arylene groups further bearing one or more substitutents described above.

The term "kinase" refers to any enzyme that catalyzes the addition of phosphate groups to a protein residue; for example, serine and threonine kinases catalyze the addition of phosphate groups to serine and threonine residues.

The terms "Src kinase," "Src kinase family," and "Src family" refer to the related homologs or analogs belonging to the mammalian family of Src kinases, including, for example, c-Src, Fyn, Yes and Lyn kinases and the hematopoietic-restricted kinases Hck, Fgr, Lck and Blk.

The terms "Src kinase signaling pathway," and "Src cascade" refer to both the upstream and downstream components of the Src signaling cascade.

The terms "VEGFR kinase," "VEGFR," refer to any of the vacular endothelial growth factor receptors.

The terms "VEGF signaling," and "VEGF cascade" refer to both the upstream and downstream components of the VEGF signaling cascade.

The term "therapeutically effective amount" refers to the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

The term "pharmaceutically acceptable" refers to the fact that the carrier, diluent or excipient must be compatible with the other ingredients of the formulation and not deleterious to the recipient thereof.

The terms "administration of a compound" or "administering a compound" refer to the act of providing a compound of the invention or pharmaceutical composition to the subject in need of treatment.

The term "antibody" refers to intact molecules of polyclonal or monoclonal antibodies, as well as fragments thereof, such as Fab and $F(ab')_2$, Fv and SCA fragments which are capable of binding an epitopic determinant.

The term "vasculostasis" refers to the maintenance of the homeostatic vascular functioning leading to the normal physiologic functioning.

The term "vasculostatic agents" refers to agents that seek to address conditions in which vasculostasis is compromised by preventing the loss of or restoring or maintaining vasculostasis.

According to an embodiment of the invention, compounds having the structure (A) are provided for treatment of various diseases, disorders, and pathologies:

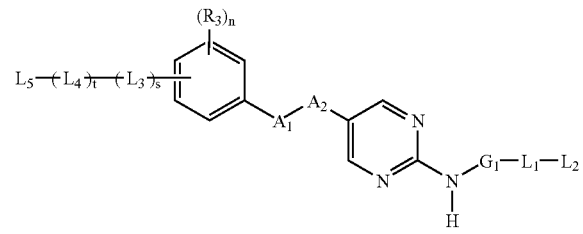

A

In the compounds of the structure (A), $L_1$ is any of O, SO, $SO_2$, $SO_2$-alkyl, $SO_2NH$, CO, C(O)NH, $SO_2NH$-alkyl, CO-alkyl, C(O)NH-alkyl, OC(O), C(O)O, optionally substituted alkyl, branched alkyl, aminoalkyl, alkoxy, or hydroxyalkyl;

$L_2$ is any of H, optionally substituted alkyl, branched alkyl, aminoalkyl, hydroxyalkyl, cycloalkyl, or heterocycle; or when $G_1$ is heteroaryl or H, $L_1$ or $L_2$ or both $L_1$ and $L_2$ can be absent;

$A_1$ is any of a bond, $NR_a$, C(O), S(O), $S(O)_2$, $P(O)_2$, O, S, and $C(R_a)_2$, wherein if $A_1$ is a bond, then the phenyl ring is directly connected to the group $A_2$;

$A_2$ is any of $NR_a$, C(O), S(O), $S(O)_2$, $P(O)_2$, O, and S; and the connectivity between the phenyl ring, $A_1$, $A_2$ and the pyrimidine ring are chemically correct;

$R_a$ is any of H, lower alkyl, branched alkyl, hydroxyalkyl, aminoalkyl, thioalkyl, alkylhydroxyl, alklythiol, and alkylamino;

$R_3$, for each occurrence, is any of hydrogen, alkyl, branched alkyl, alkoxy, halogen, $CF_3$, cyano, substituted alkyl, hydroxyl, alklylhydroxyl, thiol, alkylthiol, thioalkyl, amino, and aminoalkyl;

n is an integer having value between 0 and 4 inclusive;

$L_3$ and $L_4$ are each, independently, any of NH, $NR_a$, $NHCH_2$, $NHCHR_a$, $NHC(R_a)_2$, N(O), C(O), S(O), $S(O)_2$, $OS(O)_2$, O, $CH_2$, $CHR_a$, $(CR_a)_2$, P(O), OP, OP(O), $OP(O)_2$, P(O)NH, $P(O)NR_a$, $P(O)_2NH$, C(O)NH, C(O) $NR_a$, NHC(O), $NR_aC(O)$, NHS(O), $NR_aS(O)$, $NHS(O)_2$, $NR_aS(O)_2$, NHP(O), and $NR_aP(O)_2$;

each of s and t is an integer independently having the value of 0 or 1, with the proviso that if s=0, then t=1, and if t=0, then s=1; and $L_5$ is any of lower alkyl, branched alkyl, $CF_3$, cycloalkyl, optionally substituted aryl, optionally substituted heteroaryl, bicyclic aryl, bicyclic heteroaryl, bicyclic with one of the rings being aryl or heteroaryl and the other ring being nonaryl, and bicyclic with both rings being nonaryl; and wherein an optionally substituted aryl or heteroaryl, independently for each occurrence, can be substituted on 1, 2, 3, or 4 carbons by alkyl, branched alkyl, alkoxy, halogen, $CF_3$, cyano, substituted alkyl, hydroxyl, thiol, alkylthiol, thioalkyl, amino, and aminoalkyl.

In some embodiments, the compounds are provided having the general structure

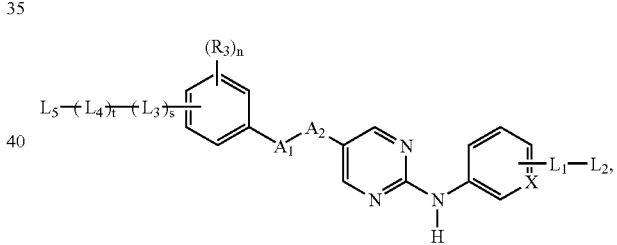

wherein X is selected from a group consisting of CH and N, and all of $L_1$, $L_2$, $L_3$, $L_4$, $L_5$, $R_3$, $A_1$, $A_2$, t, s, and n are as defined above.

In some other embodiments, the compounds are provided having the general structure

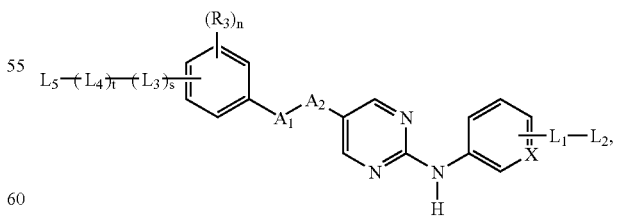

wherein each of $A_1$ and $A_2$ is independently selected from a group consisting of C=O and NH, with the further proviso that when $A_1$ is NH, $A_2$ is C=O, and when $A_2$ is NH, $A_1$ is C=O, and all of X, $L_1$, $L_2$, $L_3$, $L_4$, $L_5$, $R_3$, t, s, and n are as defined above.

In some embodiments, the compounds are provided having the general structure

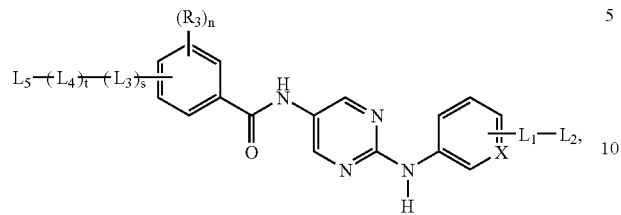

wherein all of X, $L_1$, $L_2$, $L_3$, $L_4$, $L_5$, $R_3$, t, s, and n are as defined above.

In some embodiments, in the structures provided above, $L_5$ is an optionally substituted aryl or an optionally substituted heteroaryl. In some embodiments, in the structures provided above, the moiety $$-(L_4)_t-(L_3)_s-$$

is any of

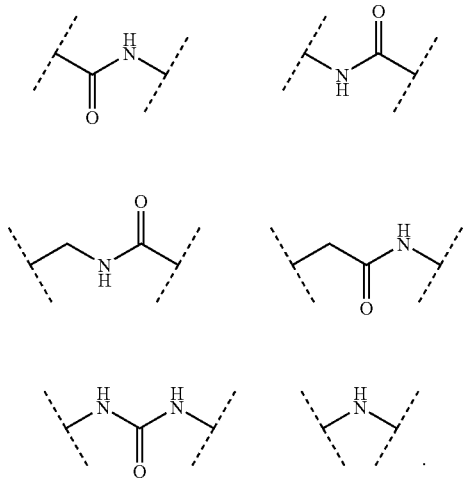

In some embodiments, the compounds are provided having the general structure

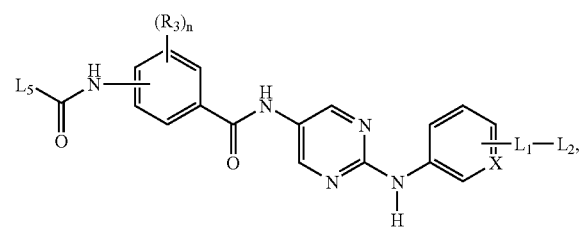

wherein $L_5$ is any of an optionally substituted aryl or an optionally substituted heteroaryl, and all of X, $L_1$, $L_2$, $R_3$ and n are as defined above.

In some embodiments, in the structures provided above, the moiety L1-L2 is any of:

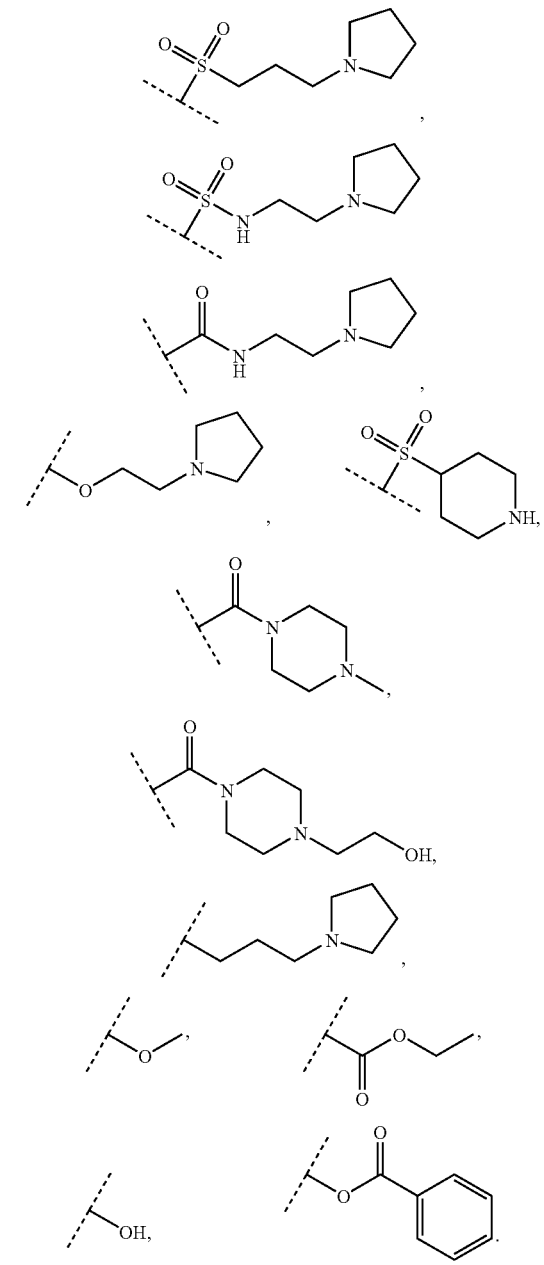

In some embodiments, the compounds are provided having the general structure

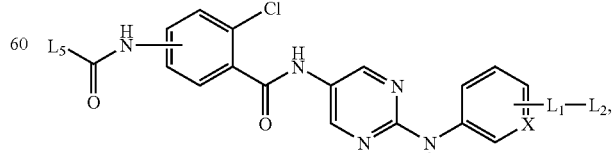

wherein L₅ is a phenyl optionally substituted on 1, 2, 3, 4, or 5 carbons with halogen, alkyl, or CF₃; X is N or CH; and the moiety L1-L2 is any of SO₂-alkyl-heterocycle, —SO₂NH-alkyl-heterocycle; SO₂-heterocycle, —O-alkyl-heterocycle; —C(O)N-alkyl-heterocycle, —C(O)-alkyl-heterocycle, -alkyl-heterocycle; —O-alkyl; —C(O)O-alkyl; —OH; —OC(O)-phenyl; wherein the heterocycle or the phenyl can be optionally substituted with alkyl, alkyloxy, hydroxyalkyl, or halogen; and pharmaceutically acceptable salts, hydrates, solvates, prodrugs, stereoisomers, N-oxides or crystal forms thereof, and in some embodiments, the optionally substituted heterocycle is selected from a group consisting of azetadine, pyrrolidine, morpholine, piperidine, piperazine, azepane, diazepane, and azocane.

In some embodiments, the compounds are provided having the general structure

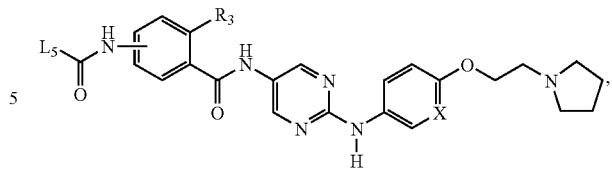

wherein L₅ is phenyl, optionally substituted with methyl, halogen, or CF₃; R₃ is any of methyl and chloro, and X is any of CH and N, and pharmaceutically acceptable salts, hydrates, solvates, prodrugs, stereoisomers, N-oxides or crystal forms thereof.

Some non-limiting examples of specific compounds described by structure A that can be used include compounds I through LXIII shown below:

I

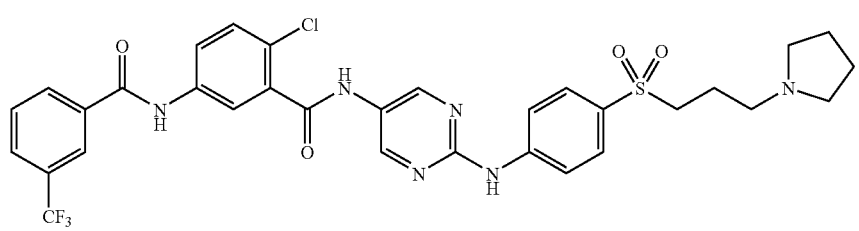

II

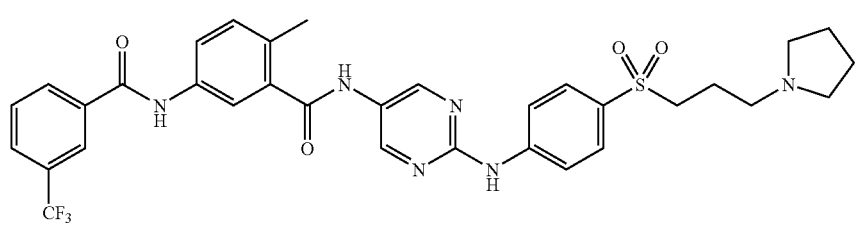

III

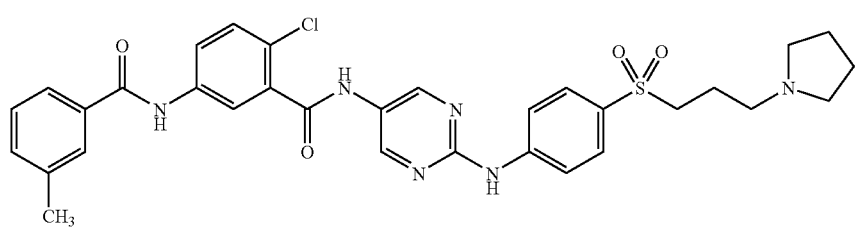

IV

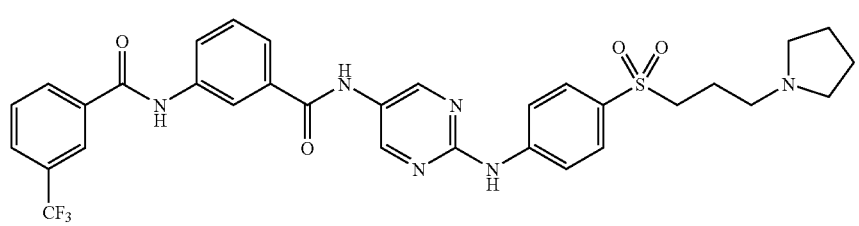

V

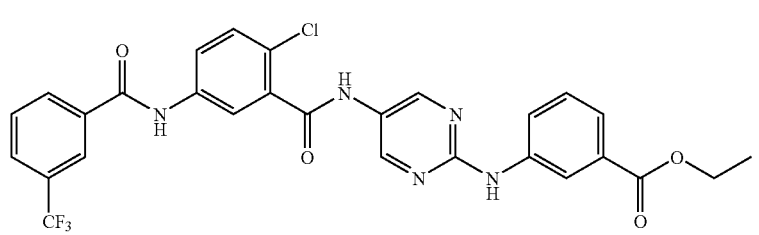

-continued
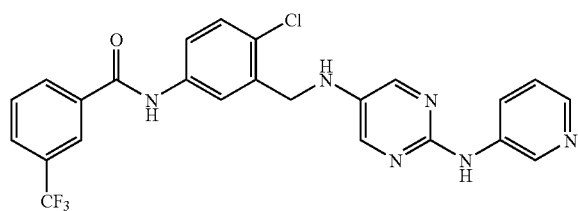
VI
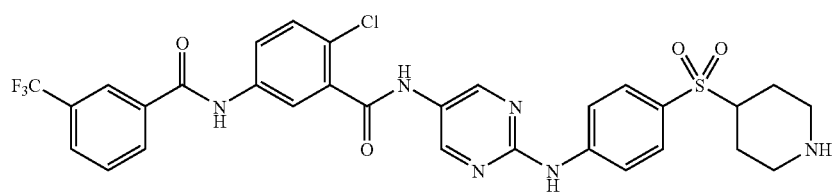
VII
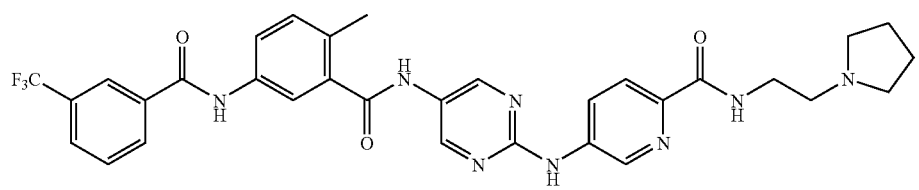
VIII
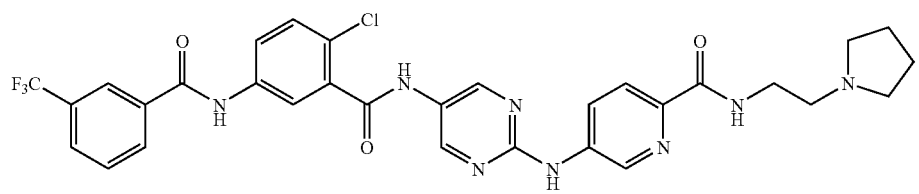
IX
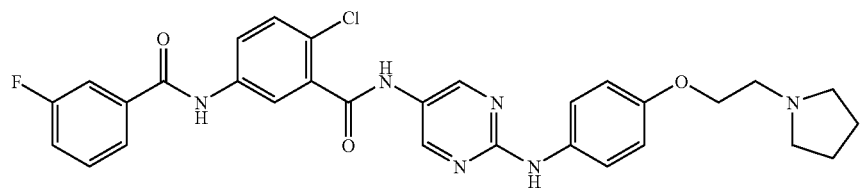
X
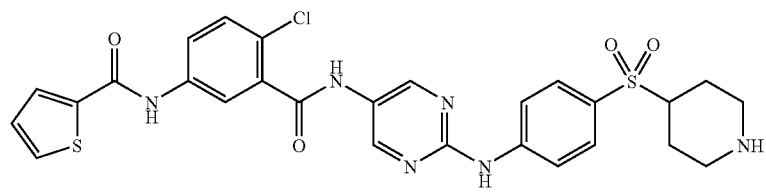
XI
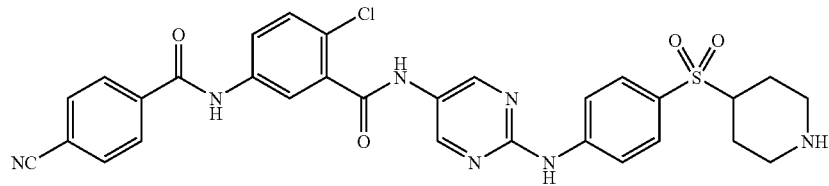
XII
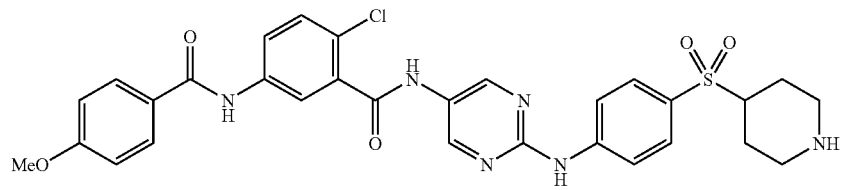
XIII -continued
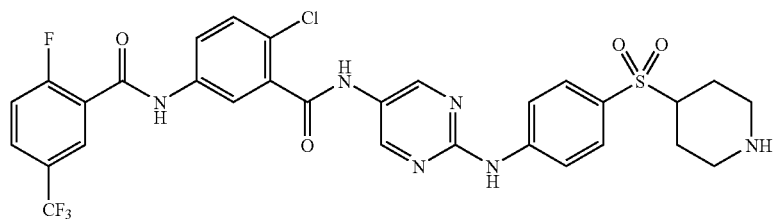 XIV
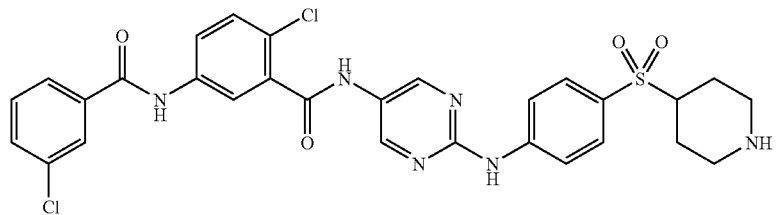 XV
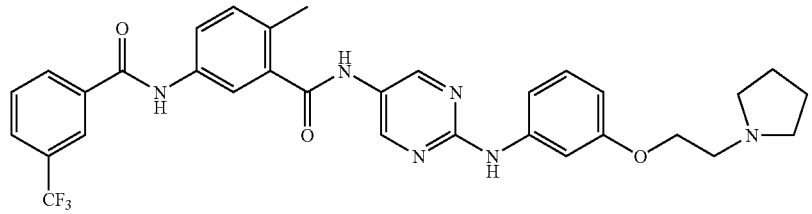 XVI
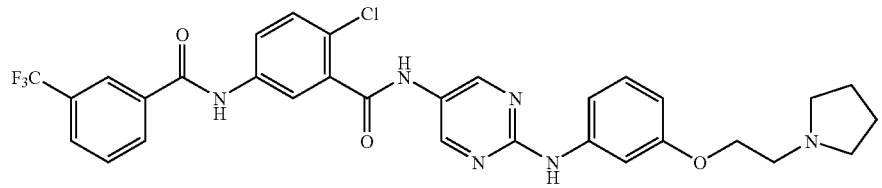 XVII
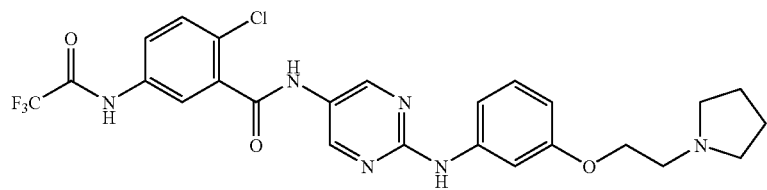 XVIII
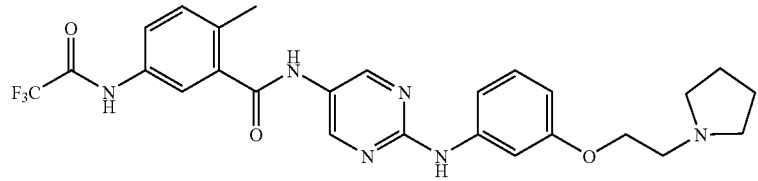 XIX
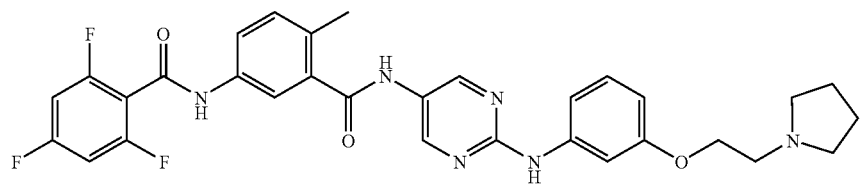 XX -continued
XXI
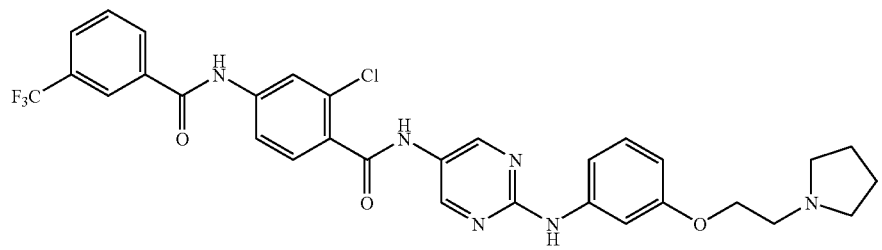
XXII
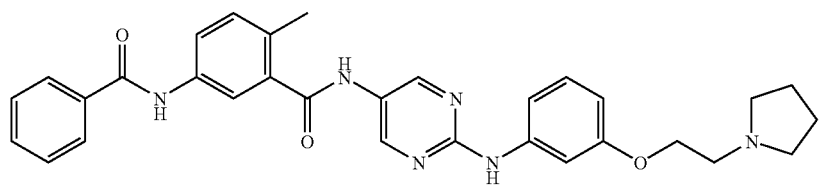
XXIII
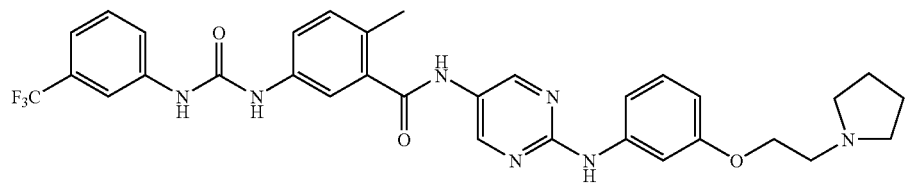
XXIV
XXV
XXVI
XXVII
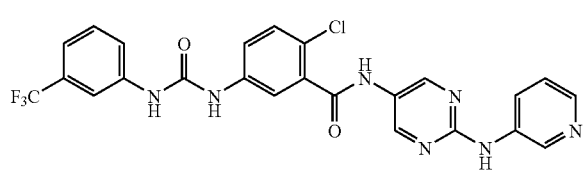
XXVIII
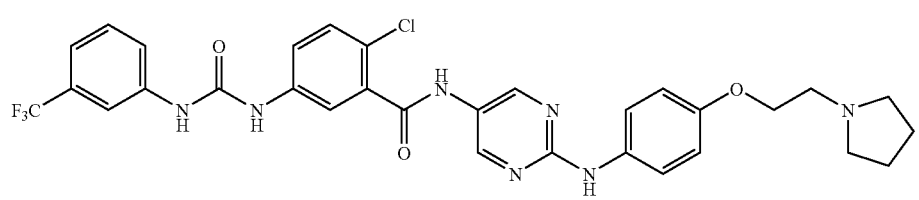
XXIX
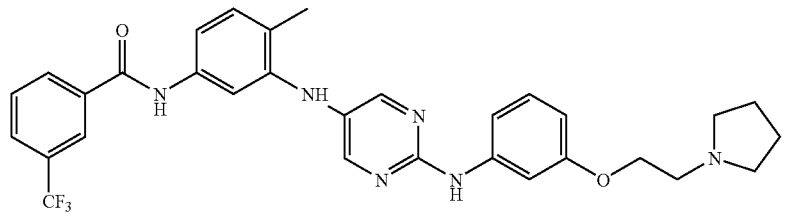

XXX
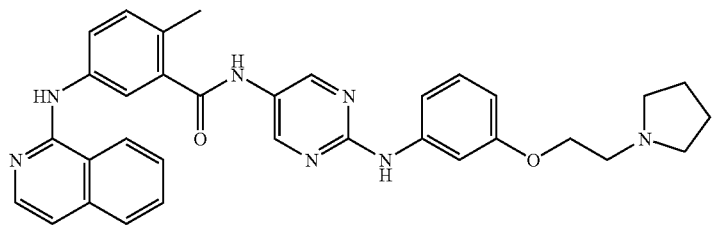
XXXI
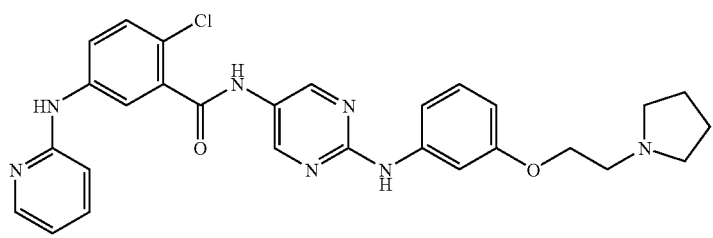
XXXII
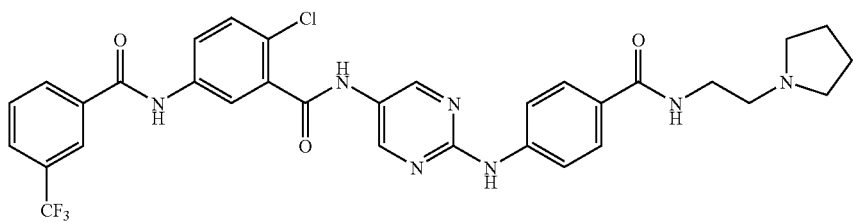
XXXIII
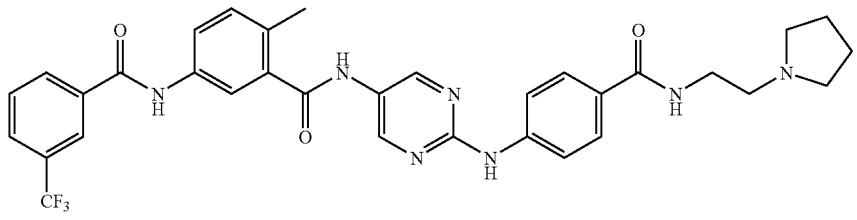
XXXIV
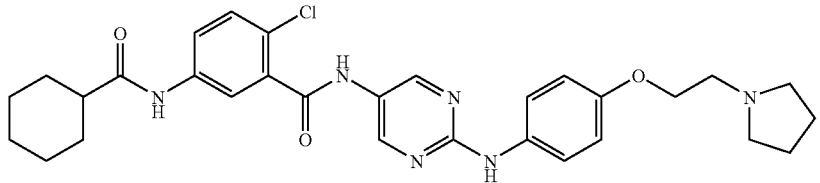
XXXV
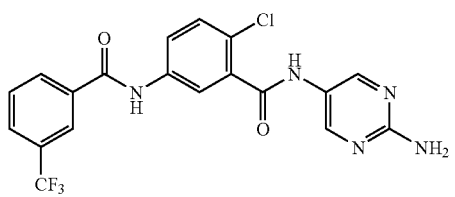
XXXVI
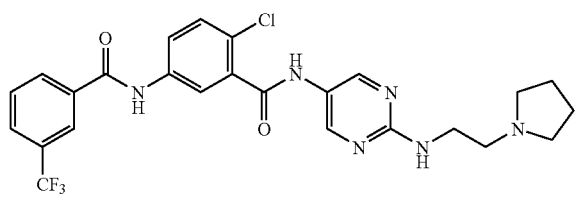
XXXVII
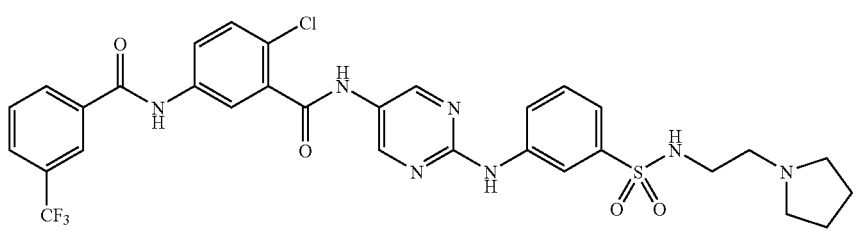

-continued
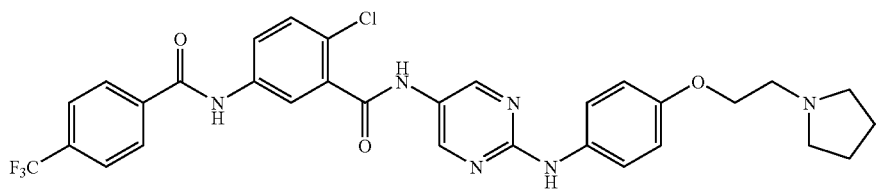
XXXVIII
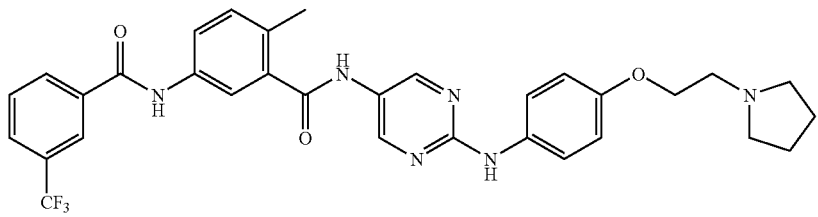
XXXIX
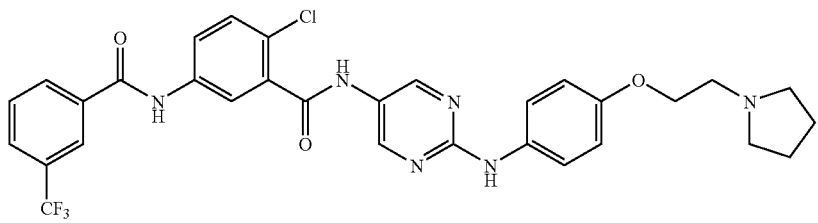
XL
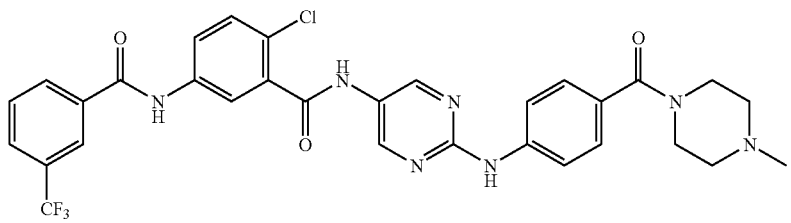
XLI
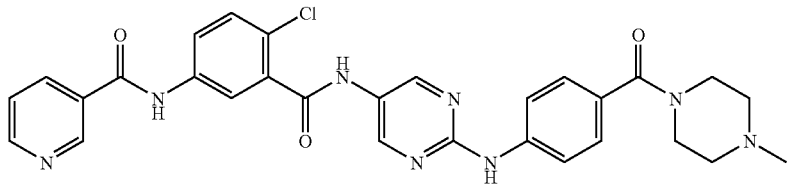
XLII
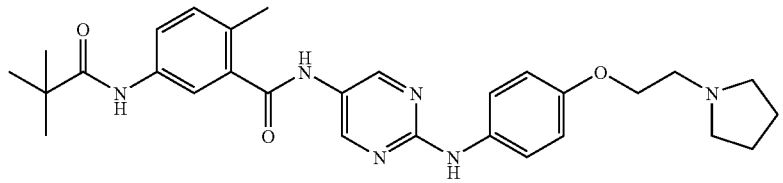
XLIII
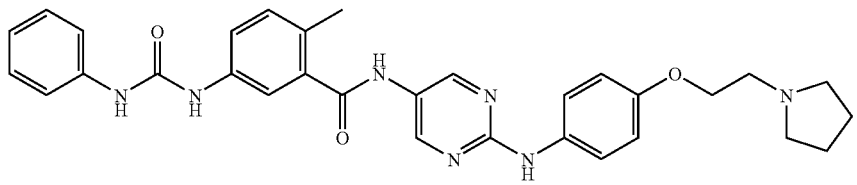
XLIV
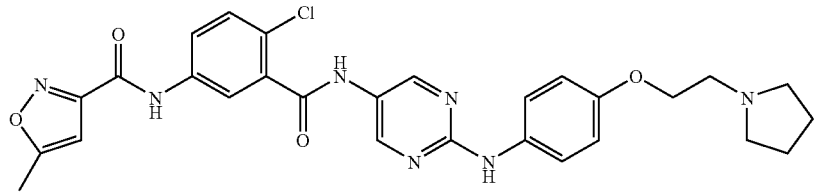
XLV -continued
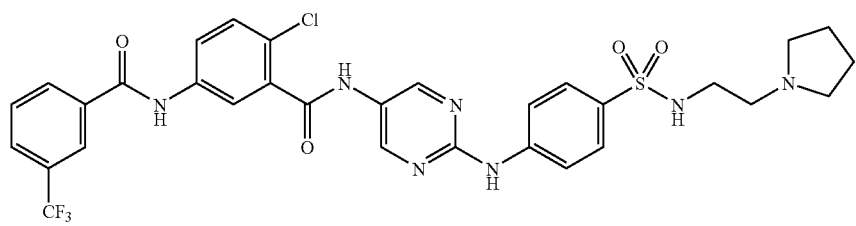
XLVI
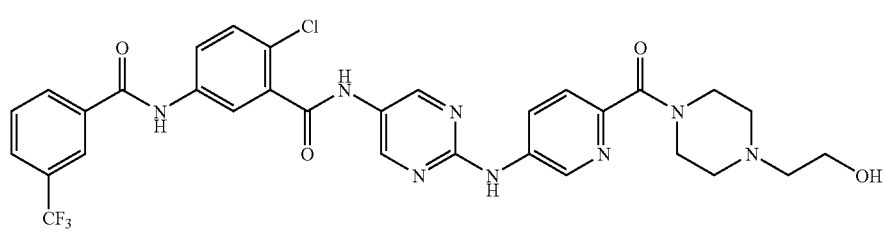
XLVII
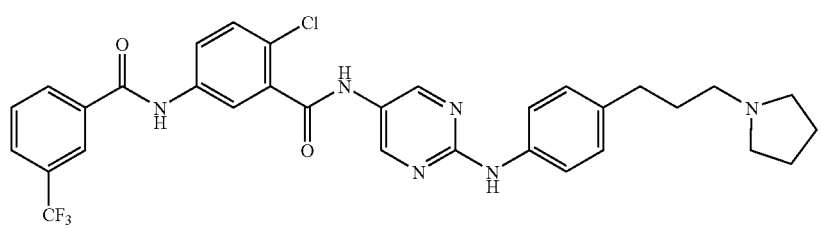
XLVIII
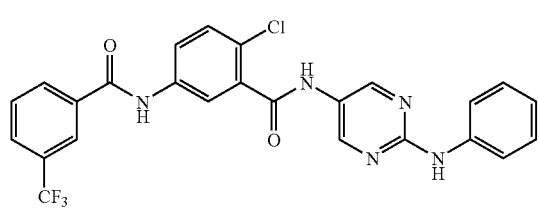
XLIX
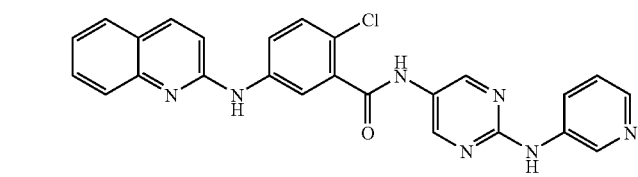
L
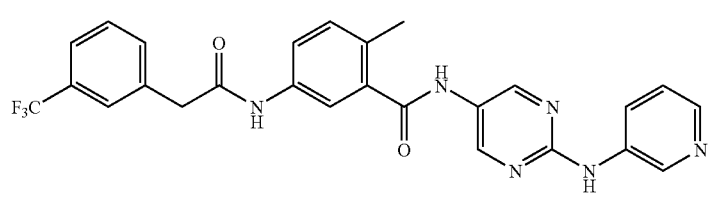
LI
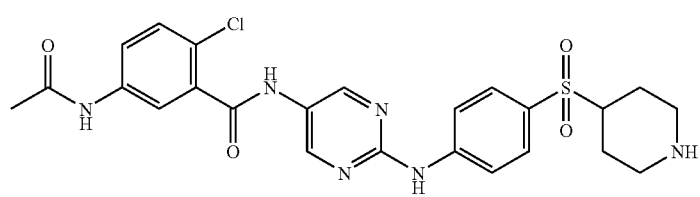
LII
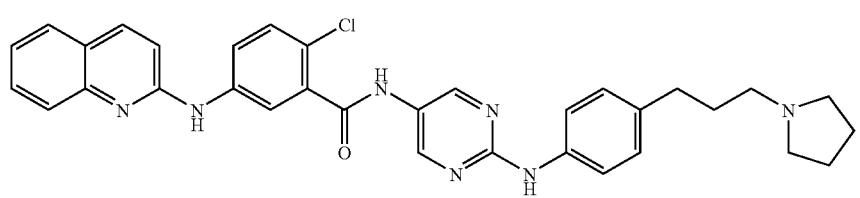
LIII -continued
LIV
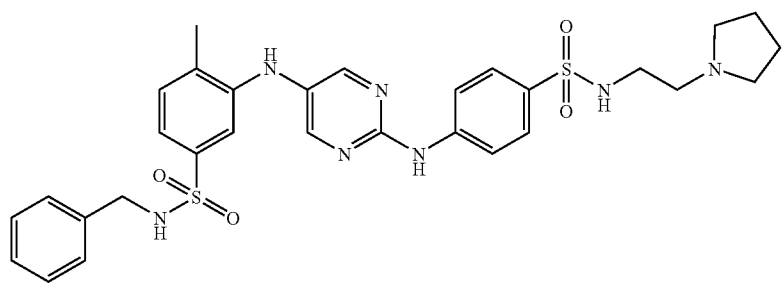
LV
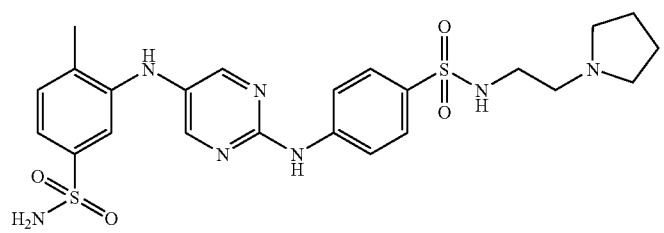
LVI
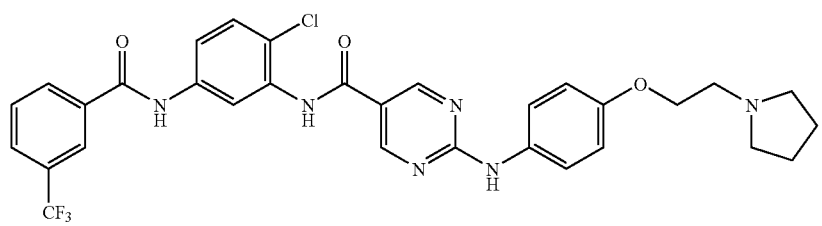
LVII
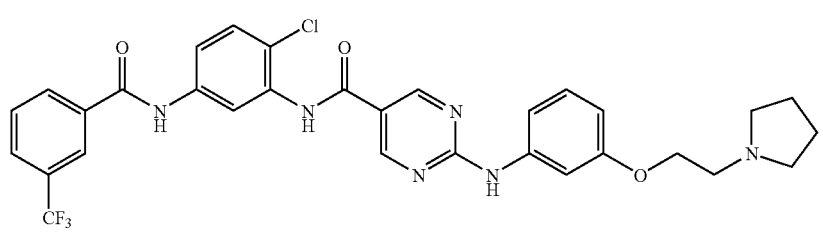
LVIII
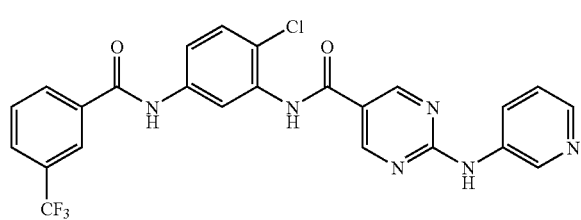
LIX
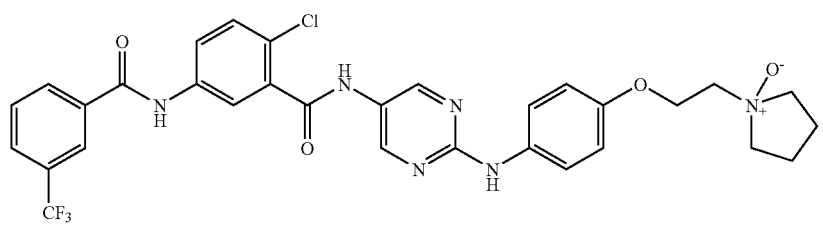
LX
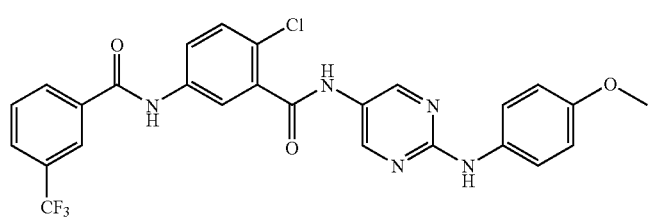

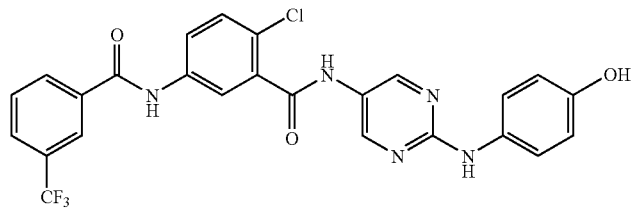

LXI

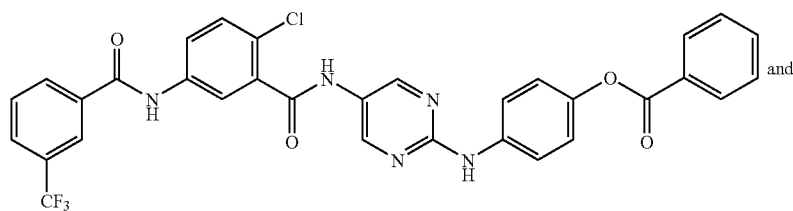

LXII

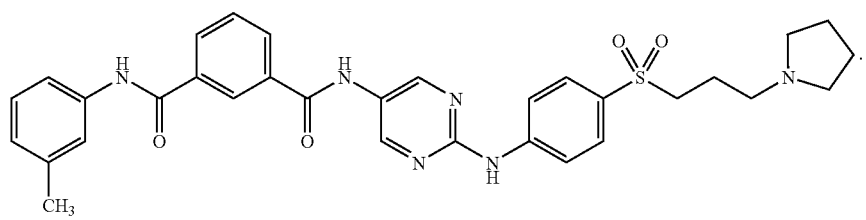

LXIII

The methods, compounds, and compositions of the present invention, either when administered alone or in combination with other agents (e.g., chemotherapeutic agents or protein therapeutic agents described below) are useful in treating a variety of disorders associated with compromised vasculostasis and other disorders, including but not limited to: stroke, cardiovascular disease, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), cancer, pleural effusions, rheumatoid arthritis, diabetic retinopathy, retinitis pigmentosa, and retinopathies, including diabetic retinopathy and retinopathy of prematurity, inflammatory diseases, restenosis, edema (including edema associated with pathologic situations such as cancers and edema induced by medical interventions such as chemotherapy), asthma, acute or adult respiratory distress syndrome (ARDS), lupus, vascular leakage, transplant (such as organ transplant, acute transplant or heterograft or homograft (such as is employed in burn treatment)) rejection; protection from ischemic or reperfusion injury such as ischemic or reperfusion injury incurred during organ transplantation, transplantation tolerance induction; ischemic or reperfusion injury following angioplasty; arthritis (such as rheumatoid arthritis, psoriatic arthritis or osteoarthritis); multiple sclerosis; inflammatory bowel disease, including ulcerative colitis and Crohn's disease; lupus (systemic lupus crythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including those where kinases such as Src-family kinases are activated or overexpressed, such as colon carcinoma and thymoma, or cancers where kinase activity facilitates tumor growth or survival; glomerulonephritis, serum sickness; uticaria; allergic diseases such as respiratory allergies (asthma, hay fever, allergic rhinitis) or skin allergies; mycosis fungoides; acute inflammatory responses (such as acute or adult respiratory distress syndrome and ischemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; morphea; peripheral limb ischemia and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculatides, including vasculitis, Kawasaki disease, thromboangiitis obliterans, Wegener's granulomatosis, and Behcet's disease; scleroderma; preeclampsia; thalassemia; Kaposi's sarcoma; von Hippel Lindau disease; and the like.

Also, the methods, compounds, and compositions of the present invention, either when administered alone or in combination with other agents (e.g., chemotherapeutic agents or protein therapeutic agents described below) are useful in treating a variety of ocular diseases and disorders, such as lid diseases or disorders, lacrimal gland diseases or disorders, conjunctival disorders, corneal disorders, iris, ciliary body and choroidal disorders, lens diseases or disorders, retinal diseases or disorders, optic nerve diseases or disorders, sclera diseases or disorders, and orbit diseases or disorders.

Some specific examples of ocular disorders and diseases that can be treated using the methods, compounds, and compositions of the present invention include, without limitations, Basal Cell Carcinoma of the Eyelid, Sebaceous Gland Carcinoma, Squamous Cell Carcinoma of the Eyelid, Papilloma of Eyelid, Pigmented Lesions of the Eyelid, Blepharitis, Hansen Disease, Hordeolum, Chalazion, Spider Bites, Hemagiomas of the lid, Laceration of Eyelid Ectropion, Entropion, Dermatochalasis, Distichiasis, Trichiasis, Xanthelasma, Eyelid Coloboma, Laser Tissue Resurfacing, Blepharospasm, Eyelid Myokymia, Floppy Eyelid Syndrome, Marcus Gunn Jaw-winking Syndrome, Ptosis of eye lid (Adult and congenital), Ptosis, Congenital, Dacryoadenitis, Dacryocystitis, Lacrimal Gland Tumors, Dry eye syndrome, Nasolacrimal Duct, Obstruction, Alacrima, Congenital Anomalies of Nasolacrimal Duct, Laceration, Canalicular, Squamous Cell Carcinoma of Conjunctiva, Papilloma conjunctiva, conjunctival melanoma, Kaposi Sarcoma, Bacterial Conjunctivitis, Viral Conjunctivitis, Pharyngoconjunctival Fever, Epidemic Keratoconjunctivitis, chemical burns, Cicatricial Pemphigoid, Allergic Conjunctivitis, Giant Papillary Conjunctivitis, Stevens-Johnson Syndrome, Atopic keratoconjunctivitis, Ocular Rosacea, Sub conjunctival hemorrhage, Pterygium, Filtering bleb complications, Dystrophies: Crystalline Dystrophy, Fuchs Endothelial Dystrophy, Granular Dystrophy, Lattice Dystrophy, Macular Dystrophy, Map-dot-Finger Dystrophy, Posterior Polymorphous Corneal Dystrophy, Herpes Simplex keratitis, Bacterial Keratitis, Fungal Keratitis, (and any complications following these infections), including autoimmune: Interstitial Keratitis, Atopic Keratoconjunctivitis, Keratoconjunctivitis Sicca, Superior Limbic Keratoconjunctivitis, Corneal Graft Rejection, Limbal stem cell transplantation and graft rejection, Band Keratopathy, Neurotrophic Keratopathy, Peripheral Ulcerative Keratitis, Dermoid, Limbal, tumors of the limbus, Corneal Neovascularization, (CL-related, post infectious, following any autoimmune disorders and stem cell deficiency), Post traumatic corneal edema, Keratoconus, Pellucid Marginal Degeneration, Terriens marginal degeneration (any complications arising including neovascularisation arising from these conditions), Central Sterile Corneal Ulceration, Congenital Clouding of the Cornea, Contact Lens Complications (including neovascularisation, corneal edema), Corneal Abrasion, Post operative Corneal Edema, Postoperative Corneal Melt, Recurrent Corneal Erosion, Corneal Foreign Body (and related complications), Descemet Membrane Folds, Corneoscleral Laceration (any complications including neovascularisation and corneal edema), Pseudophakic Bullous Keratopathy, Aniridia (and any complications related), TB, Toxoplasmosis, Choroidal Rupture, Ciliary Body Melanoma, Iris Melanoma, Iris Leiomyoma, Juvenile Xanthogranuloma, Choroidal Melanoma, Uveitis (Anterior, intermediate and posterior), Choroidal Neovascularization, Multifocal Choroidopathy and uveitic Syndromes, Sarcoidosis, Behcet's disease, Vogt Koyanagi Harada disease, Kawasaki Disease, Angioid Streaks (and any complications including Choroidal neovascularisation), Choroidal Detachment, Phacoanaphylaxis, Ataxia-telangiectasia, Neurofibromatosis-1, Sturge-Weber Syndrome, Wyburn—Mason Syndrome, von Hippel-Lindau Disease, Cancer Associated and Related Autoimmune Retinopathies, Retinoblastoma, ARMD (Exudative and non exudative), Acute Retinal Necrosis (and any complications), Acute Multifocal Placoid Pigment Epitheliopathy, Central Serous Chorioretinopathy, Eales Disease, Macular Edema, (Diabetic, post uveitic, post Retinitis pigmentosa and Irvine-Gass), Nonpseudophakic Cystoid Macular Edema, Sub retinal Neovascular Membranes, Neuroretinitis, Presumed Ocular Histoplasmosis Syndrome (and any complications like neovascularisation), CMV Retinitis, Birdshot Retinopathy, Diabetic Retinopathy (Non Proliferative and Proliferative), Retinopathies (Hemoglobinopathies, Purtscher, Valsalva), Terson Syndrome, White Dot Syndromes, Branch Retinal Artery Occlusion, Branch Retinal Vein Occlusion, Central Retinal Artery Occlusion, Central Retinal Vein Occlusion, Macroaneurysm, Retinopathy of Prematurity, Best Disease, Lattice Degeneration, Retinitis Pigmentosa, Juvenile Retinoschisis, Senile Retinoschisis, Epimacular Membrane, Macular Hole, Retinal detachment (Post operative, Exudative, Proliferative, Rhegmatogenous and Tractional), Meningioma, Optic Neuritis, Optic Neuropathy (Anterior Ischemic and compressive), Multiple Sclerosis, Papilledema, Pseudopapilledema, Toxic/Nutritional Optic Neuropathy, Idiopathic Intracranial Hypertension, Giant Cell Arteritis, Ocular Ischemic Syndrome, Sickle Cell Disease, Leukemias, Episcleritis, Scleritis, Ankylosing Spondylitis, Sjogren Syndrome, Orbital Cellulitis, Preseptal Cellulitis, Dermoid, orbital tumors, Carotid Cavernous Fistula Hemangioma (Capillary, venous and cavernous), Orbital Fracture, and Thyroid Ophthalmopathy.

The compounds, compositions, and methods of the present invention may be useful in inhibiting the Fc gamma induced respiratory burst response in neutrophils, and may also be useful in inhibiting the Fc gamma dependent production of TNF alpha. The ability to inhibit Fc gamma receptor dependent neutrophil, monocyte and macrophage responses may result in additional anti-inflammatory activity for the compounds employed in invention methods. This activity may be used, for example, in the treatment of inflammatory diseases, such as arthritis or inflammatory bowel disease. The compounds, compositions and methods of the present invention may also be useful in the treatment of autoimmune glomerulonephritis and other instances of glomerulonephritis induced by deposition of immune complexes in the kidney that trigger Fc gamma receptor responses and which can lead to kidney damage.

The compounds, compositions, and methods of the present invention may be also used to inhibit the Fc epsilon induced degranulation responses. The ability to inhibit Fc epsilon receptor dependent mast cell and basophil responses may result in additional anti-inflammatory activity for the present compounds beyond their effect on T cells.

The present invention also provides articles of manufacture comprising packaging material and a pharmaceutical composition contained within the packaging material, wherein the packaging material comprises a label which indicates that the pharmaceutical composition can be used for treatment of disorders and wherein the pharmaceutical composition comprises a compound according to the present invention. Thus, in one aspect, the invention provides a pharmaceutical composition including a therapeutic agent and a compound of the invention, wherein the compound is present in a concentration effective to reduce vascular leakage associated with indications or therapeutic agents which have vascular leak as a side effect. For example, administration of a compound of the invention can be in conjunction with IL-2, immunotoxins, antibodies or chemotherapeutics. In these cases, IL-2, immunotoxin, antibody or chemotherapeutic concentration can be determined by one having ordinary skill in the art according to standard treatment regimen or, for example, as determined by an in vivo animal assay.

The present invention also provides pharmaceutical compositions comprising IL-2, immunotoxin, antibody or chemotherapeutic and at least one invention compound in an amount effective for inhibiting vascular permeability, and a pharmaceutically acceptable vehicle or diluent. The compositions of the present invention may contain other therapeutic agents, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques known in the art of pharmaceutical formulation.

The compounds of the invention may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the invention include amine salts formed by the protonation of an amino group with inorganic acids such as hydrochloric acid, hydrobromic acid, hydroiodic acid, sulfuric acid, phosphoric acid, and the like. Salts of the invention also include amine salts formed by the protonation of an amino group with suitable organic acids, such as p-toluenesulfonic acid, acetic acid, and the like. Additional excipients which are contemplated for use in the practice of the present invention are those available to those of ordinary skill in the art, for example, those found in the United States Pharmacopoeia Vol. XXII and National Formulary Vol. XVII, U.S. Pharmacopoeia Convention, Inc., Rockville, Md. (1989), the relevant contents of which is incorporated herein by reference. In addition, polymorphs of the invention compounds are included in the present invention.

Pharmaceutical compositions of the invention may be administered by any suitable means, for example, orally, such as in the form of tablets, capsules, granules or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The pharmaceutical compositions for the administration of the compounds of this embodiment either alone or in combination with IL-2, immunotoxin, antibody or chemotherapeutic may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gel capsules, such as soft gelatin capsules, wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or co-solvent or complexing agent or dispersing agent or excipient or combination thereof, for example 1,3-butanediol, polyethylene glycols, polypropylene glycols, ethanol or other alcohols, povidones, various brands of TWEEN surfactant, sodium dodecyl sulfate, sodium deoxycholate, dimethylacetamide, polysorbates, poloxamers, cyclodextrins, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles).

In one aspect, the invention compounds are administered in combination with an anti-inflammatory agent, antihistamines, chemotherapeutic agent, immunomodulator, therapeutic antibody or a protein kinase inhibitor, e.g., a tyrosine kinase inhibitor, to a subject in need of such treatment. While not wanting to be limiting, chemotherapeutic agents include antimetabolites, such as methotrexate, DNA cross-linking agents, such as cisplatin/carboplatin; alkylating agents, such as canbusil; topoisomerase I inhibitors such as dactinomicin; microtubule inhibitors such as taxol (paclitaxol), and the like. Other chemotherapeutic agents include, for example, a vinca alkaloid, mitomycin-type antibiotic, bleomycin-type antibiotic, antifolate, colchicine, demecoline, etoposide, taxane, anthracycline antibiotic, doxorubicin, daunorubicin, carminomycin, epirubicin, idarubicin, mithoxanthrone, 4-dimethoxy-daunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methtrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like. Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase, and hydroxyurea, etc.; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-.alpha., etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis.

The pharmaceutical compositions and methods of the present invention may further comprise other therapeutically active compounds as noted herein which are usually applied in the treatment of the above mentioned pathological conditions. Examples of other therapeutic agents include the following: cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

Other agents that may be administered in combination with invention compounds include protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay.

The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

When other therapeutic agents are employed in combination with the compounds of the present invention they may be used for example in amounts as noted in the Physician Desk Reference (PDR) or as otherwise determined by one having ordinary skill in the art.

In the treatment or prevention of conditions which involve compromised vasculostasis an appropriate dosage level can generally be between about 0.01 and about 500 mg per 1 kg of patient body weight per day which can be administered in single or multiple doses. For example, the dosage level can be between about 0.01 and about 250 mg/kg per day; more narrowly, between about 0.5 and about 100 mg/kg per day. A suitable dosage level can be between about 0.01 and about 250 mg/kg per day, between about 0.05 and about 100 mg/kg per day, or between about 0.1 and about 50 mg/kg per day, or about 1.0 mg/kg per day. For example, within this range the dosage can be between about 0.05 and about 0.5 mg/kg per day, or between about 0.5 and about 5 mg/kg per day, or between about 5 and about 50 mg/kg per day. For oral administration, the compositions can be provided in the form of tablets containing between about 1.0 and about 1,000 mg of the active ingredient, for example, about 1.0, about 5.0, about 10.0, about 15.0, about 20.0, about 25.0, about 50.0, about 75.0, about 100.0, about 150.0, about 200.0, about 250.0, about 300.0, about 400.0, about 500.0, about 600.0, about 750.0, about 800.0, about 900.0, and about 1,000.0 mg of the active ingredient for the symptomatic adjustment of the dosage to the patient to be treated. The compounds can be administered on a regimen of 1 to 4 times per day, such as once or twice per day. There may be a period of no administration followed by another regimen of administration. Administration of the compounds can be associated with the schedule of IL-2 administration. For example, administration can be prior to, simultaneously with or immediately following IL-2 administration.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Compounds of the present invention can be used, alone or in combination with an effective amount of a therapeutic antibody (or therapeutic fragment thereof), a chemotherapeutic or an immunotoxic agent, for treatment of tumors. While doxorubicin, docetaxel, or taxol are described in the present application as illustrative examples of chemotherapeutic agents, it should be understood that the invention includes combination therapy including a compound of the invention, including but not limited to vasculostatic agents, such as tyrosine, serine or threonine kinase inhibitors, for example, Src-family inhibitors, and any chemotherapeutic agent or therapeutic antibody.

The following examples are provided to further illustrate the advantages and features of the present invention, but are not intended to limit the scope of the invention.

EXAMPLE 1

General Methods

All experiments were performed under anhydrous conditions (i.e. dry solvents) in an atmosphere of argon, except where stated, using oven-dried apparatus and employing standard techniques in handling air-sensitive materials.

Aqueous solutions of sodium bicarbonate (NaHCO$_3$) and sodium chloride (brine) were saturated. Analytical thin layer chromatography (TLC) was carried out on Merck Kieselgel 60 F$_{254}$ plates with visualization by ultraviolet and/or anisaldehyde, potassium permanganate or phosphomolybdic acid dips. Reverse-phase HPLC chromatography was carried out on Gilson 215 liquid handler equipped with Waters SymmetryShield™ RP 18 7 μm (40×100 mm) Prep-Pak cartridge. Mobile phase consisted of standard acetonitrile (ACN) and DI Water, each with 0.1% TFA added. Purification was carried out at a flow rate of 40 mL/min. NMR spectra: $^1$H Nuclear magnetic resonance spectra were recorded at 500 MHz. Data are presented as follows: chemical shift, multiplicity (s=singlet, d=doublet, t=triplet, q=quartet, qn=quintet, dd=doublet of doublets, m=multiplet, br s=broad singlet), coupling constant (J/Hz) and integration. Coupling constants were taken directly from the spectra and are uncorrected. Low resolution mass spectra: Electrospray (ES+) ionization was used. The protonated parent ion (M+H) or fragment of highest mass is quoted. Analytical gradient consisted of 10% ACN in water ramping up to 100% ACN over 5 minutes unless otherwise stated.

EXAMPLE 2

Synthesis of 5-(3-(Trifluoromethyl)Benzamido)-2-Chlorobenzoic Acid (Intermediate 1)

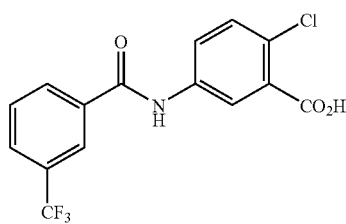

To a stirring solution of 5-amino-2-chlorobenzoic acid (1.74 g, 10.1 mmol) in anhydrous THF (60 mL), 3-(trifluoromethyl)benzoyl chloride (2.33 g, 11.2 mmol) was added slowly. The mixture was stirred at room temperature under argon for overnight. The solvent was removed under reduced pressure and re-crystallized from acetone/chloroform (v/v 1:1) to afford the title compound as a white solid (1.5 g, 43%).

$^1$H NMR (500 MHz, DMSO-d$_6$): δ 7.55 (d, J=8.8 Hz, 1H), 7.80 (t, J=7.8 Hz, 1H), 7.99 (dd, J=8.7 Hz, J=2.5 Hz, 2H), 8.15-8.35 (m, 2H), 8.32 (s, 1H), 10.69 (s, 1H), 13.47 (br s, 1H).

EXAMPLE 3

Synthesis of N-[4-(3-Pyrrolidin-1-yl-Propane-1-Sulfonyl)-Phenyl]-Pyrimidine-2,5-Diamine (Intermediate 2)

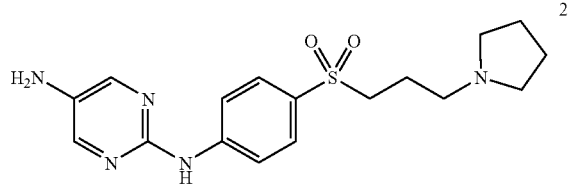

To a solution of 2-amino-5-nitropyrimidine (840 mg, 6.0 mmol) in 50 mL anhydrous 1,4-dioxane were added 1-[3-(4-bromo-benzenesulfonyl)-propyl]-pyrrolidine (2.9 g, 8.7 mmol), Xantphos, (690 mg, 1.2 mmol), Pd$_2$(dba)$_3$ (559 mg, 0.61 mmol) and Cs$_2$CO$_3$ (5.8 g, 18 mmol). The reaction mixture was stirred at 100° C. for 5 h under argon. The solvent was removed under reduced pressure. The resulting solution was extracted with CHCl$_3$ (3×50 mL) and sat. NaHCO$_3$ (50 mL). The organic layer was separated, washed with brine, dried over Na$_2$SO$_4$ and filtered. The organic solvent was removed and the crude product was purified by silica gel column with 20% CH$_3$OH/CHCl$_3$ as an eluent. The precipitated yellow solid was isolated by washed with acetone and dried in vacuo (1.2 g, 52%). The above product was hydrogenated in 100 mL methanol/ethyl acetate (v/v: 1:1) using Pd/C (10%, 1 g) for 2 h. The palladium catalyst was removed by filtration, and the solvent was evaporated. The pale yellow solid was isolated by washed with acetone/methanol (v/v 5:1) and dried in vacuo (550 mg, 49%).

$^1$H NMR (DMSO-d$_6$): δ 1.60-1.68 (m, 6H), 2.10-2.35 (m, 4H), 2.40-2.50 (m, 2H), 3.05-3.25 (m, 2H), 5.02 (br s, 2H), 7.68 (d, J=9.0 Hz, 2H), 7.87 (d, J=9.0 Hz, 1H), 8.02 (s, 2H), 9.68 (s, 1H).

EXAMPLE 4

Synthesis of Chloro-N-{2-[4-(3-Pyrrolidin-1-yl-Propane-1-Sulfonyl)-Phenylamino]-Pyrimidin-5-yl}-5-(3-Trifluoromethyl-Benzoylamino)-Benzamide (Compound I)

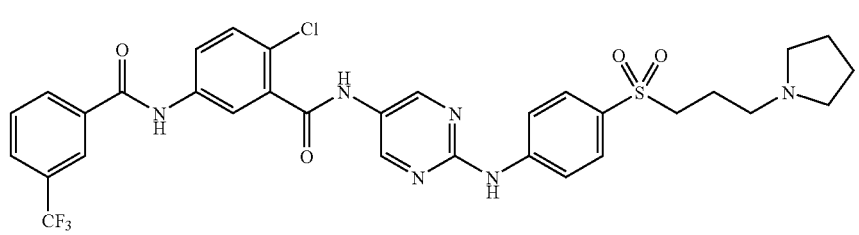

To a solution of intermediates 2 (Example 3) (35 mg, 0.1 mmol) and 1 (Example 2) (67 mg, 0.2 mmol) in anhydrous CH$_2$Cl$_2$ (5 mL) and anhydrous DMF (1 mL), O-(7-azabenzotriazol-1-yl)-N,N,N',N'-tetramethyluronium hexafluorophosphate (HATU, 110 mg, 0.3 mmol) and N,N-diisopropylethylamine (50 mg, 0.4 mmol) were added. The reaction mixture was stirred at room temperature for 16 h, and the solvent was removed. The residue was dissolved in CH$_2$Cl$_2$ (20 mL) and washed with aqueous saturated NaHCO$_3$ solution (20 mL). The aqueous layer was extracted with CH$_2$Cl$_2$ (50 mL). The combined organic phase was dried (Na$_2$SO$_4$) and the solvent was removed. The crude product was purified by silica gel column with CHCl$_3$ to 15% CH$_3$OH/CHCl$_3$ as eluents to give the final product as a white solid (10 mg, 15%).

$^1$H NMR (DMSO-d$_6$) δ 1.55-1.85 (m, 6H), 2.20-2.55 (m, 6H), 1.85-2.10 (m, 2H), 3.24 (t, J=7.8 Hz, 2H), 7.62 (d, J=8.8 Hz, 1H), 7.78 (d, J=8.9 Hz, 2H), 7.82 (t, J=7.9 Hz, 1H), 7.95 (dd, J=8.8 Hz, J=2.6 Hz, 1H), 7.85-8.15 (m, 3H), 8.07 (d, J=2.6 Hz, 1H), 8.29 (d, J=8.0 Hz, 1H), 8.32 (s, 1H), 8.90 (s, 2H), 10.30 (s, 1H), 10.75 (s, 1H), 10.79 (s, 1H). MS (ES+): m/z 687 (M+H)$^+$.

EXAMPLE 5

Synthesis of 5-(3-(Trifluoromethyl)Benzamido)-2-Methylbenzoic Acid (Intermediate 3)

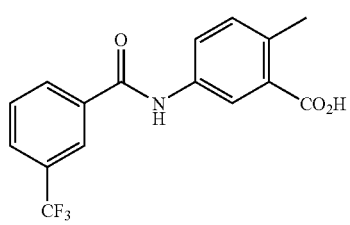

3

To a stirring solution of 5-amino-2-methylbenzoic acid (600 mg, 4.0 mmol) in anhydrous THF (25 mL), 3-(trifluoromethyl)benzoyl chloride (910 mg, 4.3 mmol) was added slowly. The mixture was stirred at room temperature under argon for overnight. The solvent was removed under reduced pressure and re-crystallized from acetone to afford the title compound as a white solid (600 mg, 47%).

EXAMPLE 6

Synthesis of 2-Methyl-N-{2-[4-(3-Pyrrolidin-1-yl-Propane-1-Sulfonyl)-Phenylamino]-Pyrimidin-5-yl}-5-(3-Trifluoromethyl-Benzoylamino)-Benzamide (Compound II)

To a solution of intermediate 3 (Example 5) (170 mg, 0.5 mmol) in anhydrous CH$_2$Cl$_2$ (8 mL), 2-chloro-4,6-dimethoxy-1,3,5-triazine (100 mg, 0.6 mmol) and 4-methylmorpholine (210 mg, 2 mmol) were added. After the reaction mixture was stirred at room temperature for 75 minutes, intermediate 2 (Example 3) (100 mg, 0.3 mmol) in anhydrous DMF (2.5 mL) was added into the solution. The solution was stirred under argon for overnight. The residue was dissolved in CH$_2$Cl$_2$ (20 mL) and washed with aqueous saturated NaHCO$_3$ solution (20 mL). The aqueous layer was extracted with CH$_2$Cl$_2$ (50 mL). The combined organic phase was dried (Na$_2$SO$_4$) and the solvent was removed. The crude product was purified by silica gel column with CHCl$_3$ to 10% CH$_3$OH/CHCl$_3$ as eluents to give the final product as a white solid (27 mg, 15%).

$^1$H NMR (DMSO-d$_6$): δ 1.65-1.95 (m, 6H), 2.39 (s, 3H), 2.80 (br s, 6H), 7.34 (d, J=8.4 Hz, 1H), 7.65-7.90 (m, 4H), 7.95-8.10 (m, 4H), 8.29 (d, J=7.9 Hz, 1H), 8.33 (s, 1H), 8.92 (s, 2H), 10.29 (s, 1H), 10.57 (s, 1H), 10.61 (s, 1H). MS (ES+): m/z 667 (M+H)$^+$.

EXAMPLE 7

Synthesis of 5-(3-Methylbenzamido)-2-Chlorobenzoic Acid (Intermediate 4)

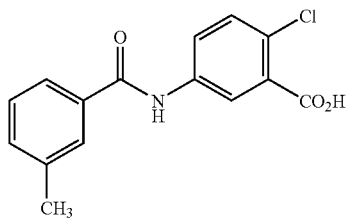

4

To a stirring solution of 5-amino-2-chlorobenzoic acid (880 mg, 5.1 mmol) in anhydrous THF (45 mL), 3-methylbenzoyl chloride (870 mg, 5.6 mmol) was added slowly. The mixture was stirred at room temperature under argon for overnight. The solvent was removed under reduced pressure and re-crystallized from chloroform to afford the title compound as a white solid (1.2 g, 80%).

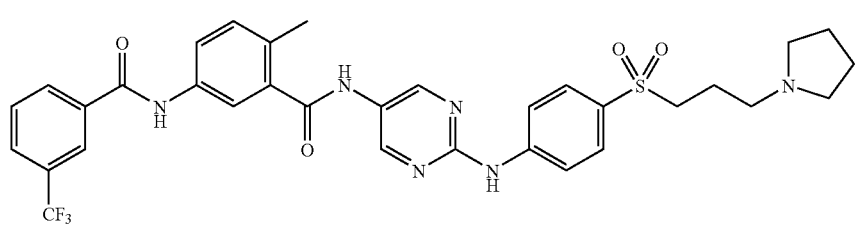

II

EXAMPLE 8

Synthesis of 2-Chloro-5-(3-Methyl-Benzoylamino)-N-{2-[4-(3-Pyrrolidin-1-yl-Propane-1-Sulfonyl)-Phenylamino]-Pyrimidin-5-yl}-Benzamide (Compound III)

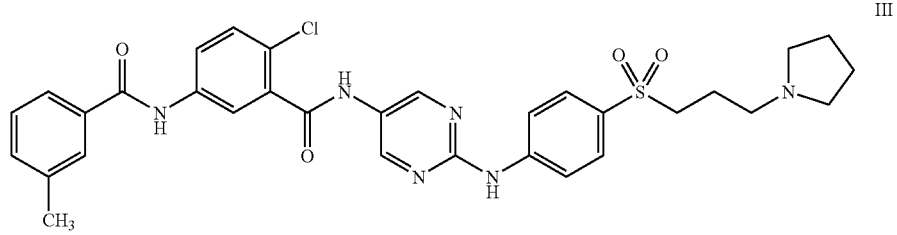

To a solution of intermediate 4 (Example 7) (290 mg, 1 mmol) in anhydrous $CH_2Cl_2$ (30 mL), 2-chloro-4,6-dimethoxy-1,3,5-triazine (210 mg, 1.2 mmol) and 4-methylmorpholine (300 mg, 3 mmol) were added. After the reaction mixture was stirred at room temperature for 75 minutes, intermediate 2 (Example 3) (100 mg, 0.3 mmol) in anhydrous DMF (2.5 mL) was added into the solution. The solution was stirred under argon for overnight. The residue was dissolved in $CH_2Cl_2$ (20 mL) and washed with aqueous saturated $NaHCO_3$ solution (20 mL). The aqueous layer was extracted with $CH_2Cl_2$ (50 mL). The combined organic phase was dried ($Na_2SO_4$) and the solvent was removed. The crude product was purified by silica gel column with $CHCl_3$ to 10% $CH_3OH/CHCl_3$ as eluents to give the final product as a white solid (85 mg, 13%).

$^1$H NMR (DMSO-$d_6$): δ 1.55-1.95 (m, 6H), 2.32 (br s, 4H), 2.40 (br s, 5H), 7.43 (d, J=5.0 Hz, 1H), 7.57 (d, J=8.8 Hz, 1H), 7.60-7.95 (m, 3H), 7.82 (s, 1H), 7.97 (dd, J=8.9 Hz, J=2.6 Hz, 1H), 8.01 (d, J=8.9 Hz, 2H), 8.12 (d, J=2.5 Hz, 1H), 8.91 (s, 2H), 10.30 (s, 1H), 10.59 (s, 1H), 10.83 (s, 1H). MS (ES+): m/z 633 (M+H)$^+$.

EXAMPLE 9

Synthesis of 3-(3-(Trifluoromethyl)Benzamido)Benzoic Acid (Intermediate 5)

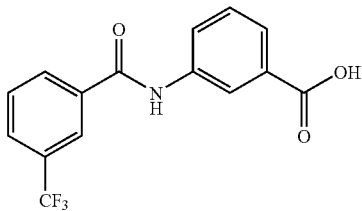

To a stirring solution of 3-aminobenzoic acid (1.1 g, 7.9 mmol) in anhydrous THF (20 mL), 3-(trifluoromethyl)benzoyl chloride (2.0 g, 9.6 mmol) was added slowly. The mixture was stirred at room temperature under argon for overnight. The solvent was removed under reduced pressure and re-crystallized from chloroform to afford the title compound as a white solid (1.2 g, 49%).

EXAMPLE 10

Synthesis of N-{2-[4-(3-Pyrrolidin-1-yl-propane-1-sulfonyl)-phenylamino]-pyrimidin-5-yl}-3-(3-trifluoromethyl-benzoylamino)-benzamide (Compound IV)

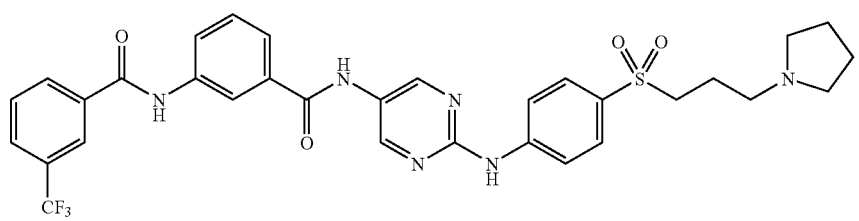

To a solution of intermediate 5 (Example 9) (240 mg, 0.8 mmol) in anhydrous CH$_2$Cl$_2$ (15 mL), 2-chloro-4,6-dimethoxy-1,3,5-triazine (170 mg, 1 mmol) and 4-methylmorpholine (160 mg, 1.6 mmol) were added. After the reaction mixture was stirred at room temperature for 75 minutes, intermediate 2 (Example 3) (100 mg, 0.3 mmol) in anhydrous DMF (2.5 mL) was added into the solution. The solution was stirred under argon for overnight. The residue was dissolved in CH$_2$Cl$_2$ (20 mL) and washed with aqueous saturated NaHCO$_3$ solution (20 mL). The aqueous layer was extracted with CH$_2$Cl$_2$ (50 mL). The combined organic phase was dried (Na$_2$SO$_4$) and the solvent was removed. The crude product was purified by silica gel column with CHCl$_3$ to 10% CH$_3$OH/CHCl$_3$ as eluents to give the final product as a pale yellow solid (100 mg, 19%).

$^1$H NMR (DMSO-d$_6$): δ 1.71-2.05 (m, 6H), 2.90 (br s, 2H), 3.20 (br s, 2H), 3.40 (t, J=7.3 Hz, 4H), 7.56 (t, J=8.0 Hz, 1H), 7.60-7.90 (m, 3H), 7.85 (d, J=7.8 Hz, 1H), 7.99 (d, J=7.8 Hz, 1H), 7.95-8.15 (m, 3H), 8.10-8.50 (m, 3H), 8.99 (s, 2H), 10.30 (s, 1H), 10.68 (s, 1H), 10.80 (s, 1H), 11.10 (br s, 1H). MS (ES+): m/z 653 (M+H)$^+$.

EXAMPLE 11

Synthesis of Ethyl 3-(5-Aminopyrimidin-2-ylamino)Benzoate (Intermediate 6)

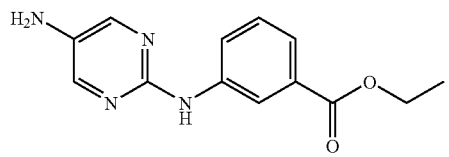

6

To a solution of 2-amino-5-nitropyrimidine (550 mg, 3.9 mmol) in 35 mL anhydrous 1,4-dioxane were added ethyl 3-bromobenzoate (1.8 g, 7.9 mmol), Xantphos, (230 mg, 0.4 mmol), Pd$_2$(dba)$_3$ (180 mg, 0.2 mmol) and Cs$_2$CO$_3$ (2.6 g, 8 mmol). The reaction mixture was stirred at 100° C. for 5 h under argon. The solvent was removed under reduced pressure. The resulting solution was extracted with CHCl$_3$ (3×50 mL) and saturated NaHCO$_3$ (50 mL). The organic layer was separated, washed with brine, dried over Na$_2$SO$_4$ and filtered. The organic solvent was removed and the crude product was purified by silica gel column with CHCl$_3$ as an eluent. The precipitated yellow solid was isolated by washed with chloroform and dried in vacuo (700 mg, 62%). $^1$H NMR (DMSO-d$_6$): δ 1.33 (t, J=7.1 Hz, 3H), 4.33 (q, J=7.1 Hz, 2H), 7.54 (t, J=8.0 Hz, 1H), 7.60-7.90 (m, 1H), 7.95-8.10 (m, 1H), 8.37 (t, J=1.9 Hz, 1H), 9.26 (s, 2H), 11.00 (s, 1H).

The above product was hydrogenated in 100 mL methanol/ethyl acetate (v/v: 1:1) using Pd/C (10%, 1 g) for 2 h. The palladium catalyst was removed by filtration, and the solvent was evaporated. The crude product was purified by silica gel column with 5% CH$_3$OH/CHCl$_3$ as an eluent to yield an off-white solid. MS (ES+): m/z 259 (M+H)$^+$.

EXAMPLE 12

Synthesis of 3-{5-[2-Chloro-5-(3-Trifluoromethyl-benzoylamino)-Benzoylamino]-Pyrimidin-2-ylamino}-Benzoic Acid Ethyl Ester (Compound V)

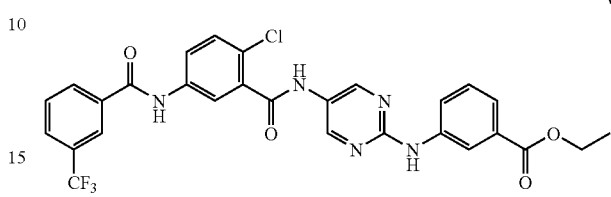

V

To a solution of intermediate 1 (Example 2) (280 mg, 0.8 mmol) in anhydrous CH$_2$Cl$_2$ (15 mL), 2-chloro-4,6-dimethoxy-1,3,5-triazine (180 mg, 1 mmol) and 4-methylmorpholine (250 mg, 2.5 mmol) were added. After the reaction mixture was stirred at room temperature for 75 minutes, intermediate 6 (Example 11) (110 mg, 0.4 mmol) in anhydrous DMF (2.5 mL) was added into the solution. The solution was stirred under argon for overnight. The residue was dissolved in CH$_2$Cl$_2$ (20 mL) and washed with aqueous saturated NaHCO$_3$ solution (20 mL). The aqueous layer was extracted with CH$_2$Cl$_2$ (50 mL). The combined organic phase was dried (Na$_2$SO$_4$) and the solvent was removed. The crude product was purified by silica gel column with CHCl$_3$ to 10% CH$_3$OH/CHCl$_3$ as eluents to give the final product as a pale yellow solid (100 mg, 21%).

$^1$H NMR (DMSO-d$_6$): δ 1.33 (t, J=7.2 Hz, 3H), 4.32 (q, J=7.0 Hz, 2H), 7.43 (t, J=7.8 Hz, 1H), 7.53 (d, J=7.7 Hz, 1H), 7.61 (d, J=8.8 Hz, 1H), 7.82 (t, J=8.0 Hz, 1H), 7.90-8.10 (m, 4H), 8.31 (d, J=16.1 Hz, 1H), 8.33 (br s, 1H), 8.40 (br s, 1H), 8.83 (s, 2H), 9.92 (s, 1H), 10.70 (s, 1H), 10.74 (s, 1H). MS (ES+): m/z 584 (M+H)$^+$.

EXAMPLE 13

Synthesis of N-(4-Chloro-3-Hydroxymethyl-Phenyl)-3-Trifluoromethyl-Benzamide (Intermediate 7)

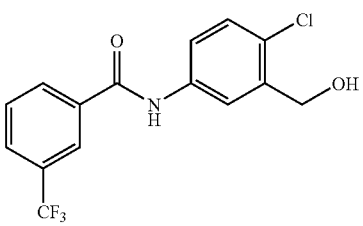

7

To a solution of intermediate 1 (Example 2) (1.4 g, 4.1 mmol) in anhydrous THF (20 mL) at room temperature under argon, 1.5 M diisobutylaluminum hydride in toluene (DIBAL-H, 9 mL, 13.5 mmol) was added. After the reaction mixture was stirred at room temperature for 1 h, the solution was refluxed under argon for overnight. The solution was quenched by minimum amount of methanol and water. The organic solvent was removed by reduced pressure. The crude was suspended in water (50 mL) and extracted by ethyl acetate (2×50 mL). The organic layers were combined, washed with brine, dried over Na₂SO₄ and filtered. The organic solvent was removed and the crude product was purified by silica gel column with CHCl₃ as an eluent to give the final product as a white solid (700 mg, 52%).

¹H NMR (DMSO-d₆): δ 4.57 (d, J=5.5 Hz, 2H), 5.49 (t, J=5.5 Hz, 1H), 7.39 (d, J=8.7 Hz, 1H), 7.75-7.95 (m, 2H), 8.00-8.20 (m, 2H), 8.28 (d, J=7.9 Hz, 1H), 8.31 (s, 1H), 10.59 (s, 1H).

EXAMPLE 14

Synthesis of N-(4-Chloro-3-Formyl-Phenyl)-3-Trifluoromethyl-Benzamide (Intermediate 8)

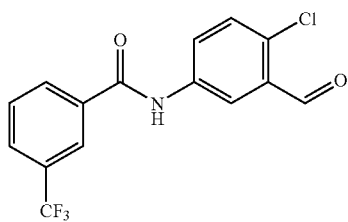

8

The solution of intermediate 7 (Example 13) (700 mg, 2.1 mmol) and MnO₂ (1.8 g, 21 mmol) in anhydrous toluene (30 mL) was refluxed for 2 h. After cooling down, the MnO₂ was removed by filtration. The solvent was removed by reduced pressure. The solid was re-crystallized from chloroform to yield an off-white solid (300 mg, 43%).

¹H NMR (DMSO-d₆): δ 7.66 (d, J=3.7 Hz, 1H), 7.81 (t, J=7.8 Hz, 1H), 8.00 (d, J=7.7 Hz, 1H), 8.14 (dd, J=8.7 Hz, J=2.4 Hz, 1H), 8.28 (d, J=7.6 Hz, 1H), 8.33 (s, 2H), 10.35 (s, 1H), 10.78 (s, 1H).

EXAMPLE 15

Synthesis of N²-(Pyridin-3-yl)Pyrimidine-2,5-Diamine (Intermediate 9)

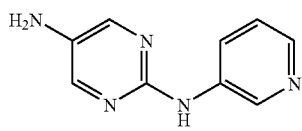

9

To a solution of 2-amino-5-nitropyrimidine (800 mg, 5.7 mmol) in 50 mL anhydrous 1,4-dioxane were added 3-bromopyridine (1.8 g, 11.4 mmol), Xantphos, (330 mg, 0.6 mmol), Pd₂(dba)₃ (260 mg, 0.5 mmol) and Cs₂CO₃ (3.7 g, 11.3 mmol). The reaction mixture was stirred at 100° C. for 5 h under argon. After cooling down, the solvent was removed under reduced pressure. The precipitated yellow solid was isolated by washing with acetone to yield a pale yellow solid (800 mg, 64%). ¹H NMR (DMSO-d₆): δ 7.41 (dd, J=8.3 Hz, J=4.7 Hz, 1H), 8.15 (d, J=8.1 Hz, 1H), 8.31 (d, J=8.8 Hz, 1H), 8.87 (d, J=2.1 Hz, 1H), 9.24 (s, 2H), 10.98 (br s, 1H).

The above product was hydrogenated in 50 mL methanol/ethyl acetate (v/v: 1:1) using Pd/C (10%, 1 g) for 2.5 h. The palladium catalyst was removed by filtration, and the solvent was evaporated. The pale yellow solid was isolated by washed with acetone and dried in vacuo (500 mg, 73%). MS (ES+): m/z 188 (M+H)⁺.

EXAMPLE 16

Synthesis of N-(4-Chloro-3-{[2-(Pyridin-3-ylamino)-Pyrimidin-5-ylamino]-Methyl}-Phenyl)-3-Trifluoromethyl-Benzamide (Compound VI)

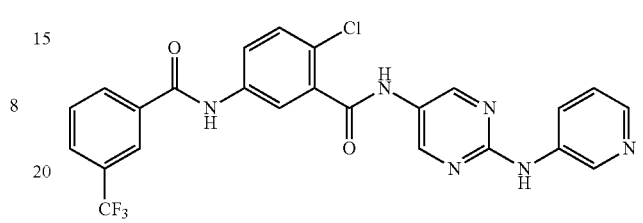

VI

The solution of intermediates 8 (Example 14) (200 mg, 0.6 mmol) and 9 (Example 15) (110 mg, 0.6 mmol) in anhydrous toluene (35 mL) was refluxed with a Dean-Stark for 12 h. After cooling down, the solvent was removed under reduced pressure. The crude product was purified by silica gel column with CHCl₃ to 5% CH₃OH/CHCl₃ as eluents to give the final product as a yellow solid (100 mg, 33%).

To a solution of the above product (60 mg, 0.1 mmol) in 1,4-dioxane (30 mL) containing AcOH (0.5 mL), NaBH₃CN (0.38 g, 6 mmol) was added in small portions over 20 minutes. The solution was refluxed for 2 h. After cooling down, the solvent was removed by reduced pressure. The crude product was purified by silica gel column with CHCl₃ to 3% CH₃OH/CHCl₃ as eluents to give the final product as a off-white solid after washed with chloroform (15 mg, 25%).

¹H NMR (DMSO-d₆): δ 4.39 (d, J=5.7 Hz, 2H), 6.40 (t, J=6.0 Hz, 1H), 7.49 (d, J=8.6 Hz, 1H), 7.60-7.90 (m, 2H), 7.85 (d, J=2.5 Hz, 1H), 7.95 (d, J=8.0 Hz, 1H), 8.06 (s, 2H), 8.09 (d, J=5.6 Hz, 1H), 8.21 (d, J=7.9 Hz, 1H), 8.22 (s, 1H), 8.46 (d, J=8.7 Hz, 1H), 9.11 (d, J=2.1 Hz, 1H), 10.01 (s, 1H), 10.57 (s, 1H). MS (ES+): m/z 499 (M+H)⁺.

EXAMPLE 17

Synthesis of 4-(4-Bromo-Phenylsulfanyl)-Piperidine-1-Carboxylic Acid Benzyl Ester (Intermediate 10)

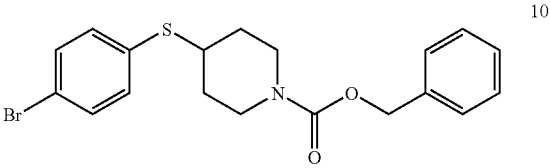

10

4-bromo-benzenethiol (0.63 g, 3.4 mmol), 4-bromo-piperidine-1-carboxylic acid benzyl ester (1.0 g, 3.4 mmol) and cesium carbonate (2.2 g, 6.7 mmol) were refluxed in acetone for 2 h. Reaction solvents were then removed and resulting white solids were taken up in EtOAc and washed with water then brine. Organic phase was then dried over sodium sulfate, filtered and evaporated to clear oil (1.2 g, 88% yield). $R_f$=0.45 (20% EtOAc/Hexane).

EXAMPLE 18

Synthesis of 4-(4-Bromo-Benzenesulfonyl)-Piperidine-1-Carboxylic Acid tert-Butyl Ester (Intermediate 11)

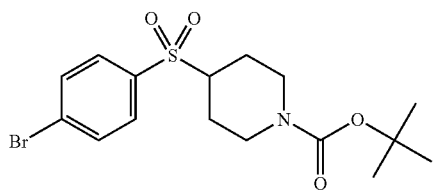

11

A solution of intermediate 10 (Example 17) (1.2 g, 2.96 mmol) and sodium perborate tetrahydrate (NaBO$_3$.4H$_2$O) (1.36 g, 8.87 mmol) were heated to 55° C. in HOAc and stirred for 18 h. Reaction was then cooled to room temperature and poured onto water. Aqueous phase was extracted with EtOAc (3×100 mL). Organic phases were combined and washed carefully with saturated sodium bicarbonate solution, taken in account copious gas evolution, dried over sodium sulfate, filtered and evaporated to white solids (1.2 g, 93% yield). $R_f$=0.16 (20% EtOAc/Hexane).

EXAMPLE 19

Synthesis of 4-[4-(5-Nitro-Pyrimidin-2-ylamino)-Benzenesulfonyl]-Piperidine-1-Carboxylic Acid tert-Butyl Ester (Intermediate 12)

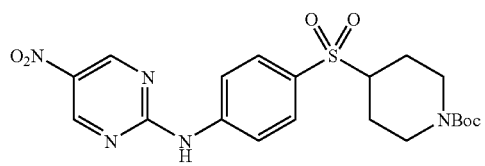

12

In a dry 50 mL round bottom flask 5-nitro-pyrimidin-2-ylamine (1 g, 7.14 mmol), intermediate 11 (Example 18) (4.03 g, 9.99 mmol), cesium carbonate (7 g, 21.43 mmol), 4,5-bis(diphenylphosphino)-9,9-dimethyl xanthene (0.827 g, 1.43 mmol) and tris(dibenzylideneacetone) dipalladium (0.654 g, 0.714 mmol) were combined. Reactants were flushed with argon, diluted with dioxane (40 mL) and outfitted with reflux condenser. Reaction was heated to reflux for 5 h. Reaction was cooled to room temperature, poured onto water and extracted with EtOAc (3×125 mL). Organic phase was evaporated yielding yellow solids, 4.1 g. Silica gel chromatography provided the desired nitro sulfone as a yellow powder (2 g, 61% yield).

EXAMPLE 20

Synthesis of 4-[4-(5-Amino-Pyrimidin-2-ylamino)-Benzenesulfonyl]-Piperidine-1-Carboxylic Acid tert-Butyl Ester (Intermediate 13)

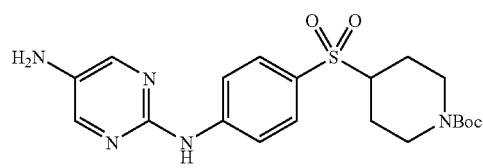

13

A methanolic solution of intermediate 12 (Example 19) (3 g, 6.48 mmol) was purged with argon for several minutes, then treated with approximately 1 g of Raney Nickel. Reaction atmosphere was evacuated and replaced with hydrogen added via a hydrogen-filled balloon. After 3 h, the hydrogen balloon was removed and reaction solvents purged with argon. Catalyst was then removed using magnetic stirring-bar retriever. Solvents were then removed providing the desired amine as an off-white solid (2.5 g, 89% yield).

EXAMPLE 21

Synthesis of 4-(4-{5-[2-Chloro-5-(3-Trifluoromethyl-Benzoylamino)-Benzoylamino]-Pyrimidin-2-ylamino}-Benzenesulfonyl)-Piperidine-1-Carboxylic Acid tert-Butyl Ester (Intermediate 14)

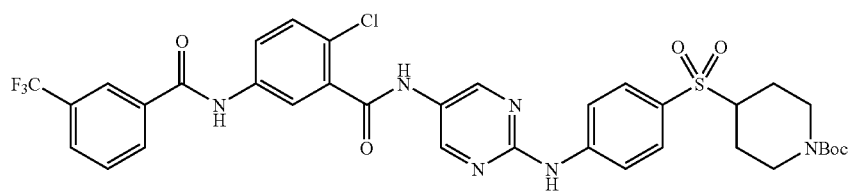

14

Intermediate 1 (Example 2) (0.098 g, 0.286 mmol) was combined with 2-chloro-4,6-dimethoxy-1,3,5-triazine (CDMT) (0.060 g, 0.343 mmol) and diluted with DCM (4 mL). This was immediately treated with 4-methyl morpholine (0.063 mL, 0.55 mmol) and allowed to stir at ambient temperature for 1 h. Intermediate 13 (Example 20) (0.130 g, 0.3 mmol) was then added in one portion. Stirring was continued overnight. After 18 h, reaction solvents were removed and resulting crude solids were purified via HPLC to afford the title compound as a white solid (0.056 g, 26%).

EXAMPLE 22

Synthesis of 2-Chloro-N-{2-[4-(Piperidine-4-Sulfonyl)-Phenylamino]-Pyrimidin-5-yl}-5-(3-Trifluoromethyl-Benzoylamino)-Benzamide (Compound VII)

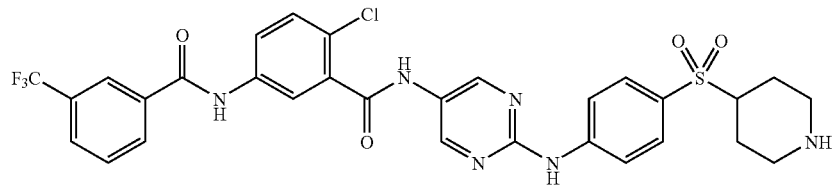

A stirred suspension of intermediate 14 (Example 21) (0.058 g, 0.076 mmol) in DCM (8 mL) was treated with TFA (0.100 mL) and stirred for 3 h. Solvents were then removed yielding desired product as TFA salt (0.05 g, 99%). $^1$H NMR (DMSO-d$_6$): δ 1.62-1.70 (m, 2H), 2.01-2.08 (m, 4H), 2.8-2.9 (m, 2H), 3.3-3.6 (m, 2H), 3.45-3.49 (m, 1H), 7.61 (d, J=8.8 Hz, 1H), 7.74 (d, J=8.8 Hz, 2H), 7.81 (t, J=15.7 Hz, J=7.8 Hz, 1H), 7.93 (dd, J=8.8 Hz, J=2.5 Hz, 1H), 8.00 (d, J=7.6 Hz, 1H), 8.05 (d, J=8.9 Hz, 2H), 8.10 (d, J=2.5 Hz, 1H), 8.20-8.32 (m, 3H), 8.65-8.69 (m, 1H), 8.90 (s, 2H), 10.37 (s, 1H), 10.76 (s, 1H), 10.80 (s, 1H).

EXAMPLE 23

Synthesis of 2-Chloro-5-[(Thiophene-2-carbonyl)-Amino]-Benzoic Acid (Intermediate 15)

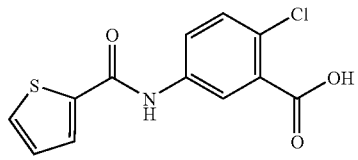

5-Amino-2-chloro-benzoic acid (0.349 g, 2.03 mmol) was diluted with THF (12 mL), treated with thiophene-2-carbonyl chloride (0.240 mL, 2.23 mmol) and stirred overnight. Solvents were then removed and resulting solids were triturated with DCM. After filtration, the title compound was obtained as a white solid (0.5 g, 88%).

EXAMPLE 24

Synthesis of 2-Chloro-5-(4-Cyano-Benzoylamino)-Benzoic Acid (Intermediate 16)

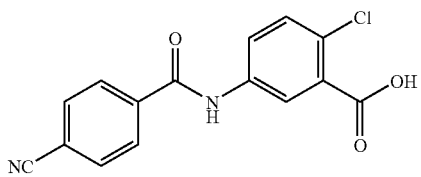

5-Amino-2-chloro-benzoic acid (0.355 g, 2.06 mmol) was diluted with THF (12 mL), treated with 4-cyano-benzoyl chloride (0.377 g, 2.23 mmol) and stirred for 72 h. Solvents were then removed and resulting solids were triturated with DCM. After filtration, the title compound was obtained as a white solid (0.6 g, 97%).

EXAMPLE 25

Synthesis of 2-Chloro-5-(4-Methoxy-Benzoylamino)-Benzoic acid (Intermediate 17)

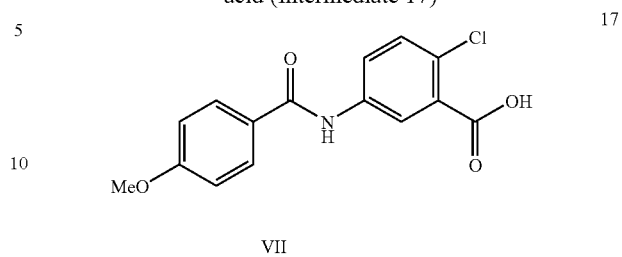

5-Amino-2-chloro-benzoic acid (0.4 g, 2.32 mmol) was diluted with THF (12 mL), treated with 4-methoxy-benzoyl chloride (0.353 g, 2.23 mmol) and stirred for 16 h. Solvents were then removed and resulting solids were triturated with DCM. After filtration, the title compound was obtained as a white solid (0.5 g, 71%).

EXAMPLE 26

Synthesis of 2-Chloro-5-(2-Fluoro-5-Trifluoromethyl-Benzoylamino)-Benzoic Acid (Intermediate 18)

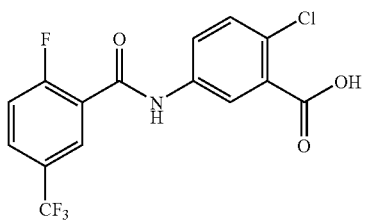

5-Amino-2-chloro-benzoic acid (0.4 g, 2.32 mmol) was diluted with THF (12 mL), treated with 2-fluoro-5-trifluoromethyl-benzoyl chloride (0.388 g, 2.56 mmol) and stirred for 16 h. Solvents were then removed and resulting solids were triturated with DCM. After filtration, the title compound was obtained as a white solid (0.5 g, 60%).

EXAMPLE 27

Synthesis of 2-Chloro-5-(3-Chloro-Benzoylamino)-Benzoic Acid (Intermediate 19)

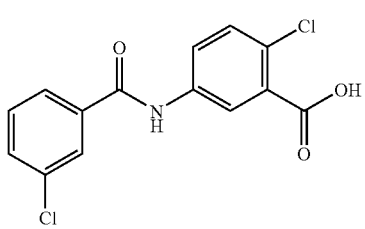

5-Amino-2-chloro-benzoic acid (0.4 g, 2.33 mmol) was diluted with THF (12 mL), treated with 3-chloro-benzoyl chloride (0.330 mL, 2.56 mmol) and stirred for 16 h. Solvents were then removed and resulting solids were triturated with DCM. After filtration, the title compound was obtained as a white solid (0.5 g, 70%).

EXAMPLE 28

Synthesis of 2-Chloro-5-(3-Fluoro-Benzoylamino)-Benzoic Acid (Intermediate 20)

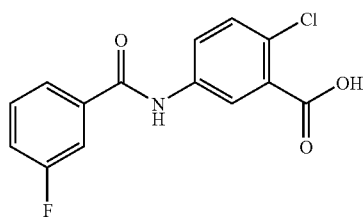

5-Amino-2-chloro-benzoic acid (0.96 g, 5.58 mmol) was diluted with THF (60 mL), treated with 3-fluoro-benzoyl chloride (0.738 mL, 6.14 mmol) and stirred for 18 h. Solvents were then removed and resulting solids were triturated with DCM. After filtration, the title compound was obtained as a white solid (1.7 g, 99%).

EXAMPLE 29

Synthesis of 5-Bromo-Pyridine-2-Carboxylic Acid (2-Pyrrolidin-1-yl-Ethyl)-Amide (Intermediate 21)

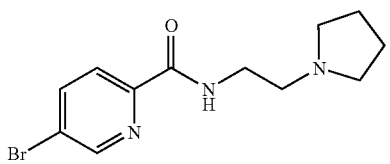

5-Bromo-pyridine-2-carboxylic acid (0.81 g, 4 mmol) was combined with 2-chloro-4,6-dimethoxy-1,3,5-triazine (CDMT) (0.85 g, 4.8 mmol) and diluted with DCM (20 mL). This was immediately treated with 4-methyl morpholine (0.81 g, 8 mmol) and allowed to stir at ambient temperature for 1 h. 2-Pyrrolidin-1-yl-ethylamine (0.46 g, 4 mmol) was then added in one portion. Stirring was continued overnight. Reaction solvents were removed and residue was taken up in ethyl acetate and washed once with water. Aqueous phase was back extracted once with fresh ethyl acetate. Organic phases were combined, washed once with brine and dried over sodium sulfate. Filtration followed by rotary evaporation provided product as yellow oil which solidified upon standing. Yellowish solids (0.5 g, 42%)

EXAMPLE 30

Synthesis of 5-(5-Nitro-Pyrimidin-2-ylamino)-Pyridine-2-Carboxylic Acid (2-Pyrrolidin-1-yl-Ethyl)-Amide (Intermediate 22)

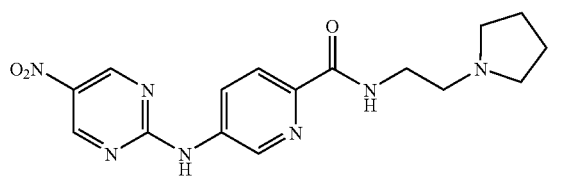

In a dry 50 mL round bottom flask 5-nitro-pyrimidin-2-ylamine (0.2 g, 1.36 mmol), intermediate 21 (Example 29) (0.61 g, 2.04 mmol), cesium carbonate (1.33 g, 4.08 mmol), 4,5-bis(diphenylphosphino)-9,9-dimethyl xanthene (0.157 g, 0.272 mmol) and tris(dibenzylideneacetone) dipalladium (0.124 g, 0.136 mmol) were combined. Reactants were flushed with argon, diluted with dioxane (8 mL) and outfitted with reflux condenser. Reaction was heated to reflux for 18 h. Reaction was then filtered hot and solvents were evaporated to provide dark solids. Silica gel chromatography (6:1 DCM/MeOH) provided desired product as a yellow powder (0.17 g, 33% yield). $R_f$=0.23 (10% MeOH/DCM)

EXAMPLE 31

Synthesis of 5-(5-Amino-Pyrimidin-2-ylamino)-Pyridine-2-Carboxylic Acid (2-Pyrrolidin-1-yl-Ethyl)-Amide (Intermediate 23)

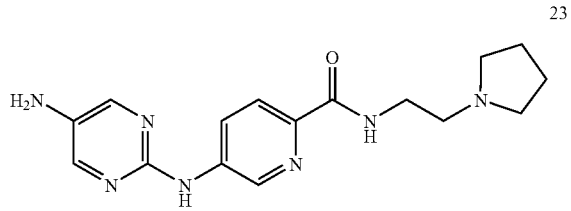

Intermediate 22 (Example 30) (0.17 g, 0.476 mmol) was combined with 10% palladium on carbon (0.14 g) and flushed with argon. Reactants were then diluted with methanol (15 mL) and reaction atmosphere was evacuated and replaced with hydrogen. Hydrogen balloon was affixed and reaction was allowed to stir for 2.5 h. Argon was then bubbled through reaction mixture and contents were filtered though a pad of CELITE. Solvents were evaporated to provide crude product. Titration with heptane followed by filtration provided desired amine as a beige solid (0.14 g, 90% yield). MS (ES+): m/z 328.1 (M+H)$^+$.

EXAMPLE 32

Synthesis of (5-Nitro-Pyrimidin-2-yl)-[4-(2-Pyrrolidin-1-yl-Ethoxy)-Phenyl]-Amine (Intermediate 24)

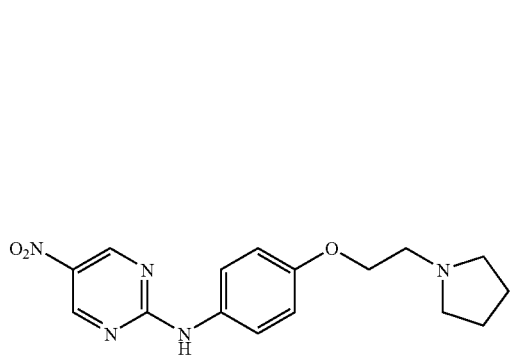

In a dry 100 mL round bottom flask 5-nitro-pyrimidin-2-ylamine (2 g, 14.3 mmol), 1-[2-(4-bromo-phenoxy)-ethyl]-pyrrolidine (4.45 mL, 21.4 mmol), cesium carbonate (14 g, 42.9 mmol), 4,5-bis(diphenylphosphino)-9,9-dimethyl xanthene (1.65 g, 1.43 mmol) and tris(dibenzylideneacetone)dipalladium (1.3 g, 0.714 mmol) were combined. Reactants were flushed with argon, diluted with dioxane (50 mL) and outfitted with reflux condenser. Reaction was heated to reflux for 18 h. Reaction was cooled to room temperature and filtered. Silica gel chromatography provided desired nitro product. As a yellow powder (1.5 g, 32% yield).

EXAMPLE 33

Synthesis of N-[4-(2-Pyrrolidin-1-yl-Ethoxy)-Phenyl]-Pyrimidine-2,5-Diamine (Intermediate 25)

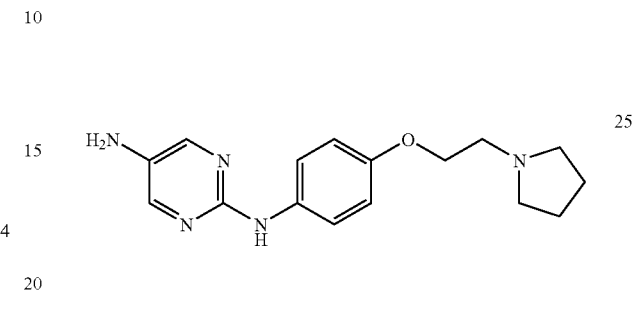

A methanolic solution of intermediate 24 (Example 32) (1.5 g, 6.48 mmol) was purged with argon for several minutes, then treated with 10% palladium on carbon (0.85 g). Reaction atmosphere was evacuated and replaced with hydrogen added via hydrogen-filled balloon. After 2 h, hydrogen balloon was removed and reaction solvents were purged with argon. CELITE was added to reaction solvent and resulting slurry was filtered through pad of CELITE. Solvents were then removed providing desired amine as a yellow solid (0.36 g, 26% yield).

EXAMPLE 34

Synthesis of 5-{5-[2-Methyl-5-(3-Trifluoromethyl-Benzoylamino)-Benzoylamino]-Pyrimidin-2-ylamino}-Pyridine-2-Carboxylic Acid (2-Pyrrolidin-1-yl-Ethyl)-Amide (Compound VIII)

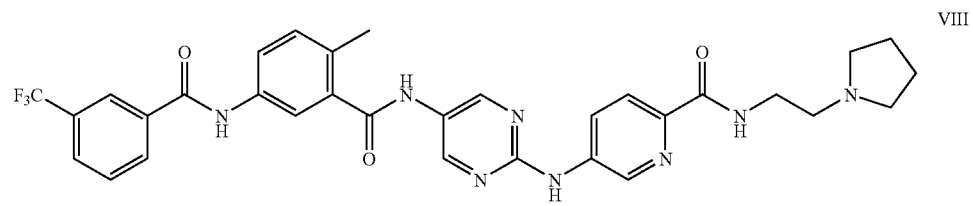

Intermediate 3 (Example 5) (0.070 g, 0.215 mmol) was combined with 2-chloro-4,6-dimethoxy-1,3,5-triazine (CDMT) (0.046 g, 0.26 mmol) and diluted with DCM (4 mL). This was immediately treated with 4-methyl morpholine (0.05 mL, 0.43 mmol) and allowed to stir at ambient temperature for 1 h. Intermediate 23 (Example 31) (0.074 g, 0.226 mmol) was then added in one portion. Stirring was continued overnight. After 18 h, reaction solvents were removed and resulting crude solids purified via HPLC to afford the title compound as a white solid (0.027 g, 20%).

$^1$H NMR (DMSO-$d_6$): δ 1.84-1.80 (m, 2H), 1.96-2.04 (m, 2H), 2.38 (s, 3H), 3.01-3.06 (m, 2H), 3.32-3.36 (m, 2H), 3.60-3.64 (m, 4H), 7.34 (d, J=8.5 Hz, 1H), 7.79-7.83 (m, 2H), 7.9-8.01 (m, 1H), 8.28 (d, J=8.7, 1H), 8.32 (s, 1H), 8.44 (dd, J=8.7 Hz, J=2.5 Hz, 1H), 8.91-8.97 (m, 4H), 9.46 (br s, 1H), 10.26 (s, 1H), 10.56 (s, 1H), 10.61 (s, 1H).

EXAMPLE 35

Synthesis of 5-{5-[2-Chloro-5-(3-Trifluoromethyl-Benzoylamino)-Benzoylamino]-Pyrimidin-2-ylamino}-Pyridine-2-Carboxylic Acid (2-Pyrrolidin-1-yl-Ethyl)-Amide (Compound IX)

Intermediate 1 (Example 2) (0.076 g, 0.222 mmol) was combined with 2-chloro-4,6-dimethoxy-1,3,5-triazine (CDMT) (0.047 g, 0.266 mmol) and diluted with DCM (4 mL). This was immediately treated with 4-methyl morpholine (0.05 mL, 0.443 mmol) and allowed to stir at ambient temperature for 1 h. Intermediate 23 (Example 31) (0.076 g, 0.233 mmol) was then added in one portion. Stirring was continued overnight. After 18 h, reaction solvents were removed and resulting crude solids purified via HPLC to afford the title compound as a white solid (0.081 g, 56%).

$^1$H NMR (DMSO-$d_6$): δ 1.84-1.80 (m, 2H), 1.96-2.04 (m, 2H), 3.02-3.08 (m, 2H), 3.33-3.37 (m, 2H), 3.61-3.65 (m, 4H), 7.61 (d, J=8.5 Hz, 1H), 7.81 (t, J=15.7 Hz, J=7.8 Hz, 1H), 7.93 (dd, J=8.7 Hz, J=2.5 Hz, 1H), 8.01 (d, J=8.7, 2H), 8.10 (d, J=2.5 Hz, 1H), 8.28 (d, J=8.0 Hz, 1H), 8.32 (s, 1H), 8.44 (dd, J=8.7 Hz, J=2.5 Hz, 1H), 8.90 (s, 2H), 8.93-8.97 (m, 2H), 9.46 (br s, 1H), 10.29 (s, 1H), 10.77 (s, 1H), 10.79 (s, 1H).

EXAMPLE 36

Synthesis of 2-Chloro-N-{2-[4-(Piperidine-4-Sulfonyl)-Phenylamino]-Pyrimidin-5-yl}-5-(3-Trifluoromethyl-Benzoylamino)-Benzamide (Compound X)

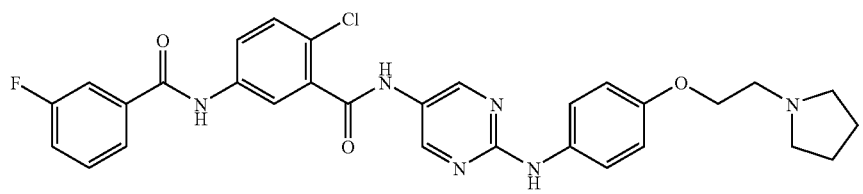

Intermediate 20 (Example 28) (0.247 g, 0.843 mmol) was combined with 2-chloro-4,6-dimethoxy-1,3,5-triazine (CDMT) (0.178 g, 1.01 mmol) and diluted with DCM (4 mL). This was immediately treated with 4-methyl morpholine (0.20 mL, 0.443 mmol) and allowed to stir at ambient temperature for 1 h. Intermediate 25 (Example 33) (0.265 g, 0.885 mmol) was then added in one portion. Stirring was continued overnight. After 18 h, reaction solvents were removed and resulting crude solids purified via HPLC to afford the title compound as a white solid (0.219 g, 45%).

$^1$H NMR (DMSO-$d_6$): δ 1.88-1.90 (m, 2H), 1.96-2.06 (m, 2H), 3.10-3.16 (m, 1H), 3.55-3.61 (m, 2H), 4.25 (t, J=4.8 Hz, 2H), 6.96 (d, J=9.0 Hz, 2H), 7.46-7.50 (m, 1H), 7.57-7.68 (m, 4H), 7.78-7.80 (m, 2H), 7.90 (dd, J=8.7 Hz, J=2.5 Hz, 1H), 8.08 (d, J=2.6 Hz, 1H), 8.73 (s, 2H), 9.55 (s, 1H), 9.85 (br s, 1H), 10.6 (s, 1H), 10.61 (s, 1H).

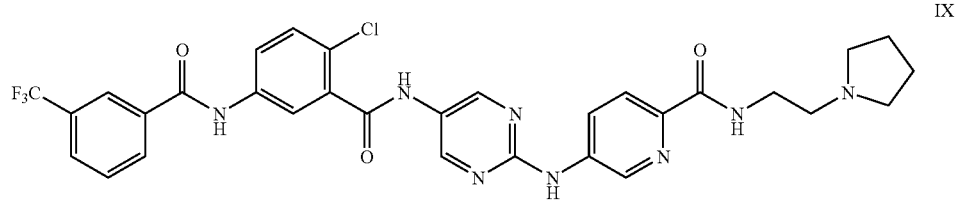

EXAMPLE 37

Synthesis of 4-[4-(5-{2-Chloro-5-[(Thiophene-2-Carbonyl)-Amino]-Benzoylamino}-Pyrimidin-2-ylamino)-Benzenesulfonyl]-Piperidine-1-Carboxylic Acid tert-Butyl Ester (Intermediate 26)

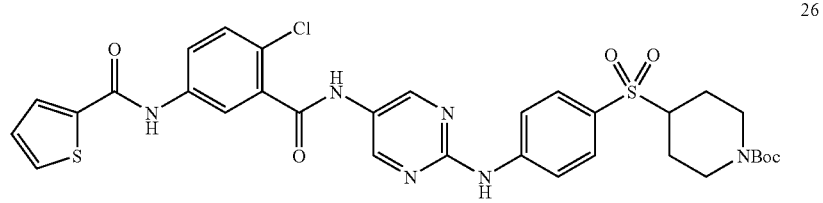

26

Intermediate 15 (Example 23) (0.124 g, 0.439 mmol) was combined with 2-chloro-4,6-dimethoxy-1,3,5-triazine (CDMT) (0.093 g, 0.53 mmol) and diluted with DCM (4 mL). This was immediately treated with 4-methyl morpholine (0.10 mL, 0.88 mmol) and allowed to stir at ambient temperature for 1 h. Intermediate 13 (Example 20) (0.20 g, 0.462 mmol) was then added in one portion. Stirring was continued overnight. After 18 h, reaction solvents were removed and resulting crude solids purified via HPLC to afford the title compound as a white solid (0.1 g, 32%).

EXAMPLE 38

Synthesis of Thiophene-2-Carboxylic Acid (4-Chloro-3-{2-[4-(Piperidine-4-Sulfonyl)-Phenylamino]-Pyrimidin-5-ylcarbamoyl}-Phenyl)-Amide (Compound XI)

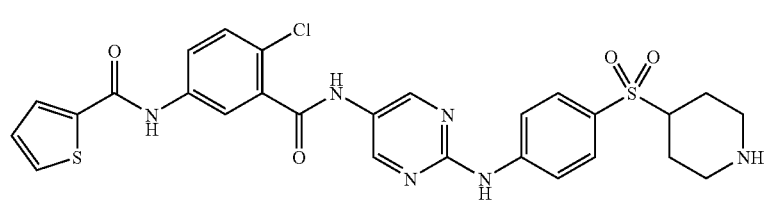

XI

A stirred suspension of intermediate 26 (Example 37) (0.10 g, 0.143 mmol) in DCM (8 mL) was treated with TFA (0.200 mL) and stirred for 3 h. Solvents were then removed yielding desired product as TFA salt (0.075 g, 87%). $^1$H NMR (DMSO-$d_6$): δ 1.61-1.70 (m, 2H), 2.01-2.04 (m, 2H), 2.80-2.90 (m, 2H), 7.23-7.27 (m, 1H), 7.58 (d, J=8.8 Hz, 1H), 7.74 (d, J=8.9 Hz, 2H), 7.86-7.91 (m, 2H), 8.04-8.05 (m, 4H), 8.21-8.25 (m, 1H), 8.65-8.69 (m, 1H), 8.9 (s, 2H), 10.37 (s, 1H), 10.53 (s, 1H), 10.79 (s, 1H).

EXAMPLE 39

Synthesis of 4-(4-{5-[2-Chloro-5-(4-Cyano-Benzoylamino)-Benzoylamino]-Pyrimidin-2-ylamino}-Benzenesulfonyl)-Piperidine-1-Carboxylic Acid tert-Butyl Ester (Intermediate 27)

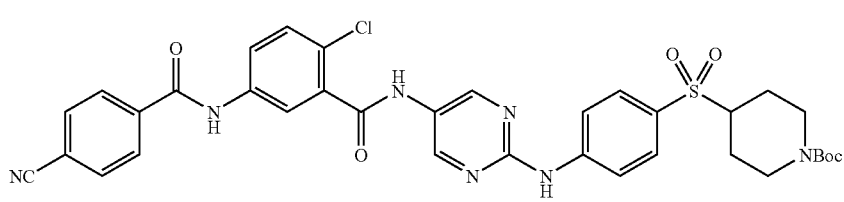

27

Intermediate 16 (Example 24) (0.132 g, 0.439 mmol) was combined with 2-chloro-4,6-dimethoxy-1,3,5-triazine (CDMT) (0.093 g, 0.53 mmol) and diluted with DCM (4 mL). This was immediately treated with 4-methyl morpholine (0.10 mL, 0.88 mmol) and allowed to stir at ambient temperature for 1 h. Intermediate 13 (Example 20) (0.20 g, 0.462 mmol) was then added in one portion. Stirring was continued overnight. After 18 h, reaction solvents were removed and resulting crude solids purified via HPLC to afford the title compound as a white solid (0.12 g, 36%).

EXAMPLE 40

Synthesis of 2-Chloro-5-(4-Cyano-Benzoylamino)-N-{2-[4-(Piperidine-4-Sulfonyl)-Phenylamino]-Pyrimidin-5-yl}-Benzamide (Compound XII)

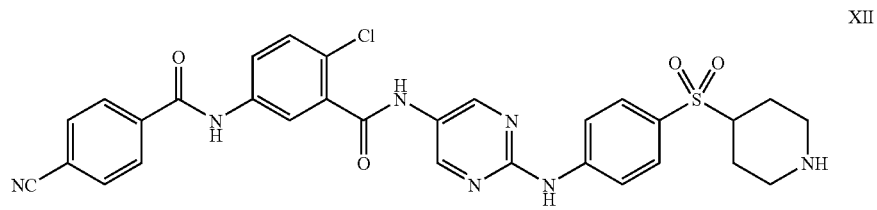

A stirred suspension of intermediate 27 (Example 39) (0.12 g, 0.143 mmol) in DCM (8 mL) was treated with TFA (0.200 mL) and stirred for 18 h. Solvents were then removed yielding desired product as TFA salt (0.104 g, 99%). $^1$H NMR (DMSO-d$_6$): δ 1.61-1.70 (m, 2H), 2.01-2.04 (m, 2H), 2.80-2.90 (m, 2H), 7.61 (d, J=8.8 Hz, 1H), 7.74 (d, J=8.9 Hz, 2H), 7.90 (dd, J=8.7 Hz, J=2.5 Hz, 1H), 8.04-8.13 (m, 7H), 8.21-8.25 (m, 1H), 8.64-8.68 (m, 1H), 8.90 (s, 2H), 10.37 (s, 1H), 10.78 (s, 1H), 10.80 (s, 1H).

EXAMPLE 41

Synthesis of 4-(4-{5-[2-Chloro-5-(4-Methoxy-Benzoylamino)-Benzoylamino]-Pyrimidin-2-ylamino}-Benzenesulfonyl)-Piperidine-1-Carboxylic Acid tert-Butyl Ester (Intermediate 28)

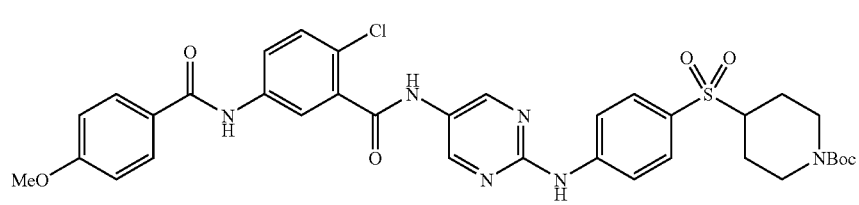

Intermediate 17 (Example 25) (0.134 g, 0.439 mmol) was combined with 2-chloro-4,6-dimethoxy-1,3,5-triazine (CDMT) (0.093 g, 0.53 mmol) and diluted with DCM (4 mL). This was immediately treated with 4-methyl morpholine (0.10 mL, 0.88 mmol) and allowed to stir at ambient temperature for 1 h. Intermediate 13 (Example 20) (0.20 g, 0.462 mmol) was then added in one portion. Stirring was continued overnight. After 18 h, reaction solvents were removed and resulting crude solids were used as-is for deprotection step. White solids (0.075 g, 24%).

EXAMPLE 42

Synthesis of 2-Chloro-5-(4-Methoxy-Benzoylamino)-N-{2-[4-(Piperidine-4-Sulfonyl)-Phenylamino]-Pyrimidin-5-yl}-Benzamide (Compound XIII)

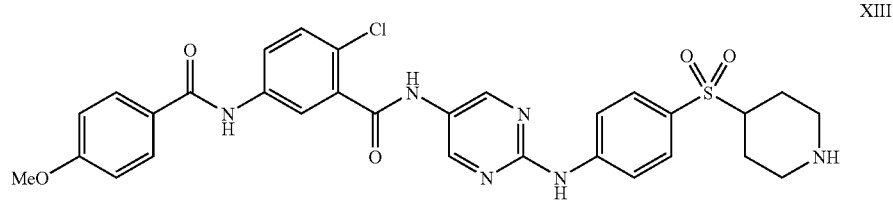

XIII

A stirred suspension of intermediate 28 (Example 41) (0.075 g, 0.104 mmol) in DCM (8 mL) was treated with TFA (0.200 mL) and stirred for 18 h. Solvents were then removed yielding desired product as TFA salt (0.064 g, 99%). $^1$H NMR (DMSO-d$_6$): δ 1.64-1.70 (m, 2H), 2.01-2.04 (m, 2H), 2.86-2.88 (m, 2H), 3.44-3.48 (m, 1H), 3.84 (s, 3H), 7.08 (d, J=8.8 Hz, 2H), 7.56 (d, J=8.9 Hz, 1H), 7.74 (d, J=8.8 Hz, 2H), 7.90 (dd, J=8.7 Hz, J=2.5 Hz, 1H), 7.98 (d, J=8.9 Hz, 2H), 8.05 (d, J=8.8 Hz, 2H), 8.23 (d, J=2.5 Hz, 1H), 8.24 (br s, 1H), 8.68 (br s, 1H), 8.90 (s, 2H), 10.37 (s, 1H), 10.39 (s, 1H), 10.78 (s, 1H).

EXAMPLE 43

Synthesis of 2-Chloro-N-{2-[4-(piperidine-4-sulfonyl)-phenylamino]-pyrimidin-5-yl}-5-(2-Fluoro-5-Trifluoromethyl-Benzoylamino)-Benzamide (Compound XIV)

XIV

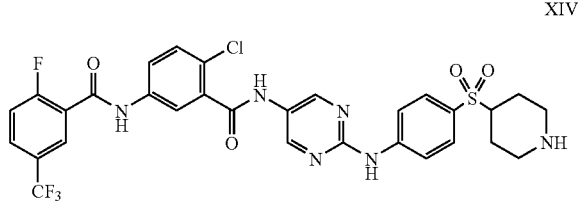

Intermediate 18 (Example 26) (0.159 g, 0.44 mmol) was combined with 2-chloro-4,6-dimethoxy-1,3,5-triazine (CDMT) (0.093 g, 0.53 mmol) and diluted with DCM (4 mL). This was immediately treated with 4-methyl morpholine (0.10 mL, 0.88 mmol) and allowed to stir at ambient temperature for 1 h. Intermediate 13 (Example 20) (0.20 g, 0.462 mmol) was then added in one portion. Stirring was continued overnight. After 18 h, reaction solvents were removed and resulting crude solids were diluted with DCM (4 mL) and treated with TFA (0.2 mL). After 2 h, reaction solvents were removed and resulting crude solids purified via HPLC to afford the title compound as a white solid (0.017 g, 6%).

$^1$H NMR (DMSO-d$_6$): δ 1.61-1.70 (m, 2H), 2.01-2.04 (m, 2H), 2.83-2.90 (m, 2H), 3.32-3.36 (m, 3H), 3.96 (s, 3H), 7.60-7.65 (m, 2H), 7.74 (d, J=8.9 Hz, 1H), 7.80 (dd, J=8.7 Hz, J=2.5 Hz, 1H), 8.03-8.10 (m, 5H), 8.22-8.26 (m, 1H), 8.66-8.70 (m, 1H), 8.90 (s, 2H), 10.37 (s, 1H), 10.80 (s, 1H), 10.93 (s, 1H).

EXAMPLE 44

Synthesis of 2-Chloro-5-(3-Chloro-Benzoylamino)-N-{2-[4-(Piperidine-4-Sulfonyl)-Phenylamino]-Pyrimidin-5-yl}-Benzamide (Compound XV)

XV

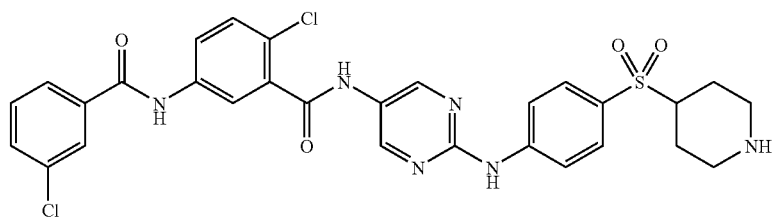

Intermediate 19 (Example 27) (0.136 g, 0.44 mmol) was combined with 2-chloro-4,6-dimethoxy-1,3,5-triazine (CDMT) (0.093 g, 0.53 mmol) and diluted with DCM (4 mL). This was immediately treated with 4-methyl morpholine (0.10 mL, 0.88 mmol) and allowed to stir at ambient temperature for 1 h. Intermediate 13 (Example 20) (0.20 g, 0.462 mmol) was then added in one portion. Stirring was continued overnight. After 18 h, reaction solvents were removed and resulting crude solids were diluted with DCM (4 mL) and treated with TFA (0.2 mL). After 2 h, reaction solvents were removed and resulting crude solids purified via HPLC to afford the title compound as a white solid (0.030 g, 11%).

$^1$H NMR (DMSO-$d_6$): δ 1.61-1.70 (m, 2H), 2.01-2.04 (m, 2H), 2.83-2.9 (m, 2H), 3.32-3.36 (m, 3H), 3.96 (s, 3H), 7.59-7.61 (m, 2H), 7.73-7.75 (m, 3H), 7.89-7.94 (m, 2H), 8.03-8.06 (m, 4H), 8.11 (d, J=2.5 Hz, 1H), 8.21-8.25 (m, 1H), 8.64-8.68 (m, 1H), 8.90 (s, 2H), 10.37 (s, 1H), 10.64 (s, 1H), 10.79 (s, 1H).

EXAMPLE 45

Synthesis of N$^2$-(3-(2-(Pyrrolidin-1-yl)Ethoxy)Phenyl)Pyrimidine-2,5-Diamine (Intermediate 29)

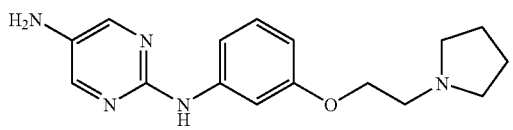

To a solution of the 2-amino-5-nitropyrimidine (200 mg, 1.4 mmol) in anhydrous 1,4-dioxane (20 mL) was added 1-(2-(3-bromophenoxy)ethyl)pyrrolidine (380 mg, 1.4 mmol), Cs$_2$CO$_3$ (1.82 g, 5.6 mmol), Pd$_2$(dba)$_3$ (128 mg, 0.14 mmol), and Xantphos (243 mg, 0.42 mmol). The suspension was heated under reflux for 2 h under Ar. The solid was filtered off and washed with EtOAc. The filtrate was washed once with brine (100 mL) and the aqueous phase was extracted with EtOAc (3×50 mL). Combined organic solution was dried (Na$_2$SO$_4$) and concentrated until 10 ml remain solution before adding hexane (100 mL). The mixture was sonicated for 2 min. The solid was collected by filtration and washed with hexane.

The crude material was further purified by flash column (SiO$_2$/CH$_2$Cl$_2$, then CH$_2$Cl$_2$:MeOH:NH$_3$.H$_2$O=100:10:1).

The resulting yellow solid was dissolved in MeOH (200 mL) and bubbled with argon for 2 min before adding 10% Pd—C. The mixture was hydrogenated for 1 h at room temperature. The catalyst was filtered off and washed with MeOH. The filtrate was concentrated in vacuo. The desired product was obtained as a yellow solid (350 mg, 83%).

EXAMPLE 46

Synthesis of 2-Methyl-N-{2-[3-(2-Pyrrolidin-1-yl-Ethoxy)-Phenylamino]-Pyrimidin-5-yl}-5-(3-Trifluoromethyl-Benzoylamino)-Benzamide (Compound XVI)

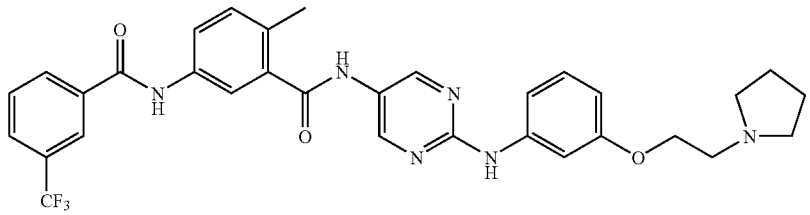

To a solution of intermediate 3 (Example 5) (233 mg, 0.72 mmol) in anhydrous CH$_2$Cl$_2$ (20 mL) was added 2-chloro-4,6-dimethyloxy-1,3,5-triazine (CDMT, 127 mg, 0.72 mmol), and 4-methylmopholine (NMM, 0.27 mL, 2.40 mmol). The mixture was stirred for 0.5 h at room temperature followed by adding intermediate 29 (Example 45) (180 mg, 0.60 mmol). The mixture was stirred overnight at room temperature. The saturated NaHCO$_3$ (40 mL) was added and the mixture was stirred for 5 min. The organic layer was separated and aqueous was extracted with CH$_2$Cl$_2$ (3×20 mL). The combined organic solution was dried (Na$_2$SO$_4$). The solvent was removed in vacuo.

The crude product was purified by using HPLC. The HPLC fractions containing product were combined and neutralized with saturated NaHCO$_3$ (50 mL). The free base was extracted with EtOAc (2×50 mL). The combined organic layer was dried (Na$_2$SO$_4$). The solvent was removed in vacuo. The free base was dissolved in MeOH (2 mL) and the 2.0 M solution of HCl (0.3 mL, 0.6 mmol) in Et$_2$O was added. The solution was stirred for 5 min at room temperature before removing solvent. The residue was dissolved in MeOH (1 mL) and anhydrous Et$_2$O (20 mL) was added. The solid was collected by centrifuging. The title compound (160 mg, 42%) was afforded as a yellow solid.

$^1$H NMR (500 MHz, DMSO-$d_6$): δ 1.87-190 (m, 2H), 1.99-2.03 (m, 2H), 2.38 (s, 3H), 3.09-3.14 (m, 2H), 3.56-3.60 (m, 4H), 4.33 (t, J=4.8 Hz, 2H), 6.59 (dd, J=8.0 Hz, J=1.9 Hz, 1H), 7.21 (t, J=8.1 Hz, 1H), 7.33 (d, J=8.4 Hz, 2H), 7.58-7.60 (m, 1H), 7.80 (t, J=7.8 Hz, 1H), 7.85 (dd, J=8.3 Hz, J=2.2 Hz, 1H), 7.97 (d, J=2.0 Hz, 1H), 7.99 (s, 1H), 8.31 (d, J=8.0 Hz, 1H), 8.34 (s, 1H), 8.83 (s, 2H), 9.70 (s, 1H), 10.48 (s, 1H), 10.66 (s, 1H), 10.76 (br s, 1H). MS (ES+): m/z 605.2 (M+H)$^+$.

EXAMPLE 47

Synthesis of 2-Chloro-N-{2-[3-(2-Pyrrolidin-1-yl-Ethoxy)-Phenylamino]-Pyrimidin-5-yl}-5-(3-Trifluoromethyl-Benzoylamino)-Benzamide (Compound XVII)

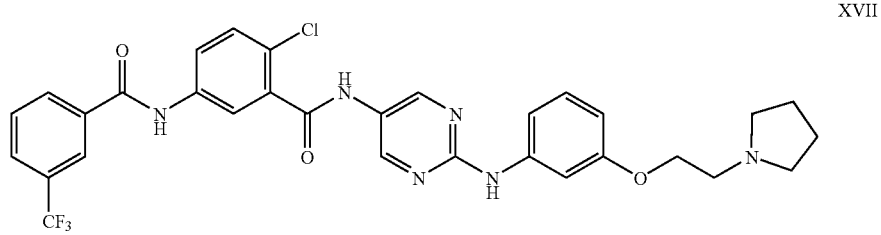

To a solution of intermediate 1 (Example 2) (234 mg, 0.68 mmol) in anhydrous $CH_2Cl_2$ (20 mL) was added 2-chloro-4,6-diimethyoxy-1,3,5-triazine (CDMT, 120 mg, 0.68 mmol), and 4-methylmopholine (NMM, 0.25 mL, 2.27 mmol). The mixture was stirred for 0.5 h at room temperature followed by adding intermediate 29 (Example 45) (170 mg, 0.57 mmol). The mixture was stirred overnight at room temperature. The saturated $NaHCO_3$ (40 mL) was added and the mixture was stirred for 5 min. The organic layer was separated and aqueous was extracted with $CH_2Cl_2$ (3×20 mL). The combined organic solution was dried ($Na_2SO_4$). The solvent was removed in vacuo.

The crude product was purified by using HPLC. The HPLC fractions containing product were combined and neutralized with saturated $NaHCO_3$ (50 mL). The free base was extracted with EtOAc (2×50 mL). The combined organic layer was dried ($Na_2SO_4$). The solvent was removed in vacuo. The free base was dissolved in MeOH (2 mL) and the 2.0 M solution of HCl (0.3 mL, 0.6 mmol) in $Et_2O$ was added. The solution was stirred for 5 min at room temperature before removing solvent. The residue was dissolved in MeOH (1 mL) and anhydrous $Et_2O$ (20 mL) was added. The solid was collected by centrifuging. The title compound (117 mg, 31%) was afforded as a yellow solid.

$^1H$ NMR (500 MHz, DMSO-$d_6$): δ 1.87-190 (m, 2H), 1.98-2.04 (m, 2H), 3.09-3.16 (m, 2H), 3.57-3.60 (m, 4H), 4.33 (t, J=4.8 Hz, 2H), 6.59 (dd, J=8.1 Hz, J=2.3 Hz, 1H), 7.21 (t, J=8.2 Hz, 1H), 7.32 (d, J=8.2 Hz, 1H), 7.58-7.60 (m, 1H), 7.61 (s, 1H), 7.81 (t, J=7.9 Hz, 1H), 7.96 (dd, J=8.9 Hz, J=2.6 Hz, 1H), 8.00 (d, J=7.8 Hz, 1H), 8.10 (s, 1H), 8.31 (d, J=8.0 Hz, 1H), 8.34 (s, 1H), 8.81 (s, 2H), 9.74 (s, 1H), 10.49 (br s, 1H), 10.71 (s, 1H), 10.82 (s, 1H). MS (ES+): m/z 625.1 $(M+H)^+$.

EXAMPLE 48

Synthesis of 5-(2,2,2-Trifluoroacetamido)-N-(2-(3-(2-(Pyrrolidin-1-yl)ethoxy)Phenylamino)-Pyrimidin-5-yl)-2-Chlorobenzamide (Compound XVIII)

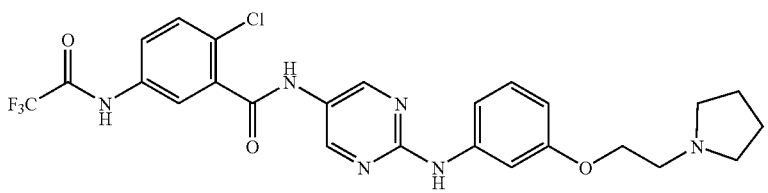

To a solution of 5-(2,2,2-trifluoroacetamido)-2-chlorobenzoic acid (128 mg, 0.48 mmol) in anhydrous $CH_2Cl_2$ (20 mL) was added 2-chloro-4,6-diimethyoxy-1,3,5-triazine (CDMT, 85 mg, 0.48 mmol), and 4-methylmopholine (NMM, 0.20 mL, 1.6 mmol). The mixture was stirred for 0.5 h at room temperature followed by adding intermediate 29 (Example 45) (120 mg, 0.40 mmol). The mixture was stirred overnight at room temperature. The saturated $NaHCO_3$ (40 mL) was added and the mixture was stirred for 5 min. The organic layer was separated and aqueous was extracted with $CH_2Cl_2$ (3×20 mL). The combined organic solution was dried ($Na_2SO_4$). The solvent was removed in vacuo.

The crude product was purified by using HPLC. The HPLC fractions containing product were combined and neutralized with saturated $NaHCO_3$ (50 mL). The free base was extracted with EtOAc (2×50 mL). The combined organic layer was dried ($Na_2SO_4$). The solvent was removed in vacuo. The free base was dissolved in MeOH (2 mL) and the solution of HCl (0.2 mL, 0.4 mmol) in Et$_2$O was added. The solution was stirred for 5 min at room temperature before removing solvent. The residue was dissolved in MeOH (1 mL) and anhydrous Et$_2$O (20 mL) was added. The solid was collected by centrifuging. The title compound was afforded as a yellow solid (5 mg, 2%).

$^1$H NMR (500 MHz, DMSO-d$_6$): δ 1.87-190 (m, 2H), 1.98-2.04 (m, 2H), 3.09-3.14 (m, 2H), 3.57-3.60 (m, 2H), 4.13 (t, J=5.2 Hz, 2H), 4.34 (t, J=4.9 Hz, 2H), 6.59 (dd, J=7.9 Hz, J=2.2 Hz, 1H), 7.21 (t, J=8.1 Hz, 1H), 7.34 (d, J=9.6 Hz, 1H), 7.56-7.57 (m, 1H), 7.64 (d, J=8.8 Hz, 1H), 7.84 (dd, J=8.8 Hz, J=2.6 Hz, 1H), 7.96 (d, J=2.5 Hz, 1H), 8.80 (s, 2H), 9.73 (s, 1H), 10.76 (s, 1H), 11.02 (br s, 1H), 11.71 (s, 1H). MS (ES+): m/z 549.1 (M+H)$^+$.

The crude product was purified by flash column (SiO$_2$/ CH$_2$Cl$_2$, then CH$_2$Cl$_2$:MeOH:NH$_3$.H$_2$O=100:10:1). The obtained yellow solid was dissolved in MeOH (200 mL) and bubbled with Ar for 2 min before adding 10% Pd—C. The mixture was hydrogenated for 1 h at room temperature. The catalyst was filtered off and washed with MeOH. The filtrate was concentrated in vacuo. The desired product was obtained as a yellow solid (1.36 g, 92%).

EXAMPLE 50

Synthesis of 5-(2,2,2-Trifluoroacetamido)-N-(2-(3-(2-(Pyrrolidin-1-yl)Ethoxy)Phenylamino)Pyrimidin-5-yl)-2-Methylbenzamide (Compound XIX)

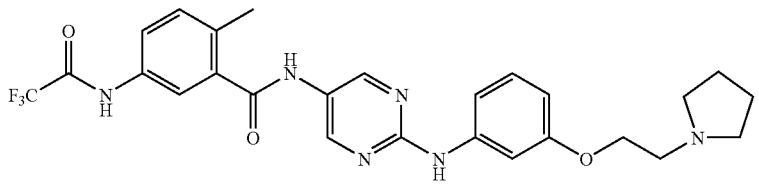

XIX

EXAMPLE 49

Synthesis of N-(2-(3-(2-(Pyrrolidin-1-yl)Ethoxy) Phenylamino)Pyrimidin-5-yl)-5-Amino-2-Methylbenzamide (Intermediate 30)

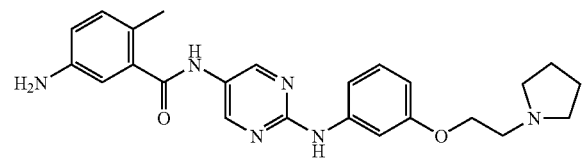

To a solution of 2-methyl-5-nitrobenzoic acid (0.93 g, 5.13 mmol) in anhydrous CH$_2$Cl$_2$ (50 mL) was added 2-chloro-4,6-diimethyoxy-1,3,5-triazine (CDMT, 0.9 g, 5.13 mmol), and 4-methylmopholine (NMM, 1.54 mL, 14 mmol). The mixture was stirred for 0.5 h at room temperature followed by adding intermediate 29 (Example 45) (1.02 g, 3.42 mmol). The mixture was stirred overnight at room temperature. The saturated NaHCO$_3$ (40 mL) was added and the mixture was stirred for 5 min. The organic layer was separated and aqueous was extracted with CH$_2$Cl$_2$ (3×20 mL). The combined organic solution was dried (Na$_2$SO$_4$). The solvent was removed in vacuo.

To a solution of intermediate 30 (Example 49) (140 mg, 0.32 mmol) in anhydrous CH$_2$Cl$_2$ (20 mL) was added trifluoroacetic anhydride (0.045 ml, 0.32 mmol). The mixture was stirred overnight at room temperature. The saturated NaHCO$_3$ (40 mL) was added and the mixture was stirred for 5 min. The organic layer was separated and aqueous was extracted with CH$_2$Cl$_2$ (3×20 mL). The combined organic solution was dried (Na$_2$SO$_4$). The solvent was removed in vacuo. The crude product was purified by using HPLC.

The HPLC fractions containing product were combined and neutralized with saturated NaHCO$_3$ (50 mL). The free base was extracted with EtOAc (2×50 mL). The combined organic layer was dried (Na$_2$SO$_4$). The solvent was removed in vacuo. The free base was dissolved in MeOH (2 mL) and the 2.0 M solution of HCl (0.2 mL, 0.4 mmol) in Et$_2$O was added. The solution was stirred for 5 min at room temperature before removing solvent. The residue was dissolved in MeOH (1 mL) and anhydrous Et$_2$O (20 mL) was added. The solid was collected by centrifuging. The title compound was afforded as a yellow solid (17.5 mg, 10%).

$^1$H NMR (500 MHz, DMSO-d$_6$): δ 1.87-190 (m, 2H), 1.98-2.04 (m, 2H), 2.38 (s, 3H), 3.09-3.14 (m, 2H), 3.56-3.60 (m, 4H), 4.33 (t, J=4.8 Hz, 2H), 6.59 (dd, J=8.2 Hz, J=2.2 Hz, 1H), 7.21 (t, J=8.1 Hz, 1H), 7.33 (d, J=8.3 Hz, 1H), 7.36 (d, J=8.4 Hz, 1H), 7.57 (s, 1H), 7.69 (dd, J=8.0 Hz, J=2.3 Hz, 1H), 7.83 (d, J=2.0 Hz, 1H), 8.81 (s, 2H), 9.70 (s, 1H), 10.48 (s, 1H), 10.74 (br s, 1H), 11.44 (s, 1H). MS (ES+): m/z 529.2 (M+H)$^+$.

EXAMPLE 51

Synthesis of 2,4,6-Trifluoro-N-(4-Methyl-3-{2-[3-(2-Pyrrolidin-1-yl-Ethoxy)-Phenylamino]-Pyrimidin-5-ylcarbamoyl}-Phenyl)-Benzamide (Compound XX)

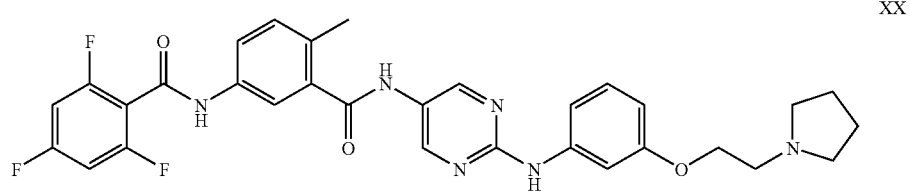

XX

To a solution of intermediate 30 (Example 49) (110 mg, 0.25 mmol) in anhydrous $CH_2Cl_2$ (20 mL) was added 2,4,6-trifluorobenzoyl chloride (50 mg, 0.25 mmol). The mixture was stirred overnight at room temperature. The saturated $NaHCO_3$ (40 mL) was added and the mixture was stirred for 5 min. The organic layer was separated and aqueous was extracted with $CH_2Cl_2$ (3×20 mL). The combined organic solution was dried ($Na_2SO_4$). The solvent was removed in vacuo. The crude product was purified by using HPLC.

The HPLC fractions containing product were combined and neutralized with saturated $NaHCO_3$ (50 mL). The free base was extracted with EtOAc (2×50 mL). The combined organic layer was dried ($Na_2SO_4$). The solvent was removed in vacuo. The free base was dissolved in MeOH (2 mL) and the 2.0 M solution of HCl (0.2 mL, 0.4 mmol) in $Et_2O$ was added. The solution was stirred for 5 min at room temperature before removing solvent. The residue was dissolved in MeOH (1 mL) and anhydrous $Et_2O$ (20 mL) was added. The solid was collected by centrifuging. The title compound was afforded as a yellow solid (8 mg, 5%).

$^1$H NMR (500 MHz, DMSO-$d_6$): δ 1.87-190 (m, 2H), 1.98-2.04 (m, 2H), 2.37 (s, 3H), 3.08-3.13 (m, 2H), 3.56-3.60 (m, 4H), 4.32 (t, J=4.7 Hz, 2H), 6.59 (dd, J=8.2 Hz, J=2.2 Hz, 1H), 7.21 (t, J=8.1 Hz, 1H), 7.32 (d, J=8.7 Hz, 2H), 7.38-7.41 (m, 2H), 7.58-7.59 (m, 1H), 7.64 (dd, J=8.3 Hz, J=2.2 Hz, 1H), 7.88 (d, J=2.1 Hz, 1H), 8.81 (s, 2H), 9.70 (s, 1H), 10.47 (s, 1H), 10.56 (br s, 1H), 10.97 (s, 1H). MS (ES+): m/z 591.3 $(M+H)^+$.

EXAMPLE 52

Synthesis of 2-Chloro-N-{2-[3-(2-pyrrolidin-1-yl-ethoxy)-phenylamino]-pyrimidin-5-yl}-4-(3-trifluoromethyl-benzoylamino)-benzamide (Compound XXI)

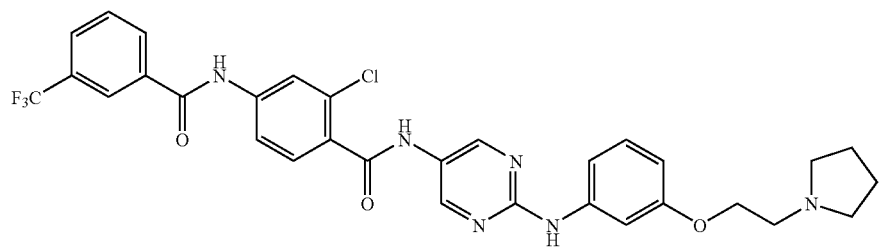

XXI

To a solution of 4-(3-(trifluoromethyl)benzamido)-2-chlorobenzoic acid (200 mg, 0.58 mmol) in anhydrous $CH_2Cl_2$ (20 mL) was added 2-chloro-4,6-diimethyoxy-1,3,5-triazine (CDMT, 102 mg, 0.58 mmol), and 4-methylmopholine (NMM, 0.17 mL, 1.52 mmol). The mixture was stirred for 0.5 h at room temperature followed by adding intermediate 29 (Example 45) (124 mg, 0.38 mmol). The mixture was stirred overnight at room temperature. The saturated $NaHCO_3$ (40 mL) was added and the mixture was stirred for 5 min. The organic layer was separated and aqueous was extracted with $CH_2Cl_2$ (3×20 mL). The combined organic solution was dried ($Na_2SO_4$). The solvent was removed in vacuo. The crude product was purified by using HPLC.

The HPLC fractions containing product were combined and neutralized with saturated $NaHCO_3$ (50 mL). The free base was extracted with EtOAc (2×50 mL). The combined organic layer was dried (Na$_2$SO$_4$). The solvent was removed in vacuo. The free base was dissolved in MeOH (2 mL) and the 2.0 M solution of HCl (0.3 mL, 0.6 mmol) in Et$_2$O was added. The solution was stirred for 5 min at room temperature before removing solvent. The residue was dissolved in MeOH (1 mL) and anhydrous Et$_2$O (20 mL) was added. The solid was collected by centrifuging. The title compound was afforded as a yellow solid (14 mg, 6%).

$^1$H NMR (500 MHz, DMSO-d$_6$): δ 1.87-190 (m, 2H), 1.98-2.04 (m, 2H), 3.09-3.16 (m, 2H), 3.57-3.60 (m, 4H), 4.33 (t, J=4.8 Hz, 2H), 6.59 (dd, J=8.1 Hz, J=2.3 Hz, 1H), 7.21 (t, J=8.2 Hz, 1H), 7.32 (d, J=8.2 Hz, 1H), 7.57 (s, 1H), 7.67 (d, J=8.2 Hz, 1H), 7.81 (t, J=7.6 Hz, 1H), 7.90 (d, J=7.6 Hz, 1H), 8.00 (d, J=7.6 Hz, 1H), 8.12 (d, J=1.2 Hz, 1H), 8.34-8.36 (m, 2H), 8.82 (s, 2H), 9.72 (s, 1H), 10.64 (s, 1H), 10.90 (br s, 1H), 10.94 (s, 1H). MS (ES+): m/z 625.1 (M+H)$^+$.

EXAMPLE 53

Synthesis of N-(3-(2-(3-(2-(Pyrrolidin-1-yl)Ethoxy)Phenylamino)Pyrimidin-5-ylamino)-4-methylphenyl)-3-(Trifluoromethyl)Benzamide (Compound XXII)

added. The solution was stirred for 5 min at room temperature before removing solvent. The residue was dissolved in MeOH (1 mL) and anhydrous Et$_2$O (20 mL) was added. The solid was collected by centrifuging. The title compound (11.3 mg, 6%) was afforded as a yellow solid.

$^1$H NMR (500 MHz, DMSO-d$_6$): δ 1.87-190 (m, 2H), 1.98-2.04 (m, 2H), 2.37 (s, 3H), 3.08-3.13 (m, 2H), 3.56-3.60 (m, 4H), 4.33 (t, J=4.7 Hz, 2H), 6.59 (dd, J=8.1 Hz, J=2.0 Hz, 1H), 7.21 (t, J=8.1 Hz, 1H), 7.29-7.33 (m, 2H), 7.52-7.62 (m, 5H), 7.81 (dd, J=8.3 Hz, J=2.2 Hz, 1H), 7.97-8.01 (m, 3H), 8.83 (s, 2H), 9.70 (s, 1H), 10.41 (s, 1H), 10.46 (s, 1H), 10.73 (br s, 1H). MS (ES+): m/z 537.2 (M+H)$^+$.

EXAMPLE 54

Synthesis of 1-(3-(2-(3-(2-(Pyrrolidin-1-yl)Ethoxy)Phenylamino)Pyrimidin-5-ylcarbamoyl)-4-Methylphenyl)-3-(3-(Trifluoromethyl)Phenyl)Urea (Compound XXIII)

XXII

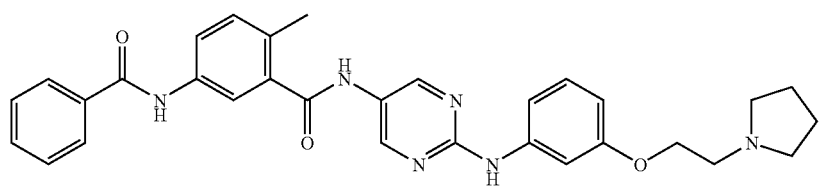

To a solution of intermediate 30 (Example 49) (154 mg, 0.36 mmol) in anhydrous CH2Cl2 (20 mL) was added ben-

XXIII

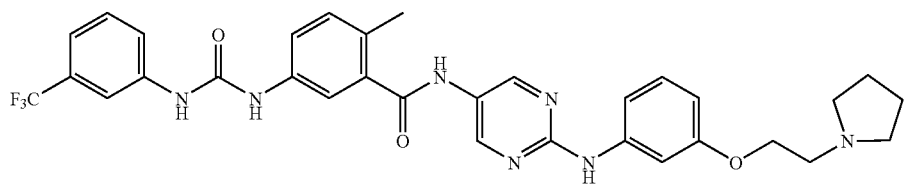

zoyl chloride (70.7 mg, 0.39 mmol). The mixture was stirred overnight at room temperature. The saturated NaHCO$_3$ (40 mL) was added and the mixture was stirred for 5 min. The organic layer was separated and aqueous was extracted with CH$_2$Cl$_2$ (3×20 mL). The combined organic solution was dried (Na$_2$SO$_4$). The solvent was removed in vacuo. The crude product was purified by using HPLC.

The HPLC fractions containing product were combined and neutralized with saturated NaHCO$_3$ (50 mL). The free base was extracted with EtOAc (2×50 mL). The combined organic layer was dried (Na$_2$SO$_4$). The solvent was removed in vacuo. The free base was dissolved in MeOH (2 mL) and the 2.0 M solution of HCl (0.2 mL, 0.4 mmol) in Et$_2$O was To a solution of intermediate 30 (Example 49) (234 mg, 0.54 mmol) in anhydrous CH$_2$Cl$_2$ (20 mL) was added 1-(trifluoromethyl)-3-isocyanatobenzene (113 mg, 0.60 mmol). The mixture was stirred for 2 h at room temperature. The saturated NaHCO$_3$ (40 mL) was added and the mixture was stirred for 5 min. The organic layer was separated and aqueous was extracted with CH$_2$Cl$_2$ (3×20 mL). The combined organic solution was dried (Na$_2$SO$_4$). The solvent was removed in vacuo. The crude product was purified by using HPLC.

The HPLC fractions containing product were combined and neutralized with saturated NaHCO$_3$ (50 mL). The free base was extracted with EtOAc (2×50 mL). The combined organic layer was dried (Na$_2$SO$_4$). The solvent was removed in vacuo. The free base was dissolved in MeOH (2 mL) and the 2.0 M solution of HCl (0.3 mL, 0.6 mmol) in Et₂O was added. The solution was stirred for 5 min at room temperature before removing solvent. The residue was dissolved in MeOH (1 mL) and anhydrous Et₂O (20 mL) was added. The solid was collected by centrifuging. The title compound XXIII (15 mg, 4%) was afforded as a yellow solid.

¹H NMR (500 MHz, DMSO-d₆): δ 1.87-191 (m, 2H), 1.98-2.04 (m, 2H), 2.33 (s, 3H), 3.08-3.14 (m, 2H), 3.56-3.60 (m, 4H), 4.31 (t, J=4.8 Hz, 2H), 6.59 (dd, J=8.1 Hz, J=2.3 Hz, 1H), 7.19-7.24 (m, 2H), 7.30 (d, J=7.9 Hz, 2H), 7.44 (dd, J=8.3 Hz, J=2.3 Hz, 1H), 7.51 (t, J=7.8 Hz, 1H), 7.57 (d, J=8.7 Hz, 1H), 7.62-7.63 (m, 1H), 7.67 (d, J=2.2 Hz, 1H), 8.02 (s, 1H), 8.82 (s, 2H), 9.43 (s, 1H), 9.70 (s, 1H), 9.71 (s, 1H), 10.29 (br s, 1H), 10.42 (s, 1H). MS (ES+): m/z 620.4 (M+H)⁺.

EXAMPLE 55

Synthesis of 2-Methyl-N-[2-(Pyridin-3-ylamino)-Pyrimidin-5-yl]-5-(3-trifluoromethyl-Benzoylamino)-Benzamide (Compound XXIV)

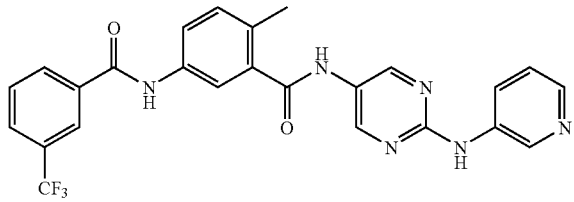

XXIV

To a solution of intermediate 3 (Example 5) (186.5 mg, 0.58 mmol) in anhydrous CH₂Cl₂ (20 mL) was added 2-chloro-4,6-diimethyoxy-1,3,5-triazine (CDMT, 101.3 mg, 0.58 mmol), and 4-methylmopholine (NMM, 0.21 mL, 1.9 mmol). The mixture was stirred for 0.5 h at room temperature followed by adding intermediate 9 (Example 15) (90 mg, 0.48 mmol). The mixture was stirred overnight at room temperature. The saturated NaHCO₃ (40 mL) was added and the mixture was stirred for 5 min. The organic layer was separated and aqueous was extracted with CH₂Cl₂ (3×20 mL). The combined organic solution was dried (Na₂SO₄). The solvent was removed in vacuo. The crude product was purified by using HPLC.

The HPLC fractions containing product were combined and neutralized with saturated NaHCO₃ (50 mL). The free base was extracted with EtOAc (2×50 mL). The combined organic layer was dried (Na₂SO₄). The solvent was removed in vacuo. The free base was dissolved in MeOH (2 mL) and the 2.0 M solution of HCl (0.25 mL, 0.5 mmol) in Et₂O was added. The solution was stirred for 5 min at room temperature before removing solvent. The residue was dissolved in MeOH (1 mL) and anhydrous Et₂O (20 mL) was added. The solid was collected by centrifuging. The title compound was afforded as a yellow solid (54.5 mg, 21%).

¹H NMR (500 MHz, DMSO-d₆): δ 2.39 (s, 3H), 7.34 (d, J=8.5 Hz, 1H), 7.80 (t, J=7.8 Hz, 1H), 7.84 (dd, J=8.3 Hz, J=2.3 Hz, 1H), 7.89-7.92 (m, 1H), 7.98 (s, 1H), 7.99 (d, J=2.1 Hz, 1H), 8.30 (d, J=8.0 Hz, 1H), 8.33 (s, 1H), 8.44 (d, J=5.2 Hz, 1H), 8.62 (dd, J=8.7 Hz, J=1.2 Hz, 1H), 8.98 (s, 2H), 9.32 (d, J=2.4 Hz, 1H), 10.63 (s, 1H), 10.65 (d, J=1.7 Hz, 1H). MS (ES+): m/z 493.1 (M+H)⁺.

EXAMPLE 56

Synthesis of 2-Chloro-N-[2-(Pyridin-3-ylamino)-Pyrimidin-5-yl]-5-(3-Trifluoromethyl-benzoylamino)-Benzamide (Compound XXV)

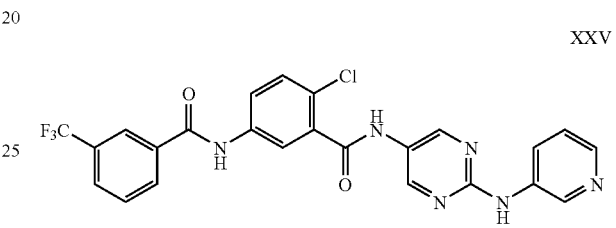

XXV

To a solution of intermediate 1 (Example 2) (463 mg, 1.34 mmol) in anhydrous CH₂Cl₂ (40 mL) was added 2-chloro-4,6-diimethyoxy-1,3,5-triazine (CDMT, 236 mg, 1.34 mmol), and 4-methylmopholine (NMM, 0.5 mL, 4.5 mmol). The mixture was stirred for 0.5 h at room temperature followed by adding intermediate 9 (Example 15) (210 mg, 1.12 mmol). The mixture was stirred overnight at room temperature. The saturated NaHCO₃ (80 mL) was added and the mixture was stirred for 5 min. The organic layer was separated and aqueous was extracted with CH₂Cl₂ (3×20 mL). The combined organic solution was dried (Na₂SO₄). The solvent was removed in vacuo. The crude product was purified by using HPLC.

The HPLC fractions containing product were combined and neutralized with saturated NaHCO₃ (50 mL). The free base was extracted with EtOAc (2×50 mL). The combined organic layer was dried (Na₂SO₄). The solvent was removed in vacuo. The free base was dissolved in MeOH (2 mL) and the 2.0 M solution of HCl (0.6 mL, 1.2 mmol) in Et₂O was added. The solution was stirred for 5 min at room temperature before removing solvent. The residue was dissolved in MeOH (1 mL) and anhydrous Et₂O (20 mL) was added. The solid was collected by centrifuging. The title compound was afforded as a yellow solid (65 mg, 11%).

¹H NMR (500 MHz, DMSO-d₆): δ 7.61 (d, J=8.8 Hz, 1H), 7.81 (t, J=7.8 Hz, 1H), 7.96-8.01 (m, 3H), 8.12 (d, J=2.5 Hz, 1H), 8.31 (d, J=8.0 Hz, 1H), 8.34 (s, 1H), 8.47 (d, J=5.2 Hz, 1H), 8.67 (d, J=7.1 Hz, 1H), 8.98 (s, 2H), 9.36 (s, 1H), 10.74 (s, 1H), 10.85 (s, 1H), 10.92 (s, 1H). MS (ES+): m/z 513.1 (M+H)⁺.

EXAMPLE 57

Synthesis of 5-Amino-2-Methyl-N-(2-(Pyridin-3-ylamino)Pyrimidin-5-yl)Benzamide (Intermediate 31)

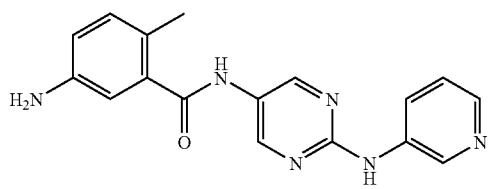

31

To a solution of 2-methyl-5-nitrobenzoic acid (1.05 g, 5.77 mmol) in anhydrous $CH_2Cl_2$ (50 mL) was added 2-chloro-4,6-dimethyoxy-1,3,5-triazine (CDMT, 0.9 g, 5.13 mmol), and 4-methylmopholine (NMM, 1.54 mL, 14 mmol). The mixture was stirred for 0.5 h at room temperature followed by adding intermediate 9 (Example 15) (0.9 g, 4.8 mmol). The mixture was stirred overnight at room temperature. The saturated $NaHCO_3$ (40 mL) was added and the mixture was stirred for 5 min. The organic layer was separated and aqueous was extracted with $CH_2Cl_2$ (3×20 mL). The combined organic solution was dried ($Na_2SO_4$). The solvent was removed in vacuo.

The crude product was purified by flash column ($SiO_2$/$CH_2Cl_2$, then $CH_2Cl_2$:MeOH:$NH_3 \cdot H_2O$=100:10:1). The obtained yellow solid was dissolved in MeOH (200 mL) and bubbled with Ar for 2 min before adding Raney Ni. The mixture was hydrogenated for 1 h at room temperature. The catalyst was filtered off and washed with MeOH. The filtrate was concentrated in vacuo. The desired product was obtained as a yellow solid (1.24 g, 81%).

EXAMPLE 58

Synthesis of 1-(3-(2-(Pyridin-3-ylamino)Pyrimidin-5-ylcarbamoyl)-4-Methylphenyl)-3-(3-(trifluoromethyl)Phenyl)Urea (Compound XXVI)

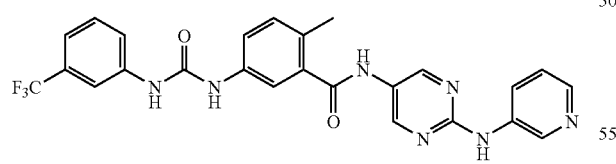

XXVI

To a solution of intermediate 31 (Example 57) (91 mg, 0.28 mmol) in anhydrous $CH_2Cl_2$ (20 mL) was added 1-(trifluoromethyl)-3-isocyanatobenzene (63.8 mg, 0.34 mmol). The mixture was stirred for 2 h at room temperature. The saturated $NaHCO_3$ (40 mL) was added and the mixture was stirred for 5 min. The organic layer was separated and aqueous was extracted with $CH_2Cl_2$ (3×20 mL). The combined organic solution was dried ($Na_2SO_4$). The solvent was removed in vacuo. The crude product was purified by using HPLC.

The HPLC fractions containing product were combined and neutralized with saturated $NaHCO_3$ (50 mL). The free base was extracted with EtOAc (2×50 mL). The combined organic layer was dried ($Na_2SO_4$). The solvent was removed in vacuo. The free base was dissolved in MeOH (2 mL) and the 2.0 M solution of HCl (0.3 mL, 0.6 mmol) in $Et_2O$ was added. The solution was stirred for 5 min at room temperature before removing solvent. The residue was dissolved in MeOH (1 mL) and anhydrous $Et_2O$ (20 mL) was added. The solid was collected by centrifuging. The title compound was afforded as a yellow solid (12 mg, 8%).

$^1$H NMR (500 MHz, DMSO-$d_6$): δ 2.33 (s, 3H), 7.24 (d, J=8.4 Hz, 1H), 7.29 (d, J=7.8 Hz, 1H), 7.45 (dd, J=8.3 Hz, J=2.3 Hz, 1H), 7.50 (t, J=7.9 Hz, 1H), 7.57 (d, J=8.9 Hz, 1H), 7.70 (d, J=2.2 Hz, 1H), 7.94-7.97 (m, 1H), 8.02 (s, 1H), 8.46 (d, J=5.3 Hz, 1H), 8.65 (d, J=7.4 Hz, 1H), 8.98 (s, 2H), 9.36 (s, 1H), 9.53 (s, 1H), 9.82 (s, 1H), 10.62 (br s, 1H), 10.68 (s, 1H). MS (ES+): m/z 508.1 (M+H)$^+$.

EXAMPLE 59

Synthesis of 2-Chloro-5-(3-(3-(Trifluoromethyl)Phenyl)ureido)Benzoic Acid (Intermediate 32)

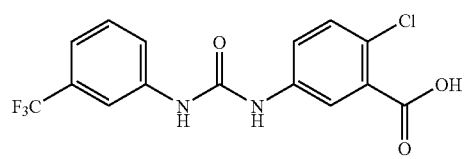

32

To a solution of 5-amino-2-chlorobenzoic acid (0.86 g, 5 mmol) in anhydrous $CH_2Cl_2$ (40 mL) was added 1-(trifluoromethyl)-3-isocyanatobenzene (1.03 g, 5.5 mmol). The mixture was stirred overnight at room temperature. The saturated $NaHCO_3$ (40 mL) was added and the mixture was stirred for 5 min. The organic layer was separated and aqueous was extracted with $CH_2Cl_2$ (3×20 mL). The combined organic solution was dried ($Na_2SO_4$). The solvent was removed in vacuo. The title compound was afforded as a white solid (1.68 g, 94%).

EXAMPLE 60

Synthesis of 1-(3-(2-(Pyridin-3-ylamino)pyrimidin-5-ylcarbamoyl)-4-chlorophenyl)-3-(3-(trifluoromethyl)phenyl)urea (Compound XXVII)

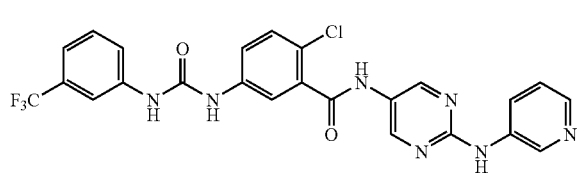

XXVII

To a solution of intermediate 32 (Example 59) (260 mg, 0.72 mmol) in anhydrous $CH_2Cl_2$ (20 mL) was added 2-chloro-4,6-diimethyoxy-1,3,5-triazine (CDMT, 127 mg, 0.72 mmol), and 4-methylmopholine (NMM, 0.29 mL, 2.64 mmol). The mixture was stirred for 0.5 h at room temperature followed by adding intermediate 9 (Example 15) (123.3 mg, 0.66 mmol). The mixture was stirred overnight at room temperature. The saturated NaHCO₃ (40 mL) was added and the mixture was stirred for 5 min. The organic layer was separated and aqueous was extracted with CH₂Cl₂ (3×20 mL). The combined organic solution was dried (Na₂SO₄). The solvent was removed in vacuo. The crude product was purified by using HPLC.

The HPLC fractions containing product were combined and neutralized with saturated NaHCO₃ (50 mL). The free base was extracted with EtOAc (2×50 mL). The combined organic layer was dried (Na₂SO₄). The solvent was removed in vacuo. The free base was dissolved in MeOH (2 mL) and the 2.0 M solution of HCl (0.35 mL, 0.7 mmol) in Et₂O was added. The solution was stirred for 5 min at room temperature before removing solvent. The residue was dissolved in MeOH (1 mL) and anhydrous Et₂O (20 mL) was added. The solid was collected by centrifuging. The title compound was afforded as a yellow solid (88 mg, 23%).

¹H NMR (500 MHz, DMSO-d₆): δ 7.31 (d, J=7.9 Hz, 1H), 7.47-7.57 (m, 4H), 7.81 (d, J=2.6 Hz, 1H), 7.99-8.01 (m, 2H), 8.48 (d, J=5.4 Hz, 1H), 8.67-8.69 (m, 1H), 8.97 (s, 2H), 9.39 (d, J=2.4 Hz, 1H), 9.82 (s, 1H), 9.86 (s, 1H), 10.76 (s, 1H), 10.86 (s, 1H). MS (ES+): m/z 528.0 (M+H)⁺.

EXAMPLE 61

Synthesis of 1-(3-(2-(4-(2-(Pyrrolidin-1-yl)Ethoxy) Phenylamino)Pyrimidin-5-ylcarbamoyl)-4-Chlorophenyl)-3-(3-(Trifluoromethyl)Phenyl)Urea (Compound XXVIII)

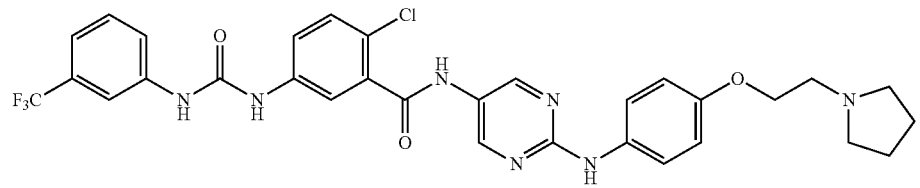

To a solution of intermediate 32 (Example 59) (153 mg, 0.43 mmol) in anhydrous CH₂Cl₂ (20 mL) was added 2-chloro-4,6-diimethyoxy-1,3,5-triazine (CDMT, 75.5 mg, 0.43 mmol), and 4-methylmopholine (NMM, 0.38 mL, 3.44 mmol). The mixture was stirred for 0.5 h at room temperature followed by adding intermediate 25 (Example 33) (120 mg, 0.36 mmol). The mixture was stirred overnight at room temperature. The saturated NaHCO₃ (40 mL) was added and the mixture was stirred for 5 min. The organic layer was separated and aqueous was extracted with CH₂Cl₂ (3×20 mL). The combined organic solution was dried (Na₂SO₄). The solvent was removed in vacuo. The crude product was purified by using HPLC.

The HPLC fractions containing product were combined and neutralized with saturated NaHCO₃ (50 mL). The free base was extracted with EtOAc (2×50 mL). The combined organic layer was dried (Na₂SO₄). The solvent was removed in vacuo. The free base was dissolved in MeOH (2 mL) and the 2.0 M solution of HCl (0.2 mL, 0.4 mmol) in Et₂O was added. The solution was stirred for 5 min at room temperature before removing solvent. The residue was dissolved in MeOH (1 mL) and anhydrous Et₂O (20 mL) was added. The solid was collected by centrifuging. The title compound was afforded as a yellow solid (38 mg, 16%).

¹H NMR (500 MHz, DMSO-d₆): δ 1.87-190 (m, 2H), 1.98-2.04 (m, 2H), 3.09-3.13 (m, 2H), 3.57-3.60 (m, 4H), 4.30 (t, J=4.9 Hz, 2H), 6.96 (d, J=9.0 Hz, 2H), 7.31 (d, J=8.2 Hz, 1H), 7.47-7.60 (m, 4H), 7.66 (d, J=9.0 Hz, 2H), 7.77 (d, J=2.5 Hz, 1H), 8.01 (s, 1H), 8.74 (s, 2H), 9.54 (s, 1H), 9.85 (s, 1H), 9.91 (s, 1H), 10.52 (br s, 1H), 10.58 (s, 1H). MS (ES+): m/z 640.2 (M+H)⁺.

EXAMPLE 62

Synthesis of N-(3-Bromo-4-Methylphenyl)-3-(Trifluoromethyl)Benzamide (Intermediate 33)

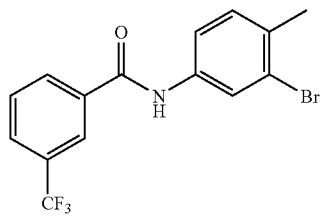

To a solution of 3-bromo-4-methylbenzenamine (0.82 g, 4.4 mmol) in anhydrous CH₂Cl₂ (40 mL) was added 3-(trifluoromethyl)benzoyl chloride (0.72 ml, 4.85 mmol) and triethylamine (2.5 ml, 17.6 mmol). The mixture was stirred overnight at room temperature. The saturated NaHCO₃ (80 mL) was added and the mixture was stirred for 5 min. The organic layer was separated and aqueous was extracted with CH₂Cl₂ (3×20 mL). The combined organic solution was dried (Na₂SO₄). The solvent was removed in vacuo. The title compound was afforded as a yellow solid (1.48 g, 94%).

EXAMPLE 63

Synthesis of N-(3-(2-(3-(2-(Pyrrolidin-1-yl)Ethoxy) Phenylamino)Pyrimidin-5-ylamino)-4-Methylphenyl)-3-(Trifluoromethyl)Benzamide (Compound XXIX)

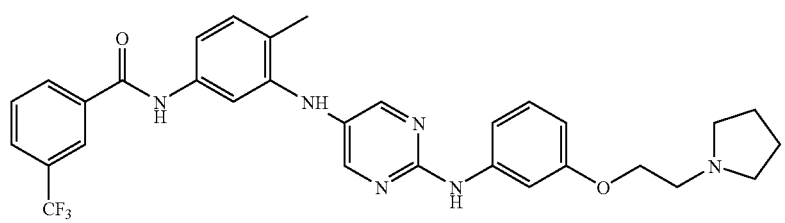

XXIX

To a solution of intermediate 33 (Example 62) (191 mg, 0.53 mmol) in anhydrous 1,4-dioxane (30 mL) were added intermediate 29 (Example 45) (160 mg, 0.53 mmol), $Cs_2CO_3$ (700 mg, 2.13 mmol), $Pd_2(dba)_3$ (50 mg, 0.05 mmol), and Xantphos (93 mg, 0.16 mmol). The suspension was heated under reflux for 4 h under argon. The solid was filtered off and washed with EtOAc. The filtrate was washed with brine (1×100 mL) and the aqueous was extracted with EtOAc (3×50 mL). Combined organic solution was dried ($Na_2SO_4$) and concentrated until 10 ml remain solution before adding hexane (100 mL). The mixture was sonicated for 2 min. The solid was collected by filtration and washed with hexane. The crude product was purified by using HPLC.

The HPLC fractions containing product were combined and neutralized with saturated $NaHCO_3$ (50 mL). The free base was extracted with EtOAc (2×50 mL). The combined organic layer was dried ($Na_2SO_4$). The solvent was removed in vacuo. The free base was dissolved in MeOH (2 mL) and the 2.0 M solution of HCl (0.3 mL, 0.6 mmol) in $Et_2O$ was added. The solution was stirred for 5 min at room temperature before removing solvent. The residue was dissolved in MeOH (1 mL) and anhydrous $Et_2O$ (20 mL) was added. The solid was collected by centrifuging. The title compound was afforded as a yellow solid (118 mg, 36%).

$^1$H NMR (500 MHz, DMSO-$d_6$): δ 1.86-189 (m, 2H), 1.97-2.03 (m, 2H), 2.23 (s, 3H), 3.07-3.11 (m, 2H), 3.56-3.59 (m, 4H), 4.31 (t, J=4.8 Hz, 2H), 6.56 (dd, J=8.2 Hz, J=2.3 Hz, 1H), 7.10 (d, J=8.3 Hz, 1H), 7.20 (t, J=8.2 Hz, 1H), 7.26 (dd, J=8.1 Hz, J=1.9 Hz, 1H), 7.35 (dd, J=6.1 Hz, J=1.6 Hz, 2H), 7.55 (t, J=2.2 Hz, 1H), 7.74 (t, J=7.7 Hz, 1H), 7.92 (d, J=7.8 Hz, 1H), 8.20 (s, 1H), 8.21 (s, 1H), 8.38 (s, 2H), 9.54 (s, 1H), 10.28 (s, 1H), 10.55 (br s, 1H). MS (ES+): m/z 577.3 (M+H)$^+$.

EXAMPLE 64

Synthesis of N-(2-(3-(2-(Pyrrolidin-1-yl)Ethoxy) Phenylamino)Pyrimidin-5-yl)-5-(Isoquinolin-1-ylamino)-2-Methylbenzamide (Compound XXX)

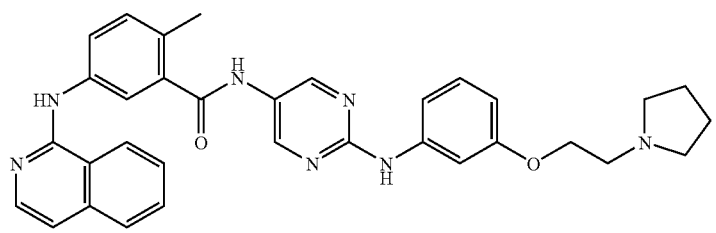

XXX

To a solution of intermediate 30 (Example 49) (116 mg, 0.27 mmol) in anhydrous 1,4-dioxane (30 mL) were added 1-chloroisoquinoline (48 mg, 0.30 mmol), $Cs_2CO_3$ (365 mg, 1.12 mmol), $Pd_2(dba)_3$ (26 mg, 0.027 mmol), and Xantphos (49 mg, 0.084 mmol). The suspension was heated under reflux for 4 h under Ar. The solid was filtered off and washed with EtOAc. The filtrate was washed with brine (1×100 mL) and the aqueous was extracted with EtOAc (3×50 mL). Combined organic solution was dried ($Na_2SO_4$) and concentrated until 10 ml remain solution before adding hexane (100 mL). The mixture was sonicated for 2 min. The solid was collected by filtration and washed with hexane. The crude product was purified by using HPLC.

The HPLC fractions containing product were combined and solvent was removed in vacuo. The residue was dissolved in MeOH (1 mL) and anhydrous $Et_2O$ (20 mL) was added. The solid was collected by centrifuging. The title compound was afforded as a yellow solid (8.6 mg, 5%).

$^1$H NMR (500 MHz, DMSO-$d_6$): δ 1.86-190 (m, 2H), 2.01-2.05 (m, 2H), 2.47 (s, 3H), 3.12-3.17 (m, 2H), 3.58-3.63

(m, 4H), 4.27 (t, J=4.6 Hz, 2H), 6.59 (dd, J=8.3 Hz, J=2.4 Hz, 1H), 7.22 (t, J=8.2 Hz, 1H), 7.34 (d, J=8.1 Hz, 1H), 7.47 (br s, 1H), 7.57 (s, 1H), 7.73 (br s, 2H), 7.82-7.87 (m, 2H), 7.99 (br s, 2H), 8.69 (d, J=7.6 Hz, 1H), 8.81 (s, 2H), 9.71 (s, 1H), 9.73 (br s, 1H), 10.40 (s, 1H). MS (ES+): m/z 560.3 (M+H)+.

EXAMPLE 65

Synthesis of N-(2-(3-(2-(Pyrrolidin-1-yl)Ethoxy) Phenylamino)Pyrimidin-5-yl)-5-Bromo-2-Chlorobenzamide (Intermediate 34)

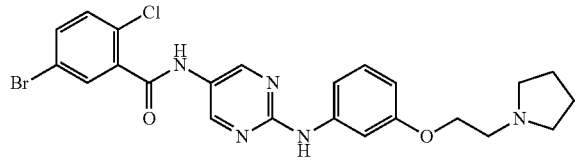

To a solution of 5-bromo-2-chlorobenzoic acid (86 mg, 0.36 mmol) in anhydrous CH$_2$Cl$_2$ (20 mL) was added 2-chloro-4,6-diimethyoxy-1,3,5-triazine (CDMT, 64 mg, 0.36 mmol), and 4-methylmopholine (NMM, 0.15 mL, 1.32 mmol). The mixture was stirred for 0.5 h at room temperature followed by adding intermediate 29 (Example 45) (106 mg, 0.33 mmol). The mixture was stirred overnight at room temperature. The saturated NaHCO$_3$ (40 mL) was added and the mixture was stirred for 5 min. The organic layer was separated and aqueous was extracted with CH$_2$Cl$_2$ (3×20 mL). The combined organic solution was dried (Na$_2$SO$_4$). The solvent was removed in vacuo. The crude product was used for next step without further purification.

EXAMPLE 66

Synthesis of N-(2-(3-(2-(Pyrrolidin-1-yl)ethoxy) Phenylamino)Pyrimidin-5-yl)-2-Chloro-5-(Pyridin-2-ylamino)Benzamide (Compound XXXI)

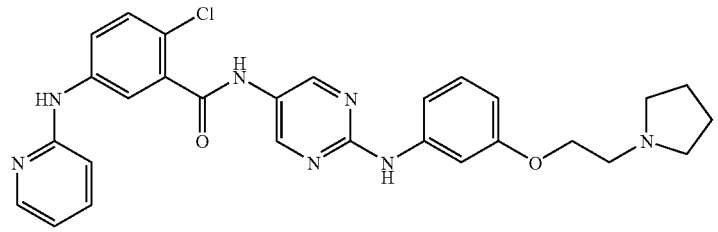

To a solution of intermediate 34 (Example 65) (0.33 mmol) in anhydrous 1,4-dioxane (30 mL) were added 2-aminopyridine (37.3 mg, 0.40 mmol), Cs$_2$CO$_3$ (430 mg, 1.32 mmol), Pd$_2$(dba)$_3$ (30.2 mg, 0.033 mmol), and Xantphos (58 mg, 0.10 mmol). The suspension was heated under reflux for 4 h under argon. The solid was filtered off and washed with EtOAc. The filtrate was washed with brine (1×100 mL) and the aqueous was extracted with EtOAc (3×50 mL). Combined organic solution was dried (Na$_2$SO$_4$) and concentrated until 10 ml remain solution before adding hexane (100 mL). The mixture was sonicated for 2 min. The solid was collected by filtration and washed with hexane. The crude product was purified by using HPLC.

The HPLC fractions containing product were combined and neutralized with saturated NaHCO$_3$ (50 mL). The free base was extracted with EtOAc (2×50 mL). The combined organic layer was dried (Na$_2$SO$_4$). The solvent was removed in vacuo. The free base was dissolved in MeOH (2 mL) and the 2.0 M solution of HCl (0.2 mL, 0.4 mmol) in Et$_2$O was added. The solution was stirred for 5 min at room temperature before removing solvent. The residue was dissolved in MeOH (1 mL) and anhydrous Et$_2$O (20 mL) was added. The solid was collected by centrifuging. The title compound was afforded as a yellow solid (31.6 mg, 17%).

$^1$H NMR (500 MHz, DMSO-d$_6$): δ 1.86-190 (m, 2H), 2.01-2.05 (m, 2H), 2.47 (s, 3H), 3.12-3.17 (m, 2H), 3.58-3.63 (m, 4H), 4.27 (t, J=4.6 Hz, 2H), 6.59 (dd, J=8.0 Hz, J=2.3 Hz, 1H), 6.93 (t, J=6.2 Hz, 1H), 7.08 (d, J=8.2 Hz, 1H), 7.22 (t, J=8.2 Hz, 1H), 7.31 (d, J=8.0 Hz, 1H), 7.53 (d, J=8.7 Hz, 1H), 7.59 (t, J=2.1 Hz, 1H), 7.70 (d, J=6.5 Hz, 1H), 7.80 (br s, 1H), 7.95 (d, J=2.5 Hz, 1H), 8.16 (d, J=6.5 Hz, 1H), 8.84 (s, 2H), 9.73 (s, 1H), 10.49 (br s, 1H), 10.80 (s, 1H). MS (ES+): m/z 530.2 (M+H)+.

EXAMPLE 67

Synthesis of 4-Bromo-N-(2-Pyrrolidin-1-yl-Ethyl)-Benzamide (Intermediate 35)

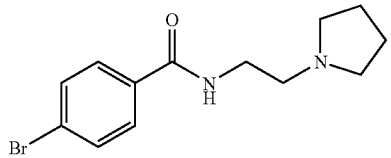

To 4-bromobenzoic acid (5 g, 24.8 mmol) in dichloromethane (125 mL) was added thionyl chloride (18.15 mL, 248.7 mmol) followed by DMF (1 mL). The reaction mixture was heated under reflux for 5 h till no gas evolution observed. The volatiles were evaporated under reduced pressure, and the residue was taken in hexane-ethyl acetate (200 mL, 3:1). The slurry was filtered through a small plug of silica gel and evaporated. The crude chloride was obtained as a yellow syrup, that eventually becomes solid (4.47 g, 82%). To the acid chloride (2.0 g, 9.11 mmol) in dichloromethane (50 mL) was added triethylamine (6.35 mL, 45.55 mmol) and pyrrolidine ethyl amine (1.15 mL, 9.11 mmol) at 0° C. and warmed to room temperature.

After stirring at room temperature for 16 h, the reaction mixture was quenched with saturated aqueous sodium bicarbonate (30 mL). The organic layer was separated, and the aqueous layer was extracted again with dichloromethane (100 mL). The combined organic phase was separated, dried (MgSO$_4$), filtered through a silica plug, and the volatiles were removed under reduced pressure, to give a white solid (2.4 g, 89%).

EXAMPLE 68

Synthesis of 4-(5-Amino-Pyrimidin-2-ylamino)-N-(2-Pyrrolidin-1-yl-Ethyl)-Benzamide (Intermediate 36)

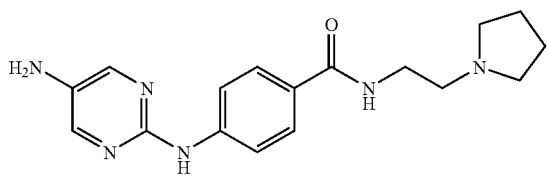

A mixture of 2-amino-5-nitropyrimidine (140 mg, 1.0 mmol), 44 (297 mg, 1.0 mmol), Pd$_2$(dba)$_3$ (9.0 mg, 0.01 mmol), Xantphos (12 mg, 0.02 mmol) and cesium carbonate (650 mg, 2.0 mmol) were suspended in dioxane (15 mL) and heated at reflux under the argon atmosphere for 15 h. The solvent evaporated and the residue triturated with chloroform-water-brine (50 mL, 1:1:1). The chloroform layer was separated, dried, and evaporated. The residue (400 mg) was taken in methanol (50 mL) and was hydrogenated over Pd/C (10%, 120 mg) for 3 hr. The catalyst was removed by filtration, and the solvent evaporated. The residue was crystallized using chloroform-methanol mixture to give the title compound (344 mg, quant) as yellow solid.

EXAMPLE 69

Synthesis of 2-Chloro-N-{2-[4-(2-Pyrrolidin-1-yl-Ethylcarbamoyl)-Phenylamino]-Pyrimidin-5-yl}-5-(3-Trifluoromethyl-Benzoylamino)-Benzamide (Compound XXXII)

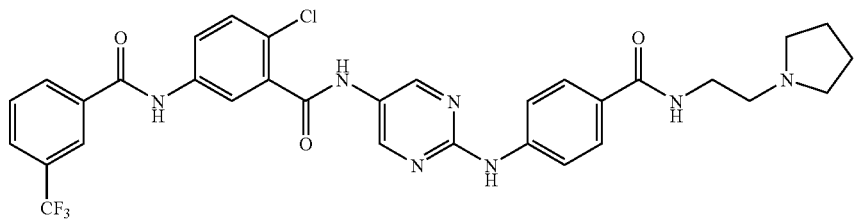

A solution of intermediate 1 (Example 2) (52.3 mg, 0.15 mmol) in DCM (2 mL) was charged with oxalyl chloride (30 µL, 0.35 mmol) and DMF (1 drop, cat.). The solution was stirred until clear (about 15 min.) and concentrated in vacuo. The resulting white solid was taken up in THF (4 mL) and charged with intermediate 36 (Example 68) (56.9 mg, 0.18 mmol), and TEA (0.1 mL, 0.71 mmol). The reaction mixture was stirred for 16 h and concentrated in vacuo. The crude mixture was purified by HPLC to afford the TFA salt of the title compound as a white solid (4.5 mg, 4%).

$^1$H NMR (500 MHz, DMSO-d$_6$): δ 1.85-1.89 (m, 2H), 1.98-2.07 (m, 2H), 3.02-3.11 (m, 4H), 3.58 (q, J=5.9 Hz, 2H), 3.62-3.68 (m, 2H), 7.62 (d, J=8.8 Hz, 1H), 7.80-7.83 (m, 3H), 7.87 (d, J=9.0 Hz, 2H), 7.93 (dd, J=8.8, 2.5 Hz, 1H), 8.01 (d, J=7.7 Hz, 1H), 8.09 (d, J=2.6 Hz, 1H), 8.28 (d, J=7.8 Hz, 1H), 8.32 (s, 1H), 8.52 (t, J=5.8 Hz, 1H), 8.86 (s, 2H), 9.33 (br s, 1H), 10.04 (s, 1H), 10.73 (s, 1H), 10.74 (s, 1H). MS (ES+): m/z 652.1 (M+H)$^+$.

EXAMPLE 70

Synthesis of 2-Methyl-N-{2-[4-(2-Pyrrolidin-1-yl-Ethylcarbamoyl)-Phenylamino]-Pyrimidin-5-yl}-5-(3-Trifluoromethyl-Benzoylamino)-Benzamide (Compound XXXIII)

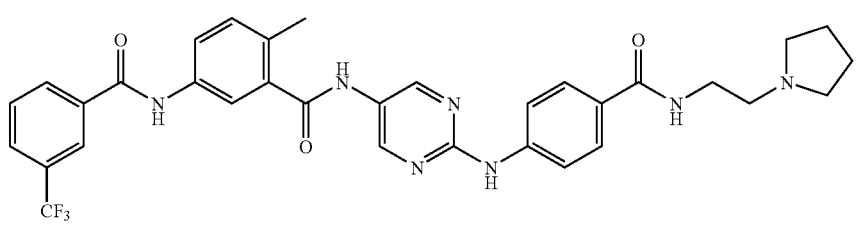

A solution of intermediate 3 (Example 5) (52.4 mg, 0.15 mmol) in DCM (1.5 mL) was charged with oxalyl chloride (21 µL, 0.25 mmol) and DMF (1 drop, cat.). The solution was stirred for 1 hr and concentrated in vacuo. The resulting white solid was taken up in anhydrous THF (1.5 mL) and charged with intermediate 36 (Example 68) (50.8 mg, 0.16 mmol), and TEA (65 µL, 0.46 mmol). The reaction mixture was stirred for 16 h and concentrated in vacuo. The crude mixture was purified by HPLC to afford the TFA salt of the title compound as a white solid (16.2 mg, 14%).

¹H NMR (500 MHz, DMSO-d₆): δ 1.85-1.89 (m, 2H), 2.01-2.07 (m, 2H), 2.39 (s, 3H), 3.05-3.11 (m, 2H), 3.58 (q, J=5.9 Hz, 2H), 3.62-3.68 (m, 2H), 7.34 (d, J=8.5 Hz, 1H), 7.79-7.88 (m, 6H), 7.97 (d, J=2.2 Hz, 1H), 7.99 (d, J=8.0 Hz, 1H), 8.29 (d, J=7.9 Hz, 1H), 8.32 (s, 1H), 8.53 (t, J=5.6 Hz, 1H), 8.87 (s, 2H), 9.43 (br s, 1H), 10.01 (s, 1H), 10.50 (s, 1H), 10.59 (s, 1H). MS (ES+): m/z 632.5 (M+H)⁺.

EXAMPLE 71

Synthesis of 2-Chloro-5-(Cyclohexanecarboxamido)Benzoic Acid (Intermediate 37)

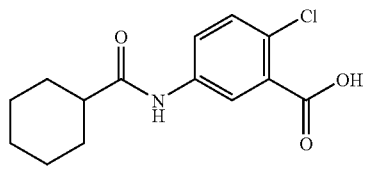

37

A solution of 5-amino-2-chlorobenzoic acid (0.34 g, 2.0 mmol) in THF (10 mL) was charged with cyclohexanecarbonyl chloride (0.27 mL, 1.7 mmol). The reaction was stirred for 16 h and then concentrated in vacuo. The residue was suspended in DCM and filtered to afford the title compounds as a white solid (0.47 g, 97%).

¹H NMR (500 MHz, DMSO-d₆): δ 1.16-1.30 (m, 3H), 1.39 (qd, J=12.2 Hz, J=2.5 Hz, 2H), 1.64 (br d, J=12.0 Hz, 1H), 1.65-1.81 (m, 4H), 2.31 (tt, J=11.6 Hz, J=3.4 Hz, 1H), 7.44 (d, J=8.8 Hz, 1H), 7.76 (dd, J=8.8 Hz, J=2.6 Hz, 1H), 8.11 (d, J=2.6 Hz, 1H), 10.08 (s, 1H), 13.40 (br s, 1H). MS (ES+): m/z 282.1 (M+H)⁺.

EXAMPLE 72

Synthesis of N-(2-(4-(2-(Pyrrolidin-1-yl)Ethoxy) Phenylamino)Pyrimidin-5-yl)-2-Chloro-5-(Cyclohexanecarboxamido)Benzamide (Compound XXXIV)

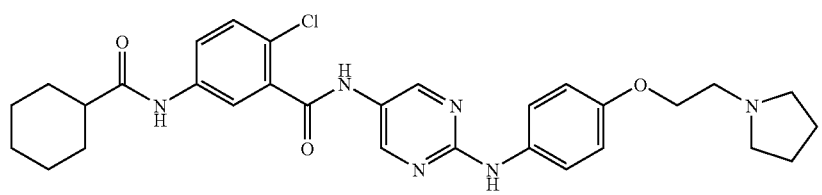

XXXIV

A solution of Intermediate 37 (Example 71) (160 mg, 0.57 mmol) in DMF was charged with HOBT (124 mg, 0.91 mmol), HBTU (365 mg, 0.96 mmol), DIEA (0.4 mL, 2.3 mmol), and intermediate 25 (Example 33) (185.9 mg, 0.55 mmol) and allowed to stir for 16 h. The mixture was concentrated and purified by HPLC. The aqueous HPLC fractions (approx. 120 mL) were extracted with NaHCO₃ (aq) (10 mL) and EtOAc (200 mL). The organic layer was washed with brine (20 mL), dried (Na₂SO₄), and concentrated in vacuo. The freebase was taken up in DCM and excess HCL in Et₂O was added and the solution concentrated in vacuo to yield the HCl salt of the title compound as a yellow solid (81 mg, 25%).

¹H NMR (500 MHz, DMSO-d₆): δ 1.14-1.31 (m, 3H), 1.37-1.47 (m, 2H), 1.61-1.68 (m, 1H), 1.72-1.83 (m, 4H), 1.86-1.94 (m, 2H), 1.97-2.06 (m, 2H), 2.31-2.38 (m, 1H), 3.05-3.14 (m, 2H), 3.54-3.61 (m, 5H), 4.29 (t, J=5.1 Hz, 2H), 6.96 (d, J=9.2 Hz, 2H), 7.48 (d, J=8.8 Hz, 1H), 7.64-7.68 (m, 3H), 7.95 (d, J=2.6 Hz, 1H), 8.72 (s, 2H), 9.53 (s, 1H), 10.19 (s, 1H), 10.38 (br s, 1H), 10.54 (s, 1H). MS (ES+): m/z 563.3 (M+H)⁺.

EXAMPLE 73

Synthesis of N-(2-Amino-Pyrimidin-5-yl)-2-Chloro-5-(3-Trifluoromethyl-Benzoylamino)-Benzamide (Compound XXXV)

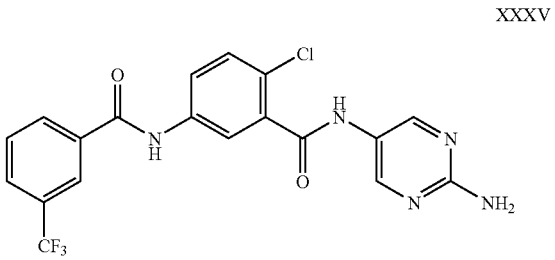

XXXV

A solution of intermediate 1 (Example 2) (380 mg, 1.11 mmol) in DCM was charged with CDMT (233 mg, 1.33 mmol), and NMM (0.3 mL, 2.73 mmol). After 1 hr of stirring, 2,5-diaminopyrimidine (121 mg, 1.10 mmol) was added and the solution was allowed to stir for 48 h. The mixture was concentrated and purified by HPLC to afford the title compound as a white solid (350 mg, 73%).

¹H NMR (500 MHz, DMSO-d₆): δ 7.59 (d, J=8.8 Hz, 1H), 7.81 (t, J=7.9 Hz, 1H), 7.93 (dd, J=8.8 Hz, J=2.5 Hz, 1H), 8.00 (d, J=7.8 Hz, 1H), 8.02 (d, J=2.7 Hz, 1H), 8.28 (d, J=8.0 Hz, 1H), 8.32 (s, 1H), 8.54 (s, 2H), 10.45 (s, 1H), 10.71 (s, 1H). MS (ES+): m/z 436.0 (M+H)⁺.

EXAMPLE 74

Synthesis of 2-Chloro-N-[2-(2-Pyrrolidin-1-yl-Ethylamino)-Pyrimidin-5-yl]-5-(3-Trifluoromethyl-benzoylamino)-Benzamide (Compound XXXVI)

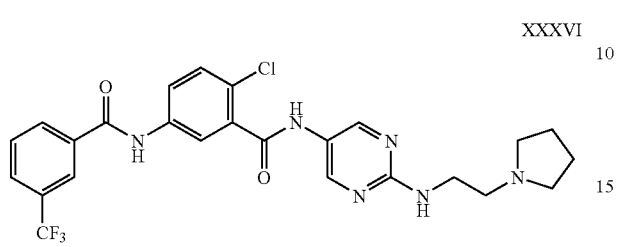

XXXVI

A suspension of compound XXXV (Example 73) (100 mg, 0.23 mmol), 1-(2-chloroethyl)pyrrolidine hydrochloride (45 mg, 0.27 mmol), and K$_2$CO$_3$ (95 mg, 0.69 mmol) in 4 mL DMF were sealed in a microwave reaction tube and irradiated at 190° C. for 7 min. After cooling to room temperature, the cap was removed and the resulting mixture poured into water. The resulting precipitate was filtered, taken up in DMF and purified by HPLC to afford the TFA salt of the title compound as a tan solid (10 mg, 7%).

$^1$H NMR (500 MHz, DMSO-d$_6$): δ 1.85-1.89 (m, 2H), 2.01-2.07 (m, 2H), 3.05-3.11 (m, 2H), 3.62-3.68 (m, 2H), 4.08 (br s, 2H), 6.84 (s, 2H), 7.35 (d, J=8.8 Hz, 1H), 7.53 (dd, J=8.8 Hz, J=2.5 Hz, 1H), 7.80 (t, J=7.8 Hz, 1H), 8.00 (d, J=7.8 Hz, 1H), 8.04 (d, J=2.6 Hz, 1H), 8.18 (s, 2H), 8.25 (d, J=7.8 Hz, 1H), 8.32 (s, 1H), 9.68 (br s, 1H), 10.63 (s, 1H). MS (ES+): m/z 533.1 (M+H)$^+$.

EXAMPLE 75

Synthesis of 3-Bromo-N-(2-Pyrrolidin-1-yl-ethyl)-Benzenesulfonamide (Intermediate 38)

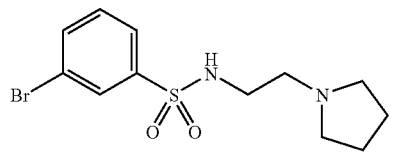

38

A solution of 3-bromobenzene-1-sulfonyl chloride (1.29 g, 5.05 mmol) in 25 mL THF was charged with 2-(pyrrolidin-1-yl)ethanamine (0.6 mL, 5.05 mmol), and TEA (2.2 mL, 15.7 mmol) and allowed to stir for 1 hr. The reaction was quenched with 25 mL NaHCO$_3$ (sat., aq.) and extracted with DCM (2×100 mL). The combined organic layers were washed with brine (20 mL), dried (Na$_2$SO$_4$), filtered, and concentrated. The residue was purified by gradient flash chromatography (0 to 20% MeOH in DCM) to afford the title compound as a white solid (816 mg, 48%).

$^1$H NMR (500 MHz, DMSO-d$_6$): δ 1.55-1.63 (m, 4H), 2.30-2.34 (m, 4H), 2.39 (t, J=6.8 Hz, 2H), 2.88 (t, J=6.7 Hz, 2H), 7.55 (t, J=7.9 Hz, 1H), 7.80 (ddd, J=7.9, J=1.8, J=0.8 Hz, 1H), 7.85 (ddd, J=7.9 Hz, J=1.8 Hz, J=0.8 Hz, 1H), 7.95 (t, J=1.8 Hz, 1H). MS (ES+): m/z 332.9 (M+H)$^+$.

EXAMPLE 76

Synthesis of 2-Chloro-N-{2-[3-(2-Pyrrolidin-1-yl-Ethylsulfamoyl)-Phenylamino]-Pyrimidin-5-yl}-5-(3-Trifluoromethyl-Benzoylamino)-Benzamide (Compound XXXVII)

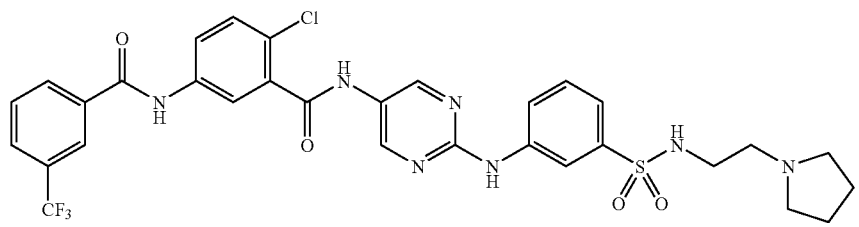

XXXVII

A suspension of compound XXXV (Example 73) (100 mg, 0.23 mmol), intermediate 38 (Example 75) (80 mg, 0.24 mmol), Pd(OAc)$_2$ (5.6 mg, 0.025 mmol), Xantphos (30.8 mg, 0.053 mmol) and potassium tert-butoxide (54 mg, 0.48 mmol) in 4 mL dioxane was sealed in a microwave reaction tube and irradiated at 160° C. for 15 min. After cooling to room temperature, the mixture was filtered and the filtrate concentrated. The resulting residue was purified by HPLC to afford the TFA salt of the title compound as a white solid (57 mg, 31%).

$^1$H NMR (500 MHz, DMSO-d$_6$): δ 1.84-1.91 (m, 2H), 1.97-2.04 (m, 2H), 2.95-3.11 (m, 4H), 3.23-3.26 (m, 2H), 3.52-3.59 (m, 2H), 7.38 (d, J=8.0 Hz, 1H), 7.54 (t, J=8.1 Hz, 1H), 7.62 (d, J=8.8 Hz, 1H), 7.82 (t, J=7.8 Hz, 1H), 7.91-8.02 (m, 4H), 8.10 (d, J=2.6 Hz, 1H), 8.28 (d, J=7.9 Hz, 1H), 8.32 (s, 1H), 8.41 (t, J=1.9 Hz, 1H), 8.86 (s, 2H), 9.50 (br s, 1H), 10.11 (s, 1H), 10.74 (s, 1H), 10.75 (s, 1H). MS (ES+): m/z 688.1 (M+H)$^+$.

EXAMPLE 77

Synthesis of 5-(4-(Trifluoromethyl)benzamido)-2-Chlorobenzoic acid (Intermediate 39)

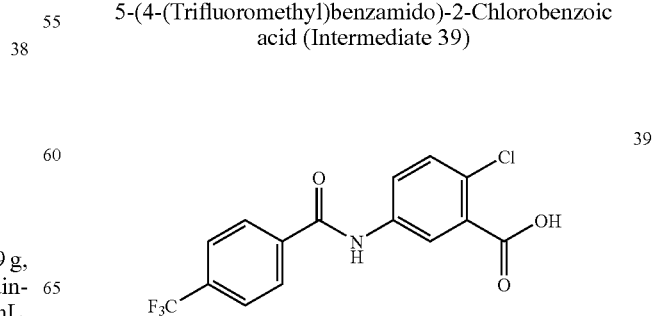

39

To a suspension of 4-(trifluoromethyl)benzoic acid (1.0 g, 5.3 mmol) in DCM (20 mL) were added CDMT (1.1 g, 6.3 mmol) and NMM (2.3 mL, 21 mmol). The mixture was stirred at RT for 30 min under an argon atmosphere. 5-amino-2-chlorobenzoic acid (1.4 g, 7.9 mmol) was added and the mixture stirred at RT for additional 2 h. The reaction mixture was poured into saturated $NaHCO_3$ solution and then extracted with DCM. The organic layer was dried ($Na_2SO_4$), filtered and the filtrate concentrated to afford the title compound (1.6 g, 88%) as a cream solid.

EXAMPLE 78

Synthesis of 2-Chloro-N-{2-[4-(2-Pyrrolidin-1-yl-Ethoxy)-Phenylamino]-Pyrimidin-5-yl}-5-(4-Trifluoromethyl-Benzoylamino)-Benzamide (Compound XXXVIII)

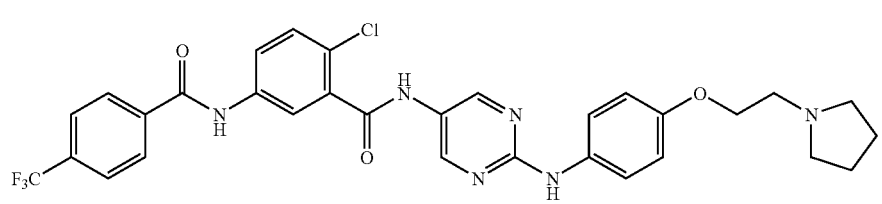

XXXVIII

A solution of intermediate 39 (Example 77) (110 mg, 0.32 mmol) in DCM was charged with CDMT (62 mg, 0.35 mmol), and NMM (0.1 mL, 0.91 mmol). After 20 min. of stirring, intermediate 25 (Example 33) (125 mg, 0.37 mmol) was added and the solution was allowed to stir for 4 days. The mixture was concentrated and purified by HPLC. The resulting product was eventually coaxed to crystalline form via ethyl ether trituration to afford the title compound as a tan solid (10 mg, 4%).

$^1$H NMR (500 MHz, DMSO-$d_6$): δ 1.84-1.91 (m, 2H), 1.97-2.05 (m, 2H), 3.07-3.16 (m, 2H), 3.54-3.64 (m, 4H), 4.26 (t, J=5.0 Hz, 2H), 6.97 (d, J=9.1 Hz, 2H), 7.60 (d, J=8.8 Hz, 1H), 7.67 (d, J=9.1 Hz, 2H), 7.91 (dd, J=8.8 Hz, J=2.5 Hz, 1H), 7.95 (d, J=8.5 Hz, 2H), 8.09 (d, J=2.6 Hz, 1H), 8.17 (d, J=8.0 Hz, 2H), 8.74 (s, 2H), 9.55 (s, 1H), 9.80 (br s, 1H), 10.60 (s, 1H), 10.76 (s, 1H). MS (ES+): m/z 625.1 (M+H)$^+$.

EXAMPLE 79

Synthesis of 2-Methyl-N-{2-[4-(2-Pyrrolidin-1-yl-Ethoxy)-Phenylamino]-Pyrimidin-5-yl}-5-(3-Trifluoromethyl-Benzoylamino)-Benzamide (Compound XXXIX)

A mixture of intermediates 3 (Example 5) (316 mg, 0.978 mmol), 25 (Example 33) (195 mg, 0.652 mmol) and DIPEA (340 μL, 1.96 mmol) was dissolved in DMF (7 mL) and treated with HBTU (395 mg, 1.043 mmol) and HOBt (132 mg, 0.978 mmol) at room temperature for 16 h. The reaction mixture was extracted was triturated with ethyl acetate-water-brine (30 mL, 1:1:1). The organic layer was separated, dried ($Na_2SO_4$) and evaporated. The residue was purified to give title compound as a pale yellow solid (144 mg, 24%).

$^1$H NMR (500 MHz, DMSO-$d_6$): δ 1.65-1.75 (m, 4H), 2.37 (s, 3H), 2.6-2.9 (m, 4H), 2.9-3.1 (m, 2H), 4.05-4.2 (m, 2H), 6.89 (d, J=9.1 Hz, 2H), 7.31 (d, J=9.1 Hz, 2H), 7.62 (d, J=9.0 Hz, 2H), 7.79 (t, J=8.3 Hz, 1H), 7.87 (dd, J=2.5 Hz, J=8.0 Hz, 1H), 7.92-8.0 (m, 2H), 8.31-8.38 (m, 2H), 8.76 (s, 2H), 9.45 (s, 1H), 10.43 (s, 1H), 10.76 (s, 1H). MS (ES+): m/z 605.36 (M+H)$^+$.

XXXIX

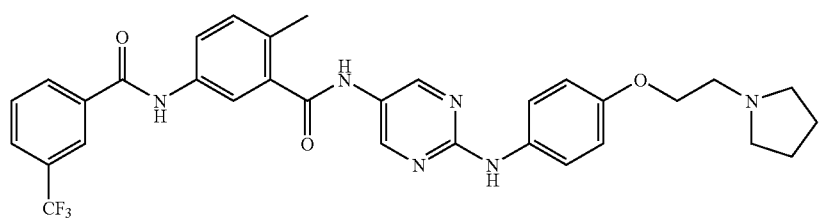

EXAMPLE 80

Synthesis of 2-Chloro-N-{2-[4-(2-Pyrrolidin-1-yl-ethoxy)-Phenylamino]-Pyrimidin-5-yl}-5-(3-Trifluoromethyl-Benzoylamino)-Benzamide (Compound XL)

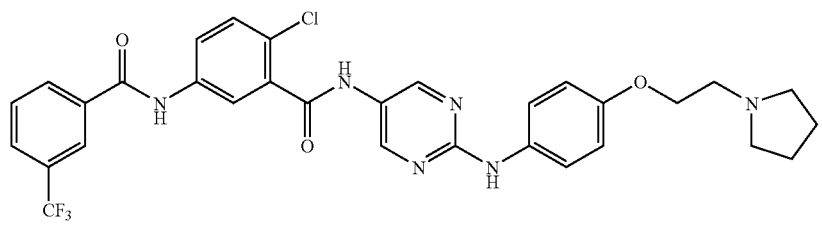

XL

A mixture of intermediates 1 (Example 2) (336 mg, 0.978 mmol), 25 (Example 33) (195 mg, 0.652 mmol) and DIPEA (340 µL, 1.96 mmol) was dissolved in DMF (7 mL) and treated with HBTU (395 mg, 1.043 mmol) and HOBt (132 mg, 0.978 mmol) at room temperature for 16 h. The reaction mixture was extracted was triturated with ethyl acetate-water-brine (30 mL, 1:1:1). The organic layer was separated, dried ($Na_2SO_4$) and evaporated. The residue was purified to give title compound as a pale yellow solid (121 mg, 19%).

$^1$H NMR (500 MHz, DMSO-$d_6$): δ 1.65-1.75 (m, 4H), 2.45-2.55 (m, 4H), 2.75 (t, J=6.0 Hz, 2H), 3.97-4.07 (m, 2H), 6.86 (d, J=9.0 Hz, 2H), 7.58 (d, J=8.5 Hz, 1H), 7.62 (d, J=9.0 Hz, 2H), 7.80 (t, J=5.0 Hz, 1H), 7.98 (dd, J=2.5 Hz, J=8.0 Hz, 1H), 8.07 (d, J=2.5 Hz, 1H), 8.3-8.37 (m, 1H), 8.72 (s, 2H), 10.6-10.9 (br s, 2H). MS (ES+): m/z 625.43 (M+H)$^+$.

EXAMPLE 81

Synthesis of 2-Chloro-N-{2-[4-(4-Methyl-Piperazine-1-Carbonyl)-Phenylamino]-Pyrimidin-5-yl}-5-(3-Trifluoromethyl-Benzoylamino)-Benzamide (Compound XLI)

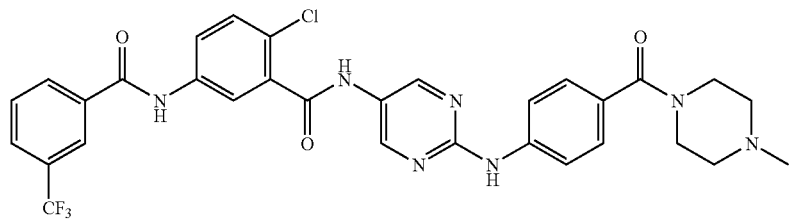

XLI

A mixture of intermediate 1 (Example 2) (40 mg, 1.2 mmol) and thionyl chloride (875 µL, 12 mmol) in dichloromethane (20 mL) was heated under reflux for 6 h. The reaction mixture was evaporated to dryness. To the residue was added (4-(5-aminopyrimidin-2-ylamino)phenyl)(4-methylpiperazin-1-yl)methanone (20 mg, 0.064 mmol) and TEA (44 µL, 0.31 mmol) in THF (7 mL). The reaction mixture was stirred at room temperature for 1 h and evaporated. The residue was purified by HPLC to give title compound as a yellow solid (21 mg, 52%).

$^1$H NMR (500 MHz, DMSO-$d_6$): δ 2.83 (s, 3H), 3.05-3.15 (m, 2H), 3.20-3.32 (m, 2H), 3.42-3.50 (m, 5H, overlapped with water), 7.41 (d, J=8.5 Hz, 2H), 7.60 (d, J=9.0 Hz, 1H), 7.81 (t, J=8.0 Hz, 1H), 7.86 (d, J=8.5 Hz, 2H), 7.93 (dd, J=2.5 Hz, J=9.0 Hz, 1H), 8.08 (d, J=5, 1H), 8.32 (s, 1H), 8.84 (s, 2H), 9.7-9.8 (br s, 1H), 10.0 (s, 1H), 10.72 (s, 1H), 10.74 (s, 1H). MS (ES+): m/z 638.37 (M+H)$^+$.

EXAMPLE 82

Synthesis of 2-Chloro-5-(Nicotinamido)Benzoyl Chloride (Intermediate 40)

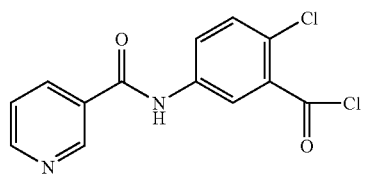

40

To a solution of 5-amino-2-chlorobenzoic acid (1.71 g, 10 mmol) and TEA (6.96 mL, 50 mmol) in THF (50 mL) was added nicotinoyl chloride hydrochloride (1.78 g, 10 mmol) solid portion-wise. After 1 h stirring at room temperature, product was isolated through filtration as a white solid. The solid was washed with water and dried (1.85 g, 67%). The solid, 2-chloro-5-(nicotinamido)benzoic acid (1.0 g, 3.62 mmol) was suspended in dichloromethane (50 mL) and treated with thionyl chloride (1.57 mL, 36.2 mmol) at reflux for 6 hr. The reaction mixture was evaporated, and the residue was dissolved in hexane-ethyl acetate mixture (100 mL, 6:4) and quickly filtered through a short silica plug. On evaporation of solvent, the title compound was obtained as a white solid (873 mg, 82%).

EXAMPLE 83

Synthesis of N-(4-Chloro-3-{2-[4-(4-Methyl-Piperazine-1-Carbonyl)-Phenylamino]-Pyrimidin-5-ylcarbamoyl}Phenyl)-Nicotinamide (Compound XLII)

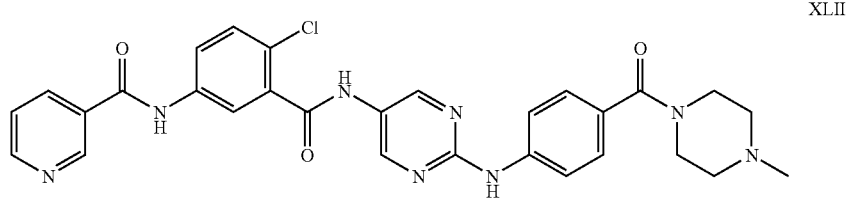

XLII

To a solution of (4-(5-aminopyrimidin-2-ylamino)phenyl)(4-methylpiperazin-1-yl)methanone (31 mg, 0.1 mmol) and TEA (69 μL, 0.5 mmol) in THF (7 mL), was added intermediate 40 (Example 82) (23 mg, 0.063 mmol) in DCM (5 mL). The reaction mixture was stirred at room temperature for 16 h and evaporated. The residue was purified by HPLC to give title compound as a yellow solid (20 mg, 35%).

$^1$H NMR (500 MHz, DMSO-d$_6$): δ 2.83 (s, 3H), 3.05-3.15 (m, 2H), 3.2-3.32 (m, 2H), 3.42-3.50 (m, 5H, overlapped with water), 7.41 (d, J=8.5 Hz, 2H), 7.84-7.94 (m, 3H), 8.09 (d, J=3.0 Hz, 1H), 8.30-8.37 (m, 1H), 8.80 (d, J=3.5 Hz, 1H), 8.84 (s, 2H), 9.13 (s, 1H), 9.75-9.85 (br s, 1H), 10.0 (s, 1H), 10.71 (s, 1H), 10.74 (s, 1H). MS (ES+): m/z 571.20 (M+H)$^+$.

EXAMPLE 84

Synthesis of N-(2-(4-(2-(Pyrrolidin-1-yl)Ethoxy)Phenylamino)Pyrimidin-5-yl)-5-Amino-2-Methyl Menzamide (Intermediate 41)

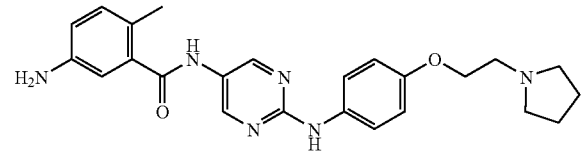

41

A mixture of 2-methyl-5-nitrobenzoic acid (760 mg, 2.53 mmol), intermediate 25 (Example 33) (690 mg, 3.80 mmol) and DIPEA (1.32 mL, 7.61 mmol) was dissolved in DMF (14 mL) and treated with HBTU (1.54 g, 4.06 mmol) and HOBt (514 mg, 3.80 mmol) at room temperature for 16 h. The reaction mixture was extracted was triturated with ethyl acetate-water-brine (100 mL, 1:1:1). The organic layer was separated, dried (Na$_2$SO$_4$), evaporated and filtered through a silica plug. The crude residue was obtained as a dark gold colored syrup.

The crude product was suspended in methanol (100 mL) and hydrogenated over Pd/C (10%, 150 mg) for 6 hr. The catalyst was removed through filtration, and the solvent was evaporated. The residue on purification using flash column chromatography gave the title compound (425 mg, 39%) as yellow solid.

EXAMPLE 85

Synthesis of 5-(2,2-Dimethyl-Propionylamino)-2-Methyl-N-{2-[4-(2-Pyrrolidin-1-yl-Ethoxy)-Phenyl Amino]-Pyrimidin-5-yl}-Benzamide (Compound XLIII)

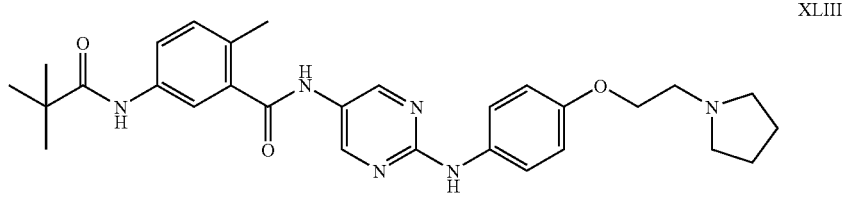

XLIII

To a suspension of intermediate 41 (Example 84) (200 mg, 0.462 mmol) in DCM (30 mL), was added and TEA (840 μL, 6.0 mmol) followed by trimethyl acetyl chloride (74 μL, 0.6 mmol). The reaction mixture was stirred at room temperature for 16 h, and triturated with aqueous sodium bicarbonate-brine mixture. The organic layer was separated and dried (Na$_2$SO$_4$). The product crashed out by adding hexane, as cream colored solid (235 mg, quantative).

$^1$H NMR (500 MHz, DMSO-d$_6$): δ 1.29 (s, 9H), 1.75-1.83 (m, 4H), 2.33 (s, 3H), 2.75-2.90 (m, 4H), 3.00-3.23 (m, 2H), 4.15 (t, J=5.0 Hz, 2H), 6.95 (d, J=9.0 Hz, 2H), 7.06 (d, J=9.0 Hz, 2H), 7.23 (d, J=8.5 Hz, 1H), 7.69 (dd, J=2.3 Hz, J=8.4 Hz, 1H), 7.87 (d, J=9.0 Hz, 1H), 9.06 (s, 2H), 9.33 (s, 1H), 10.77 (s, 1H). MS (ES+): m/z 517.27 (M+H)$^+$.

EXAMPLE 86

Synthesis of 2-Methyl-5-(3-Phenyl-Ureido)-N-{2-[4-(2-Pyrrolidin-1-yl-Ethoxy)-Phenylamino]-Pyrimidin-5-yl}-Benzamide (Compound XLIV)

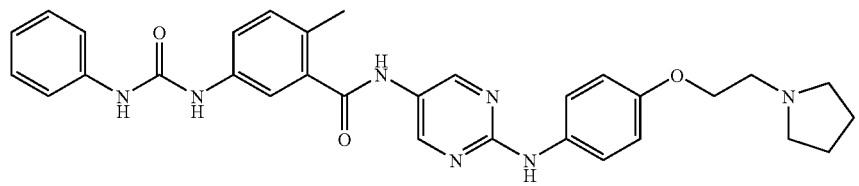

XLIV

To a suspension of intermediate 41 (Example 84) (208 mg, 0.48 mmol) in DCM (10 mL), was added phenyl isocyanate (58 µL, 0.53 mmol). The reaction mixture was stirred at room temperature for 4 hr, and triturated with aqueous sodium bicarbonate-brine mixture. The organic layer was separated, dried ($Na_2SO_4$) and evaporated. The residue was triturated with DCM-MeOH-Hexane to give white solid (83 mg, 32%).

$^1$H NMR (500 MHz, DMSO-$d_6$): δ 1.68-1.79 (m, 4H), 2.32 (s, 3H), 2.62-2.75 (m, 4H), 2.85-2.96 (m, 2H), 4.06 (t, J=6.0 Hz, 2H), 6.89 (d, J=9.0 Hz, 2H), 6.96 (t, J=7.5 Hz, 1H), 7.21 (d, J=8.4 Hz, 1H), 7.27 (t, J=7.6 Hz, 1H), 7.40-7.48 (m, 3H), 7.58-7.68 (m, 3H), 8.73 (s, 2H), 8.80 (s, 1H), 8.87 (s, 1H), 9.4 (s, 1H), 10.31 (s, 1H). MS (ES+): m/z 552.3 (M+H)$^+$.

EXAMPLE 87

Synthesis of 5-(5-Methylisoxazole-3-Carboxamido)-2-Chlorobenzoic Acid (Intermediate 42)

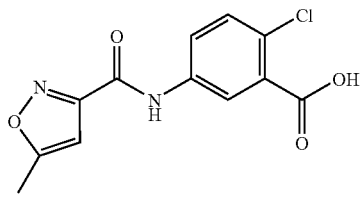

42

Ethyl 5-methylisoxazole-3-carboxylate (500 mg, 3.22 mmol) was suspended in MeOH-THF-$H_2O$ (20 mL, 1:1:1) and lithium hydroxide monohydrate (1.35 g, 32.2 mmol) was added. The reaction mixture was stirred for 16 h at room temperature, and acidified with 1N HCl. The crude product was extracted with ethyl acetate, and ethyl acetate layer was dried ($Na_2SO_4$) and solvent evaporated. The white solid thus obtained, was suspended in dichloromethane (30 mL) and treated with thionyl chloride (2.35 mL, 32.3 mmol) at reflux for 6 hr. The reaction mixture was evaporated, and the residue was dissolved in hexane-ethyl acetate mixture (100 mL, 6:4) and quickly filtered through a short silica plug. On evaporation of solvent, 5-methylisoxazole-3-carbonyl chloride was obtained as a colorless syrup (330 mg, 70%).

To a solution of 5-amino-2-chlorobenzoic acid (342 mg, 2.0 mmol) and TEA (1.39 mL, 10 mmol), was added 5-methylisoxazole-3-carbonyl chloride (300 mg, 2.06 mmol) in DCM (5 mL). The reaction mixture was stirred at room temperature for 16 hr, and triturated with aqueous sodium bicarbonate. The organic layer was separated, dried ($Na_2SO_4$) and evaporated. The residue on filtered through a silica plug to give the title compound as a cream colored solid (330 mg, 57%).

EXAMPLE 88

Synthesis of N-(3-(2-(4-(2-(Pyrrolidin-1-yl)Ethoxy)Phenylamino)Pyrimidin-5-ylcarbamoyl)-4-Chlorophenyl)-5-Methylisoxazole-3-Carboxamide (Compound XLV)

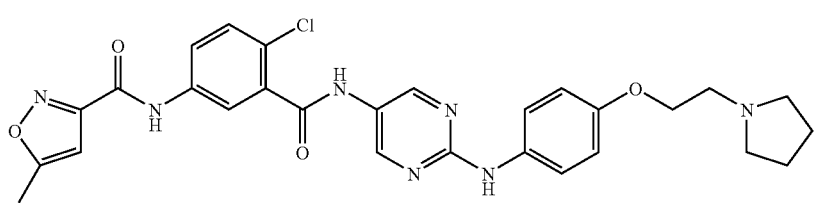

XLV

To a solution of intermediate 42 (330 mg, 1.17 mmol) in DCM (20 mL) was added thionyl chloride (853 μL, 11.7 mmol). The reaction mixture was heated under reflux for 2 h and the solvent evaporated. The residue was dissolved in hexane-ethyl acetate mixture (100 mL, 6:4) and quickly filtered through a short silica plug. The solvent evaporated and the residue was treated with intermediate 25 (Example 33) (387 mg, 1.29 mmol) and TEA (815 μL, 5.85 mmol) at room temperature for 16 hr. After evaporating the solvent, the residue was purified on HPLC to give the title compound as colorless syrup (21 mg, 3%).

$^1$H NMR (500 MHz, DMSO-d$_6$): δ 1.83-1.95 (m, 2H), 1.95-2.08 (m, 2H), 3.06-3.18 (m, 2H), 3.55-3.65 (m, 4H), 2.75 (t, J=6.0 Hz, 2H), 4.25 (t, J=4.95 Hz, 2H), 6.69 (s, 1H), 6.96 (d, J=9.5 Hz, 2H), 7.58 (d, J=8.8 Hz, 1H), 7.66 (d, J=9.0 Hz, 2H), 7.89 (dd, J=2.5 Hz, J=8.8 Hz, 1H), 8.08 (d, J=2.6 Hz, 1H), 8.72 (s, 2H). MS (ES+): m/z 562.13 (M+H)$^+$.

EXAMPLE 89

General Procedure for the Amide Bond Formation (Method A)

To a solution of an amino-compound (1.0 mol equiv) and a carboxylic acid (1.2 mol equiv) in dry DMF (0.05-0.2 M) was added HBTU (1.5 mol equiv) and HOBt (1.3 mol equiv) followed by DIPEA (3.0 mol equiv). The reaction mixture was stirred at room temperature for specific time (as shown below) and then poured into water. The mixture was extracted with ethyl acetate and the combined organic layers washed with water, brine, dried over Na$_2$SO$_4$ and filtered. The filtrate was concentrated in vacuo and the crude product purified as described below.

EXAMPLE 90

General Procedure for the Reduction of Nitro-Compound (Method B)

A solution of a nitro-compound (1.0 mol equiv) in MeOH (0.05-1.0 M) was flushed with argon and then Pd/C (10% by wt) added. The mixture was evacuated and then refilled with hydrogen (2 cycles) and stirred at room temperature for 24 h. The heterogeneous reaction mixture was filtered through a pad of CELITE, washed with MeOH and concentrated in vacuo to furnish the corresponding amino-compound. The crude amino-compound was used in the next step without purification.

EXAMPLE 91

Synthesis of 4-Bromo-N-(2-pyrrolidin-1-yl-ethyl)-benzenesulfonamide (Intermediate 43)

43

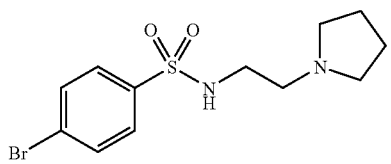

4-bromo-benzenesulfonyl chloride (3.36 g, 13.1 mmol, 1 equiv) was dissolved in 50 mL DCM and treated with TEA (9.16 mL, 65.7 mmol, 5 equiv). To this, while stirring the solution, was added 2-pyrrolidin-1-yl-ethylamine (3 g, 26.3 mmol, 2 equiv). After 3 h, reaction was poured onto DCM/water mixture and washed once. The aqueous phase was back extracted once with fresh DCM. Organic phases were combined, washed once with brine and dried over sodium sulfate. Filtration followed by rotary evaporation provided desired product. White needles (3.92 g, 90%). R$_f$=0.35 (10% MeOH/DCM)

EXAMPLE 92

Synthesis of 4-(5-Nitro-Pyrimidin-2-ylamino)-N-(2-Pyrrolidin-1-yl-ethyl)-Benzenesulfonamide (Intermediate 44)

44

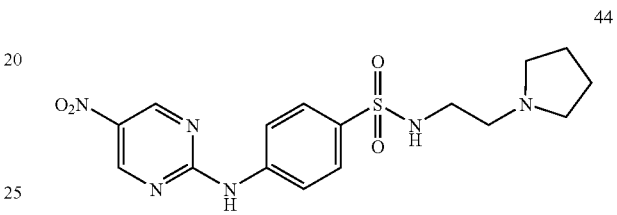

A mixture of 2-amino-5-nitropyrimdin (7.14 mmol, 1.0 equiv), intermediate 43 (Example 91) (10.71 mmol, 1.5 equiv), Pd(OAc)$_2$ (0.357 mmol, 0.05 equiv), Xantphos (0.714 mmol, 0.1 equiv) and potassium-tert-butoxide (14.28 mmol, 2.0 equiv) was suspended in 40 mL of dioxane and refluxed at 100° C. under an argon atmosphere for 18 h. The mixture was allowed to cool to room temperature, filtered and washed with DCM. The filtrate was concentrated and the crude product precipitated out using EtOAc/Hexanes (1:5 v/v) to afford the title compound as a yellow solid (1.67 g, 60%). MS (ES+): m/z=393 (M+H)$^+$. LC retention time: 1.79 min.

EXAMPLE 93

Synthesis of 4-(5-Amino-Pyrimidin-2-ylamino)-N-(2-Pyrrolidin-1-yl-Ethyl)-Benzenesulfonamide (Intermediate 45)

45

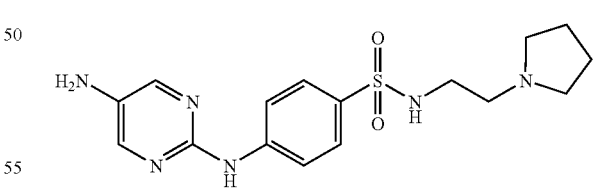

Intermediate 44 (Example 92) (4.26 mmol, 1.0 equiv) dissolved in MeOH (0.05-1.0 M) was evacuated of air and placed under an argon blanket; Pd/C (10% by wt) was then added. The mixture was evacuated and then refilled with hydrogen and stirred at room temperature for 4 h. Filtration through CELITE with a MeOH wash, followed by concentration under reduced pressure afford the title compound as a white solid (100 mg, 7%). The crude amino-compound was used in the next step without purification. MS (ES+): m/z=363 (M+H)$^+$. LC retention time: 1.34 min.

EXAMPLE 94

Synthesis of 2-Chloro-N-{2-[4-(2-Pyrrolidin-1-yl-Ethylsulfamoyl)-Phenylamino]-Pyrimidin-5-yl}-5-(3-Trifluoromethyl-Benzoylamino)-Benzamide (Compound XLVI)

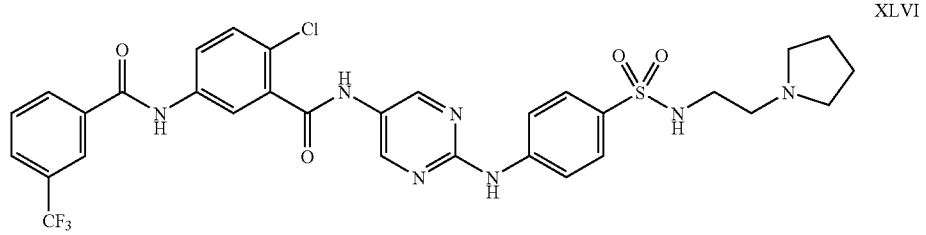

XLVI

The title compound was prepared from intermediates 1 (Example 2) (80 mg, 0.23 mmol) and 45 (Example 93) (70 mg, 0.19 mmol) according to Method A. The mixture was stirred at RT for 30 h and the crude product purified by HPLC to afford the title compound (TFA salt; 55 mg 36%) as a light brown solid.

$^1$H NMR (500 MHz, DMSO-$d_6$): 1.78-1.95 (m, 2H), 1.95-2.05 (m, 2H), 2.95-3.05 (m, 4H), 3.15-3.25 (m, 2H), 3.50-3.60 (m, 2H), 7.62 (d, J=8.8 Hz, 1H), 7.74 (d, J=8.9 Hz, 2H), 7.77 (t, J=6.9 Hz, 1H), 7.82 (t, J=7.8 Hz, 1H), 7.93 (dd, J=8.8 Hz, J=2.6 Hz, 1H), 7.95-8.05 (m, 1H), 7.99 (d, J=9.0 Hz, 2H), 8.10 (d, J=2.6 Hz, 1H), 8.29 (d, J=8.1 Hz, 1H), 8.32 (s, 1H), 8.89 (s, 1H), 9.53 (br s, 1H), 10.25 (s, 1H), 10.76 (s, 1H), 10.78 (s, 1H). MS (ES+): m/z 688 (M+H)$^+$.

EXAMPLE 95

Synthesis of (5-Bromo-Pyridin-2-yl)-[4-(2-Hydroxy-Ethyl)-Piperazin-1-yl]-Methanone (Intermediate 46)

46

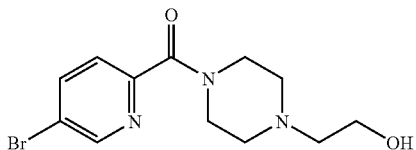

The title compound was prepared from 5-bromo-pyridine-2-carboxylic acid (1.0 g, 5.0 mmol) and 2-piperazin-1-yl-ethanol (1.0 g, 7.7 mmol) according to Method A (Example 89). After the removal of solvent, the residue was triturated in hexane-Et$_2$O (5:1 v/v) and the white solid filtered (1.0 g, 65%).

EXAMPLE 96

Syntheses of [4-(2-Hydroxy-Ethyl)-Piperazin-1-yl]-[5-(5-Nitro-Pyrimidine-2-ylamino)-Pyridin-2yl]-Methanone (Intermediate 47)

47

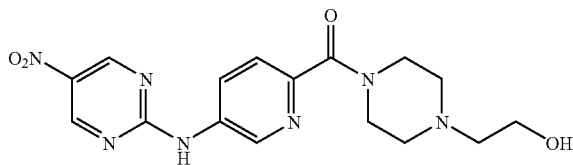

A mixture of 5-nitro-pyrimidin-2-ylamine (0.85 g, 6.1 mmol), intermediate 46 (Example 95) (2.5 g, 8.0 mmol), Pd(OAc)$_2$ (0.40 g, 0.44 mmol), Xantphos (0.5 g, 0.86 mmol) and cesium carbonate (4.0 g, 12 mmol) was suspended in dioxane (30 mL) and heated at reflux under the argon atmosphere for 18 h. The mixture was allowed to cool to room temperature, filtered and washed with DCM. The filtrate was concentrated and the crude product purified by flash chromatography on silica gel (5% MeOH/DCM to 15% MeOH/DCM) to afford the title compound (0.90 g, 40%) as a yellow solid.

$^1$H NMR (500 MHz, DMSO-$d_6$): δ 2.35-2.45 (m, 4H), 2.45-2.52 (m, 2H), 3.45-3.55 (m, 4H), 3.58-3.65 (m, 2H), 4.43 (t, J=5.4 Hz, 1H), 7.64 (d, J=8.5 Hz, 1H), 8.31 (dd, J=8.7 Hz, J=2.5 Hz, 1H), 8.93 (d, J=2.2 Hz, 1H), 9.31 (s, 2H), 11.17 (s, 1H). MS (ES+): m/z 374 (M+H)$^+$.

EXAMPLE 97

Synthesis of [5-(5-Amino-Pyrimidin-2-ylamino)-Pyridin-2-yl]-[4-(2-Hydroxy-Ethyl)-Piperazin-1-yl]-Methanone (Intermediate 48)

48

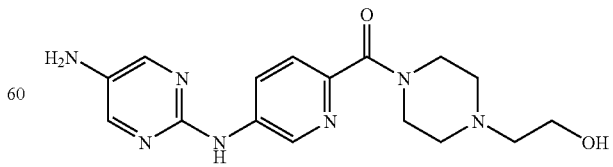

The title compound was prepared from intermediate 47 (Example 96) (0.70 g, 1.9 mmol) according to Method B (Example 90) and used in the next step without purification. MS (ES+): m/z 344 (M+H)$^+$.

EXAMPLE 98

Synthesis of 2-Chloro-N-(2-{6-[4-(2-Hydroxy-Ethyl)-Piperazine-1-Carbonyl]-Pyridin-3-ylamino}-Pyrimidin-5-yl)-5-(3-Trifluoromethyl-Benzoylamino)-Benzamide (Compound XLVII)

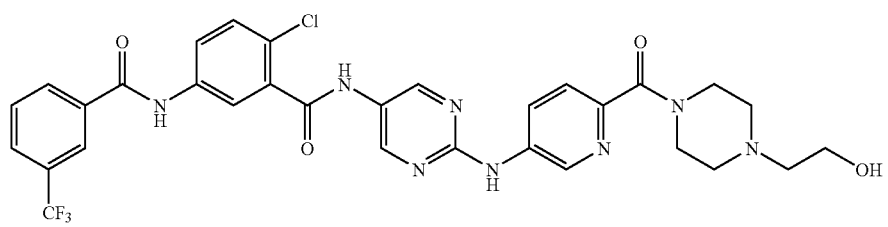

XLVII

The title compound was prepared from intermediates 1 (Example 2) (0.10 g, 0.29 mmol) and 48 (Example 97) (0.10 g, 0.29 mmol) according to Method A (Example 89). The mixture was stirred at RT for 20 h and the crude product purified by HPLC to afford the title compound (TFA salt; 44 mg 19%) as a light brown solid.

$^1$H NMR (500 MHz, DMSO-d$_6$): δ 3.10-3.30 (m, 4H), 3.40-3.65 (m, 4H), 3.70-3.80 (m, 2H), 4.40-4.60 (m, 2H), 5.41 (br s, 1H), 7.62 (d, J=8.8 Hz, 1H), 7.71 (d, J=8.7 Hz, 1H), 7.82 (t, J=7.9 Hz, 1H), 7.93 (dd, J=8.8 Hz, J=2.5 Hz, 1H), 8.01 (d, J=7.3 Hz, 1H), 8.10 (d, J=2.6 Hz, 1H), 8.29 (d, J=8.0 Hz, 1H), 8.32 (s, 1H), 8.39 (dd, J=8.7 Hz, J=2.6 Hz, 1H), 8.89 (s, 1H), 8.92 (d, J=2.5 Hz, 1H), 9.76 (br s, 1H), 10.26 (s, 1H), 10.76 (s, 1H), 10.78 (s, 1H). MS (ES+): m/z 669 (M+H)$^+$.

EXAMPLE 99

Synthesis of 3-(4-Bromo-Phenyl)-Propan-1-ol (Intermediate 49)

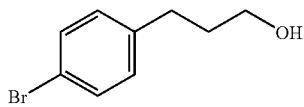

49

To a solution of 3-(4-bromo-phenyl)-propionic acid (4.0 g, 18 mmol) in THF (30 mL) at 0° C. under the argon atmosphere was added LiAlH$_4$ (1.0 M in THF; 14 mL, 14 mmol). After the addition, the ice-bath was removed and the mixture refluxed for 18 h. After cooling to room temperature, the reaction was quenched with 1 M HCl and the mixture extracted with ethyl acetate. The organic layer was separated, washed with brine, dried over Na$_2$SO$_4$ and filtered. The filtrate was concentrated and the crude product used in the next step without further purification.

EXAMPLE 100

Synthesis of 1-Bromo-4-(3-Bromo-Propyl)-Benzene (Intermediate 50)

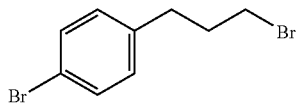

50

To a solution of intermediate 49 (Example 99) (4.0 g, 19 mmol) in THF (30 mL) at 0° C. under the argon atmosphere was added PPh$_3$ (6.3 g, 24 mmol) followed by CBr$_4$ (8.0 g, 24 mmol). The mixture was stirred at the same temperature for 15 min and then stirred at room temperature for additional 15 h. Most of the solvent was removed and the residue purified by flash chromatography on silica gel (hexane) to afford the title compound (3.5 g, 66%) as a colorless oil.

$^1$H NMR (500 MHz, DMSO-d$_6$): δ 2.03-2.12 (m, 2H), 2.68 (t, J=7.5 Hz, 2H), 3.49 (t, J=6.5 Hz, 2H), 7.19 (d, J=8.3 Hz, 2H), 7.47 (d, J=8.3 Hz, 2H).

EXAMPLE 101

Synthesis of 1-[3-(4-Bromo-Phenyl)-Propyl]-Pyrrolidine (Intermediate 51)

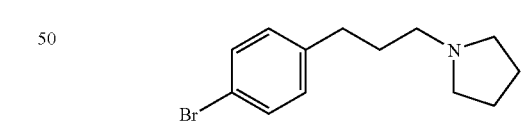

51

To a solution of intermediate 50 (Example 100) (3.5 g, 13 mmol) in dioxane (40 mL) was added pyrrolidine (2.1 mL, 25 mmol), followed by cesium carbonate (8.2 g, 25 mmol). The mixture was stirred at room temperature for 15 h and poured into water. The mixture was extracted with ethyl acetate and the organic layer separated, washed with brine, dried over Na$_2$SO$_4$ and filtered. The filtrate was concentrated and the residue purified by flash chromatography on silica gel (10% MeOH/DCM to 25% MeOH and 2% TEA/DCM) to afford the title compound (1.8 g, 53%) as a pale orange oil.

$^1$H NMR (500 MHz, DMSO-d$_6$): δ 1.60-1.65 (m, 6H), 2.35 (t, J=7.3 Hz, 2H), 2.35-2.43 (m, 4H), 2.57 (t, J=7.7 Hz, 2H), 7.16 (d, J=8.3 Hz, 2H), 7.44 (d, J=8.4 Hz, 2H).

EXAMPLE 102

Synthesis of (5-Nitro-Pyrimidin-2-yl)-[4-(3-Pyrrolidin-1-yl-Propyl)-Phenyl]-Amine (Intermediate 52)

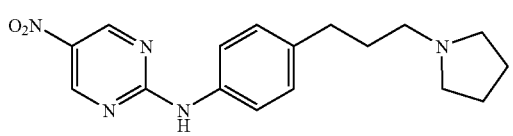

A mixture of 5-nitro-pyrimidin-2-ylamine (0.15 g, 1.1 mmol), intermediate 51 (Example 101) (0.30 g, 1.1 mmol), Pd$_2$(dba)$_2$ (75 mg, 0.082 mmol), Xantphos (96 mg, 0.17 mmol) and cesium carbonate (0.69 g, 2.1 mmol) was suspended in dioxane (15 mL) and heated at reflux under the argon atmosphere for 15 h. The mixture was allowed to cool to room temperature, filtered and washed with DCM. The filtrate was concentrated and the residue purified by flash chromatography on silica gel (10% MeOH/DCM to 20% MeOH and 2% TEA/DCM) to afford the title compound as a yellow solid (0.20 g, 56%).

EXAMPLE 103

Synthesis of N-[4-(3-Pyrrolidin-1-yl-propyl)-Phenyl]-Pyrimidine-2,5-Diamine (Intermediate 53)

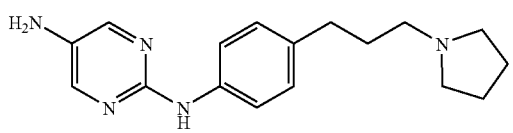

The title compound was prepared from intermediate 52 (Example 102) (0.20 g, 0.61 mmol) according to Method B (Example 90) and used in the next step without further purification.

EXAMPLE 104

Synthesis of 2-Chloro-N-{2-[4-(3-Pyrrolidin-1-yl-Propyl)-Phenylamino]-Pyrimidin-5-yl}-5-(3-Trifluoromethyl-Benzoylamino)-Benzamide (Compound XLVIII)

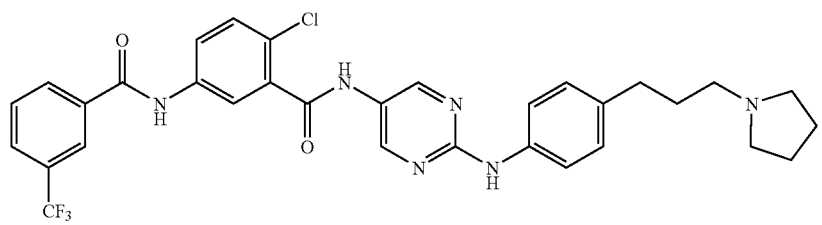

The title compound was prepared from intermediates 1 (Example 2) (0.26 g, 0.76 mmol) and 53 (Example 103) (0.20 g, 0.67 mmol) according to Method A (Example 89). The mixture was stirred at room temperature for 18 h and the crude product was purified by flash chromatography on silica gel (DCM to 30% MeOH/DCM) to afford the title compound (0.14 g, 34%) as a yellow solid.

$^1$H NMR (500 MHz, DMSO-d$_6$): δ 1.75-2.05 (m, 6H), 2.59 (t, J=7.6 Hz, 2H), 2.95-3.05 (m, 2H), 3.05-3.15 (m, 2H), 3.45-3.60 (m, 2H), 7.14 (d, J=8.5 Hz, 2H), 7.60 (d, J=8.8 Hz, 1H), 7.68 (d, J=8.5 Hz, 2H), 7.82 (t, J=7.9 Hz, 1H), 7.93 (dd, J=8.8 Hz, J=2.6 Hz, 1H), 8.01 (d, J=7.8 Hz, 1H), 8.08 (d, J=2.5 Hz, 1H), 8.28 (d, J=8.0 Hz, 1H), 8.32 (s, 1H), 8.76 (s, 2H), 9.49 (br s, 1H), 9.63 (s, 1H), 10.26 (s, 1H), 10.63 (s, 1H), 10.74 (s, 1H). MS (ES+): m/z 623 (M+H)$^+$.

EXAMPLE 105

Synthesis of (5-Nitro-Pyrimidin-2-yl)-Phenyl-Amine (Intermediate 54)

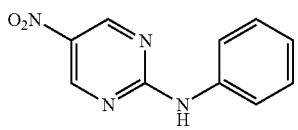

A suspension of 5-nitro-pyrimidin-2-ylamine (0.10 g, 0.71 mmol), bromobenzene (0.15 g, 0.96 mmol), Pd(OAc)$_2$ (13 mg, 0.057 mmol), Xantphos (67 mg, 0.12 mmol) and potassium tert-butoxide (0.22 g, 2.0 mmol) in DMF (3 mL) was sealed in a microwave reaction tube and irradiated with microwave at 140° C. for 15 min. After cooling to room temperature, the cap was removed and the resulting mixture filtered and the filtered solid washed with DCM. The filtrate was concentrated and the crude product used in the next step without further purification.

EXAMPLE 106

Synthesis of N-Phenyl-Pyrimidine-2,5-Diamine (Intermediate 55)

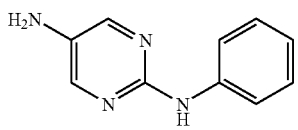

The title compound was prepared from intermediate 54 (Example 105) according to Method B (Example 90) and used in the next step without further purification.

EXAMPLE 107

Synthesis of 2-Chloro-N-(2-Phenylamino-Pyrimidin-5-yl)-5-(3-Trifluoromethyl-Benzoylamino)-Benzamide (Compound XLIX)

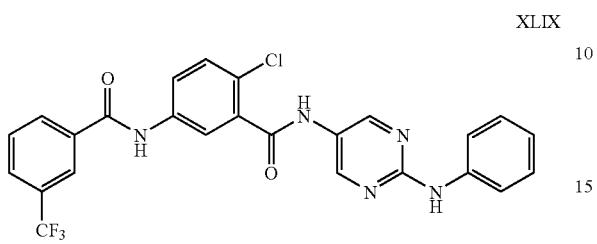

XLIX

The title compound was prepared from intermediates 1 (Example 2) (0.24 g, 0.70 mmol) and 55 (Example 106) (0.13 g, 0.70 mmol) according to Method A (Example 89). The mixture was stirred at room temperature for 15 h and the crude product was purified by HPLC. The combined fractions were poured into saturated NaHCO$_3$ and extracted with EtOAc. The combined organic layers were washed with brine, dried over Na$_2$SO$_4$ and filtered. The filtrate was concentrated and the residue further purified by preparative TLC (40% EtOAc/Hexane) to afford the title compound as a brown solid (13 mg, 4%).

$^1$H NMR (500 MHz, DMSO-d$_6$): δ 6.93 (t, J=7.3 Hz, 1H), 7.27 (d, J=7.5 Hz, 1H), 7.29 (d, J=7.5 Hz, 1H), 7.61 (d, J=8.7 Hz, 1H), 7.75 (d, J=8.7 Hz, 2H), 7.82 (t, J=7.8 Hz, 1H), 7.96 (dd, J=8.8 Hz, J=2.6 Hz, 1H), 8.00 (d, J=8.6 Hz, 1H), 8.05 (d, J=2.6 Hz, 1H), 8.29 (d, J=8.0 Hz, 1H), 8.33 (s, 1H), 8.79 (s, 2H), 9.68 (s, 1H), 10.65 (s, 1H), 10.73 (s, 1H). MS (ES+): m/z 512 (M+H)$^+$.

EXAMPLE 108

Synthesis of 2-Chloro-5-(Quinolin-2-ylamino)-Benzoic Acid (Intermediate 56)

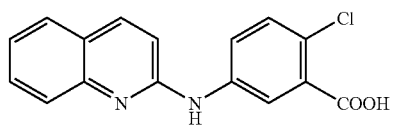

56

A solution of 2-chloro-quinoline (0.50 g, 3.1 mmol) and 5-amino-2-chloro-benzoic acid (0.53 g, 3.1 mmol) in acetic acid (10 mL) was heated at 100° C. for 2 h. Acetic acid was removed and the residue triturated in ethyl acetate. The title compound was obtained as a white solid (0.55 g, 59%) after the filtration. MS (ES+): m/z 299 (M+H)$^+$.

EXAMPLE 109

Synthesis of 2-Chloro-N-[2-(Pyridin-3-ylamino)-Pyrimidin-5-yl]-5-(Quinolin-2-ylamino)-Benzamide (Compound L)

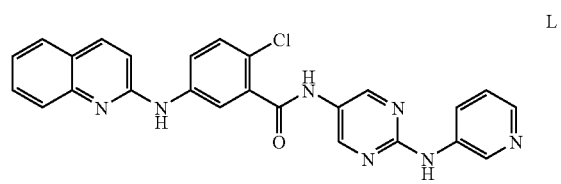

L

The title compound was prepared from intermediates 56 (Example 108) (64 mg, 0.21 mmol) and 9 (Example 15) (40 mg, 0.21 mmol) according to Method A (Example 89). The mixture was stirred at room temperature for 2.5 days and the crude product was purified by HPLC to afford the title compound (TFA salt; 17 mg, 14%) as a brown solid.

$^1$H NMR (500 MHz, DMSO-d$_6$): δ 7.09 (d, J=9.0 Hz, 1H), 7.34 (t, J=7.4 Hz, 1H), 7.54 (d, J=8.9 Hz, 1H), 7.61 (t, J=7.6 Hz, 1H), 7.71 (d, J=8.4 Hz, 1H), 7.77 (d, J=7.9 Hz, 1H), 7.80-7.90 (m, 1H), 8.13 (d, J=9.0 Hz, 2H), 8.33 (d, J=2.6 Hz, 1H), 8.40 (s, 1H), 8.55 (d, J=8.4 Hz, 1H), 8.96 (s, 1H), 9.26 (s, 1H), 9.84 (s, 1H), 10.50 (s, 1H), 10.82 (s, 1H). MS (ES+): m/z 468 (M+H)$^+$.

EXAMPLE 110

Synthesis of 2-Methyl-N-[2-(Pyridin-3-ylamino)-Pyrimidin-5-yl]-5-[2-(3-Trifluoromethyl-Phenyl)-Acetylamino]-Benzamide (Compound LI)

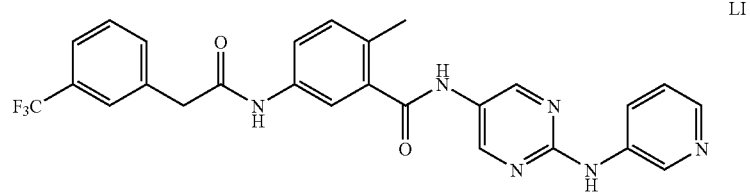

LI

The title compound was prepared from intermediate 31 (Example 57) (0.10 g, 0.31 mmol) and (3-trifluoromethyl-phenyl)-acetic acid (80 mg, 0.39 mmol) according to Method A (Example 89). The mixture was stirred at room temperature for 6 h and the crude product purified firstly by flash chromatography on silica gel (30% EtOAc/Hexane to 10% MeOH/EtOAc) and then further purified by preparative TLC (10% MeOH/DCM) to afford the title compound (20 mg, 13%) as a pale yellow solid.

$^1$H NMR (500 MHz, DMSO-d$_6$): δ 2.33 (s, 3H), 3.79 (s, 2H), 7.25 (d, J=8.4 Hz, 1H), 7.31 (dd, J=8.4 Hz, J=4.6 Hz, 1H), 7.55-7.68 (m, 5H), 7.70 (s, 1H), 7.77 (d, J=2.1 Hz, 1H), 8.14 (d, J=4.4 Hz, 1H), 8.21 (d, J=8.5 Hz, 1H), 8.81 (s, 2H), 8.87 (d, J=2.2 Hz, 1H), 9.83 (s, 1H), 10.36 (s, 1H), 10.40 (s, 1H). MS (ES+): m/z 507 (M+H)$^+$.

EXAMPLE 111

Synthesis of 5-Acetylamino-2-Chloro-Benzoic Acid (Intermediate 57)

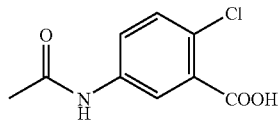

57

To a solution of 5-amino-2-chloro-benzoic acid (0.50 g, 2.9 mmol) in DCM (15 mL) was added acetyl chloride (0.30 mL, 4.2 mmol) followed by triethylamine (1.2 mL, 8.6 mmol). The mixture was stirred at RT for 2 h and poured into water. The mixture was extracted with ethyl acetate and the combined organic layers washed with water, brine, dried over Na$_2$SO$_4$ and filtered. The filtrate was concentrated and afforded the title compound (0.17 g, 27%) as a brown solid.

EXAMPLE 112

Synthesis of 4-{4-[5-(5-Acetylamino-2-Chloro-Benzoylamino)-Pyrimidin-2-ylamino]-Benzenesulfonyl}-Piperidine-1-Carboxylic Acid tert-Butyl Ester (Intermediate 58)

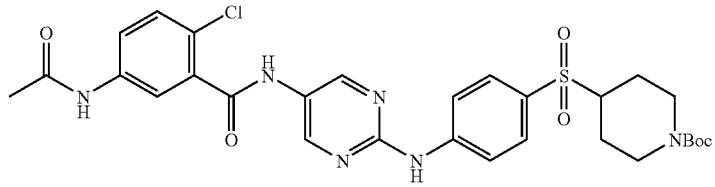

58

The title compound was prepared from intermediates 57 (Example 111) (0.17 g, 0.80 mmol) and 13 (Example 20) (0.34 g, 0.80 mmol) according to Method A (Example 89). The mixture was stirred at room temperature for 18 h and the crude product purified by flash chromatography on silica gel (hexane to EtOAc) to afford the title compound (0.25 g, 50%) as a white solid.

EXAMPLE 113

Synthesis of 5-Acetylamino-2-Chloro-N-{2-[4-(Piperidine-4-Sulfonyl)-Phenylamino]-Pyrimidin-5-yl}-Benzamide (Compound LII)

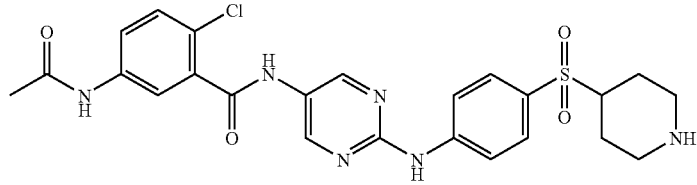

LII

To a solution of intermediate 58 (Example 112) (0.25 g, 0.40 mmol) in DCM (8 mL) was added TFA (30% in DCM, 6 mL) and the mixture stirred at room temperature for 2 h. The reaction mixture was concentrated and the residue purified by HPLC to afford the title compound (TFA salt; 50 mg, 23%) as a white solid.

$^1$H NMR (500 MHz, DMSO-d$_6$): δ 1.60-1.70 (m, 2H), 2.00-2.10 (m, 2H), 2.08 (s, 3H), 2.80-2.93 (m, 2H), 3.30-3.40 (m, 2H), 3.40-3.50 (m, 2H), 7.51 (d, J=8.7 Hz, 1H), 7.64 (dd, J=8.8 Hz, J=2.6 Hz, 1H), 7.74 (d, J=8.9 Hz, 2H), 7.91 (d, J=2.5 Hz, 1H), 8.04 (d, J=8.9 Hz, 2H), 8.20 (br s, 1H), 8.62 (br s, 1H), 8.89 (s, 2H), 10.27 (s, 1H), 10.37 (s, 1H), 10.74 (s, 1H). MS (ES+): m/z 529 (M+H)$^+$.

EXAMPLE 114

Synthesis of 2-Chloro-N-{2-[4-(3-Pyrrolidin-1-yl-Propyl)-Phenylamino]-Pyrimidin-5-yl}-5-(Quinolin-2-ylamino)-Benzamide (Compound LIII)

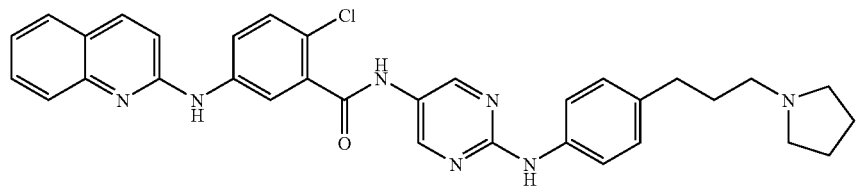

The title compound was prepared from intermediates 56 (Example 108) (0.10 g, 0.34 mmol) and 53 (Example 103) (0.10 g, 0.34 mmol) according to Method A (Example 89). The mixture was stirred at room temperature for 16 h and the crude product was purified by HPLC to afford the title compound (TFA salt; 80 mg, 35%) as a brown solid.

$^1$H NMR (500 MHz, DMSO-$d_6$): δ 1.75-2.05 (m, 6H), 2.59 (t, J=7.5 Hz, 2H), 2.93-3.03 (m, 2H), 3.08-3.15 (m, 2H), 3.50-3.60 (m, 2H), 7.10 (d, J=8.9 Hz, 1H), 7.15 (d, J=8.6 Hz, 2H), 7.34 (d, J=7.4 Hz, 1H), 7.53 (d, J=8.8 Hz, 1H), 7.60 (t, J=8.4 Hz, 1H), 7.65-7.75 (m, 3H), 7.77 (d, J=7.2 Hz, 1H), 8.10-8.20 (m, 2H), 8.30 (d, J=2.6 Hz, 1H), 8.80 (s, 2H), 9.63 (s, 1H), 9.77 (br s, 1H), 9.85 (br s, 1H), 10.63 (s, 1H). MS (ES+): m/z 578 (M+H)$^+$.

EXAMPLE 115

Synthesis of N-Benzyl-4-Methyl-3-{2-[4-(2-Pyrrolidin-1-yl-Ethylsulfamoyl)-Phenylamino]-Pyrimidin-5-ylamino}-Benzenesulfonamide (Compound LIV)

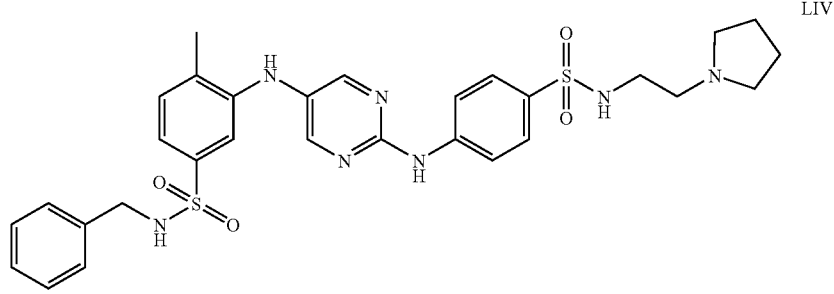

A suspension of intermediate 45 (Example 93) (0.10 g, 0.28 mmol), N-benzyl-3-bromo-4-methyl-benzenesulfonamide (0.10 g, 0.29 mmol), Pd(OAc)$_2$ (5 mg, 0.022 mmol), Xantphos (26 mg, 0.045 mmol) and potassium tert-butoxide (70 mg, 0.63 mmol) in a mixture of dioxane/DNIF (2/1, 3 mL) was sealed in a microwave reaction tube and irradiated with microwave at 150° C. for 20 min. After cooling to room temperature, the cap was removed and the resulting mixture filtered and the filtered solid washed with DCM. The filtrate was concentrated and the residue purified by flash chromatography on silica gel (10% MeOH/DCM to 25% MeOH and 2% TEA/DCM) to afford the title compound (0.10 g, 58%) as a white solid.

$^1$H NMR (500 MHz, DMSO-$d_6$): δ 1.55-1.65 (m, 4H), 2.32 (s, 3H), 2.30-2.40 (m, 4H), 2.43 (t, J=6.8 Hz, 2H), 2.75-2.85 (m, 2H), 3.90 (d, J=6.3 Hz, 2H), 7.15-7.27 (m, 7H), 7.33 (d, J=7.7 Hz, 2H), 7.48 (s, 1H), 7.69 (d, J=8.9 Hz, 2H), 7.94 (d, J=8.9 Hz, 2H), 8.00 (t, J=6.3 Hz, 1H), 8.43 (s, 2H), 10.06 (s, 1H). MS (ES+): m/z 622 (M+H)$^+$.

EXAMPLE 116

Synthesis of 4-Methyl-3-{2-[4-(2-Pyrrolidin-1-yl-Ethylsulfamoyl)-Phenylamino]-Pyrimidin-5-ylamino}-Benzenesulfonamide (Compound LV)

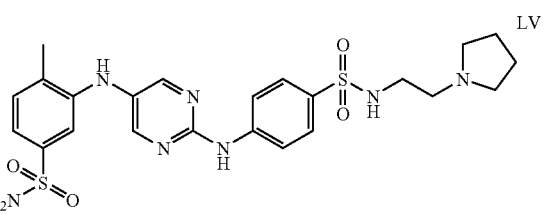

A solution of compound LIV (Example 115) (40 mg, 0.064 mmol) in conc. sulfuric acid (1.5 mL) was stirred at room temperature for 20 min. The mixture was poured into the ice-water and neutralized with 30% NaOH solution until the pH reached 5. The resulting solution was extracted with ethyl acetate and the organic layer separated. The organic layer was washed with brine, dried over Na$_2$SO$_4$ and filtered. The filtrate was concentrated and the residue triturated in MeOH/Et$_2$O (1/5). The title compound was obtained as a white solid (20 mg, 59%) after filtration.

$^1$H NMR (500 MHz, DMSO-$d_6$): δ 1.75-2.00 (m, 4H), 2.32 (s, 3H), 2.90-3.00 (m, 2H), 3.05-3.15 (m, 2H), 3.15-3.25 (m, 2H), 3.40-3.50 (m, 2H), 7.18 (dd, J=7.9 Hz, J=1.6 Hz, 1H), 7.20 (s, 1H), 7.27 (d, J=1.5 Hz, 1H), 7.30 (d, J=7.9 Hz, 1H), 7.60 (s, 1H), 7.74 (d, J=8.8 Hz, 2H), 7.98 (d, J=8.9 Hz, 2H), 8.47 (s, 2H), 10.11 (s, 1H), 10.96 (br s, 1H). MS (ESI+): m/z 532 (M+H)+.

EXAMPLE 117

Synthesis of N-(4-Chloro-3-nitrophenyl)-3-(trifluoromethyl)benzamide (Intermediate 59)

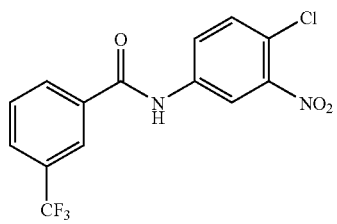

To a solution of 4-chloro-3-nitroaniline (1.72 g, 10.0 mmol) in 60 mL of anhydrous DCM was added crystalline DMAP (1.22 g, 10.0 mmol). The reaction mixture was stirred until all solids dissolved, then 3-trifluoromethylbenzoyl chloride (2.71 g, 13.0 mmol) was added dropwise. The reaction mixture was left to stir at ambient temperature for 6 hrs. The completion of the reaction was monitored by TLC and LC/MS. Then it was transferred into a separatory funnel and washed with water (3×100 mL), saturated NaHCO$_3$ (2×100 mL), brine (1×100 mL), dried over anhydrous Na$_2$SO$_4$ and filtered through a short pad of silica gel. Solvent was removed in vacuo to give the title product as a light-brown solid (3.4 g, 100% yield).

$^1$H NMR (500 MHz, DMSO-d$_6$): δ 7.74 (d, J=8.9 Hz, 1H), 7.80 (t, J=7.7 Hz, 1H), 7.98 (d, J=7.9 Hz, 1H), 8.06 (dd, J=8.9, 2.5 Hz, 1H), 8.26 (d, J=7.9 Hz, 1H), 8.30 (s, 1H), 8.56 (d, J=2.6 Hz, 1H), 10.90 (s, 1H).

EXAMPLE 118

Synthesis of N-(3-Amino-4-chlorophenyl)-3-(trifluoromethyl)benzamide (Intermediate 60)

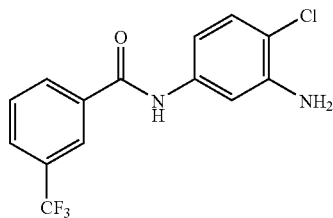

To a solution of intermediate 59 (10.34 g, 0.03 mol) in 500 mL of EtOH was added sodium sulfide nonahydrate (28.8 g, 0.12 mol). The reaction mixture was brought to reflux and refluxed for 4 hours. The progress of the reaction was monitored by TLC and LC/MS. Upon complete conversion to the product, the reaction mixture was allowed to cool down to ambient temperature and concentrated down in vacuo to approx. 200 mL of the total volume. The resulting suspension was partitioned between EtOAc and water. The organic layer was separated, washed with water (3×100 mL), brine (2×100 mL), dried over anhydrous Na$_2$SO$_4$ and filtered through a short pad of silica gel. Solvent was removed in vacuo to give the crude product. It was purified by silica gel flash chromatography using 0%-50% gradient of EtOAc in hexanes. Fractions, containing the product, were combined and solvent was removed in vacuo to afford the title compound as a tan solid (7.8 g, 83% yield).

$^1$H NMR (500 MHz, DMSO-d$_6$): δ 5.39 (s, 2H), 6.92 (dd, J=8.7, 2.4 Hz, 1H), 7.15 (d, J=8.6 Hz, 1H), 7.36 (d, J=2.4 Hz, 1H), 7.77 (t, J=7.9 Hz, 1H), 7.95 (d, J=7.8 Hz, 1H), 8.23 (d, J=8.0 Hz, 1H), 8.25 (s, 1H), 10.30 (s, 1H).

EXAMPLE 119

Synthesis of Methyl 2-{[4-(2-pyrrolidin-1-ylethoxy)phenyl]amino}pyrimidine-5-carboxylate (Intermediate 61)

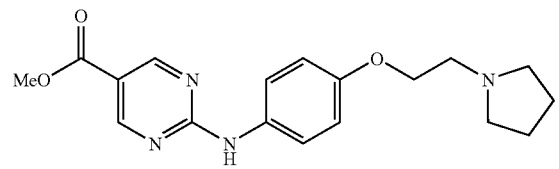

100 mL round-bottom flask was charged with methyl 2-aminopyrimidine-5-carboxylate (1.53 g, 10.0 mmol), 1-[2-(4-bromo-phenoxy)-ethyl]-pyrrolidine (4.05 g, 15.0 mmol), Pd$_2$(dba)$_3$ (366 mg, 0.4 mmol), XantPhos (694 mg, 1.2 mmol), Cs$_2$CO$_3$ (6.51 g, 20.0 mmol) and anhydrous dioxane (70 mL). The mixture was purged with argon gas for 15 min, and then refluxed under argon atmosphere for 2 days. After cooling to room temperature, the reaction mixture was partitioned between EtOAc and H$_2$O. The aqueous layer was extracted with EtOAc (3×100 mL). Combined EtOAc solutions were washed with H$_2$O (2×100 mL), brine (2×100 mL) and dried over anhydrous Na$_2$SO$_4$. The resulting solution was concentrated in vacuo with ca. 15 g of silica gel. The loaded silica gel was taken to the ISCO system for further purification (80 g column, solid method, 0% to 20% MeOH gradient in DCM, 40 min method). Fractions, containing the product, were combined and concentrated in vacuo to give a yellow solid. The solid was re-crystallized from 20 mL of CH$_3$CN to give the title compound as a beige powder (1.61 g, 47% yield).

$^1$H NMR (500 MHz, DMSO-d$_6$): δ 1.67-1.70 (m, 4H), 2.50-2.54 (m, 4H), 2.79 (t, J=5.9 Hz, 2H), 4.04 (t, J=5.9 Hz, 2H), 6.92 (d, J=9.1 Hz, 2H), 7.60 (d, J=9.1 Hz, 2H), 8.84 (s, 2H), 10.14 (s, 1H).

EXAMPLE 120

Synthesis of 2-{[4-(2-Pyrrolidin-1-ylethoxy)phenyl]amino}pyrimidine-5-carboxylic acid (Intermediate 62)

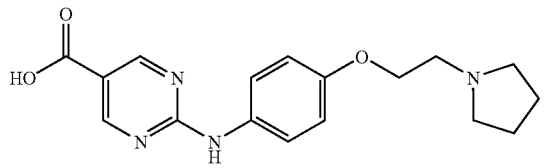

62

To a suspension of intermediate 61 (1.61 g, 4.70 mmol) in 20 ml of $CH_3CN$ was added a solution of LiOH (260.0 mg, 10.85 mmol) in 20 mL of $H_2O$. The reaction mixture was stirred at ambient temperature for 18 hrs. The progress of the reaction was monitored by TLC and LC/MS. Then 12 N HCl (0.90 mL, 10.85 mmol) was added and solvent was removed in vacuo to give a yellow solid. 100 mL of toluene were added and solvent was removed in vacuo until all solids were dry. Toluene addition and removal process was repeated three times to ensure a complete azeotropic removal of $H_2O$. The solid was dried in high vacuum for 1 hr and taken to the next step without further purification.

EXAMPLE 121

Synthesis of N-(2-Chloro-5-{[3-(trifluoromethyl)benzoyl]amino}phenyl)-2-{[4-(2-pyrrolidin-1-ylethoxy)phenyl]amino}pyrimidine-5-carboxamide (Compound LVI)

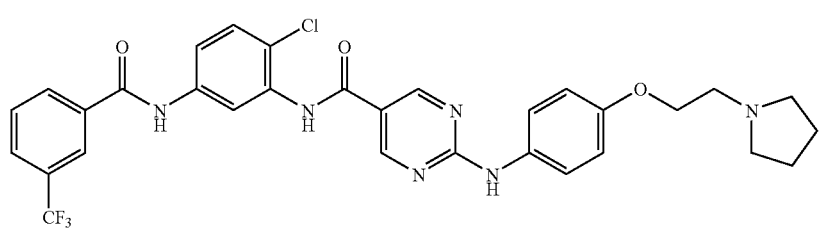

LVI 100 mL round-bottom flask was charged with intermediate 62 (772 mg, 2.35 mmol) and 2.0 M solution of thionyl chloride in DCM (12 mL, 23.5 mmol, 10 equiv.) under argon atmosphere. A reflux condenser was inserted and the reaction mixture was refluxed under argon atmosphere for 18 hrs. Then ca. 40 mL of anhydrous toluene were added and the reaction mixture was concentrated in vacuo down to ca. 10 mL of the total volume. This process was repeated three times. Then to the resulting solution of 2-{[4-(2-pyrrolidin-1-ylethoxy)phenyl]amino}pyrimidine-5-carboxyl chloride in ca. 10 mL of anhydrous toluene was added a solution of intermediate 60 (787 mg, 2.5 mmol) and DMAP (305 mg, 2.5 mmol) in 20 mL of anhydrous DMF. The reaction mixture was left to stir at ambient temperature for 18 hrs. Then it was poured into ca. 300 mL of $H_2O$ and extracted with EtOAc (4×100 mL). The combined organic solutions were washed with brine (2×100 mL), dried over anhydrous $Na_2SO_4$ and filtered. Solvent was removed in vacuo to give a reddish oily residue.

The residue was re-dissolved in 10 mL of DMF, filtered through 0.2 u syringe filter and purified by reverse-phase preparative HPLC in $CH_3CN/H_2O$ system containing 0.05% of TFA. Fractions, containing the product, were combined and poured into EtOAc (100 mL). The solution was treated with saturated aqueous $NaHCO_3$ (2×30 mL), washed with brine (2×30 mL), dried over anhydrous $Na_2SO_4$ and filtered. The filtrate was concentrated in vacuo to give the title compound as a beige powder (184 mg, 12% yield).

$^1$H NMR (500 MHz, DMSO-$d_6$): δ 1.75 (br s, 4H), 2.74 (br s, 4H), 2.98 (br s, 2H), 4.12 (br s, 2H), 6.95 (d, J=9.1 Hz, 2H), 7.55 (d, J=8.8 Hz, 1H), 7.66 (d, J=9.1 Hz, 2H), 7.77 (dd, J=8.8, 2.6 Hz, 1H), 7.80 (d, J=7.8 Hz, 1H), 7.98 (d, J=7.8 Hz, 1H), 8.13 (d, J=2.5 Hz, 1H), 8.31 (d, J=8.0 Hz, 1H), 8.32 (s, 1H), 8.99 (s, 2H), 10.05 (s, 1H), 10.13 (s, 1H), 10.73 (s, 1H). MS (ES+): m/z 624, 625, 627, 628 (M+H)$^+$.

EXAMPLE 122

Synthesis of Methyl 2-{[3-(2-pyrrolidin-1-ylethoxy)phenyl]amino}pyrimidine-5-carboxylate (Intermediate 63)

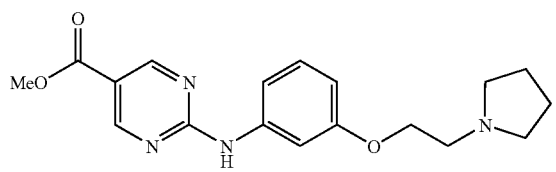

63

Two 20 mL microwave vials were each charged with methyl 2-aminopyrimidine-5-carboxylate (460.0 mg, 3.0 mmol), 1-[2-(3-bromo-phenoxy)-ethyl]-pyrrolidine (811.0 mg, 3.0 mmol), $Pd_2(dba)_3$ (110.0 mg, 0.12 mmol), XantPhos (208.3 mg, 0.36 mmol), $Cs_2CO_3$ (1.95 g, 6.0 mmol) and anhydrous dioxane (20 mL). The mixture was purged with argon gas for 15 min, then sealed and irradiated in a microwave (Initiator, Biotage) at 180° C. for 60 min. After cooling to room temperature, the cap was removed and the reaction mixtures were combined and partitioned between EtOAc and $H_2O$. The aqueous layer was extracted with EtOAc (3×100 mL). Combined EtOAc solutions were washed with $H_2O$ (2×100 mL), brine (2×100 mL) and dried over anhydrous $Na_2SO_4$. The resulting solution was concentrated in vacuo with ca. 15 g of silica gel. The loaded silica gel was taken to the ISCO system for further purification (80 g column, solid method, 0% to 20% MeOH gradient in DCM, 40 min method). Fractions, containing the product, were combined and concentrated in vacuo to give reddish oil. The oil was re-crystallized from 10 mL of CH$_3$CN to give the title compound as a light-yellow solid (1.07 g, 35% yield).

EXAMPLE 123

Synthesis of 2-{[3-(2-Pyrrolidin-1-ylethoxy)phenyl] amino}pyrimidine-5-carboxylic acid (Intermediate 64)

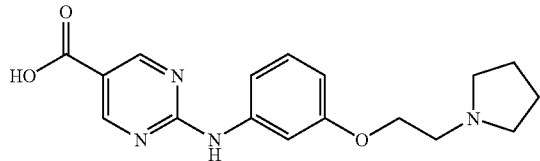

To a suspension of intermediate 63 (1.05 g, 3.07 mmol) in 4 ml of CH$_3$CN was added a solution of LiOH (147.3 mg, 6.15 mmol) in 4 mL of H$_2$O. The reaction mixture was stirred at ambient temperature for 18 hrs. The progress of the reaction was monitored by TLC and LC/MS. Then 12 N HCl (0.51 mL, 6.15 mmol) was added and solvent was removed in vacuo to give a beige solid. 50 mL of toluene were added and solvent was removed in vacuo until all solids were dry. Toluene addition and removal process was repeated three times to ensure a complete azeotropic removal of H$_2$O. The solid was dried in high vacuum for 1 hr and taken to the next step without further purification.

EXAMPLE 124

Synthesis of N-(2-Chloro-5-{[3-(trifluoromethyl) benzoyl]amino}phenyl)-2-{[3-(2-pyrrolidin-1-ylethoxy)phenyl]amino}pyrimidine-5-carboxamide (Compound LVII)

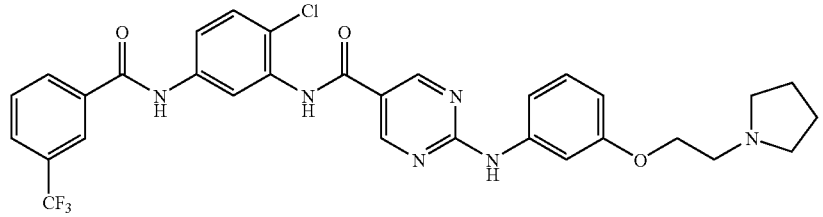

100 mL round-bottom flask was charged with intermediate 64 (1.0 g, 3.07 mmol) and 2.0 M solution of thionyl chloride in DCM (31 mL, 62.0 mmol, 20 equiv.) under argon atmosphere. A reflux condenser was inserted and the reaction mixture was refluxed under argon atmosphere for 6 hrs. Then ca. 100 mL of anhydrous toluene were added and the reaction mixture was concentrated in vacuo down to ca. 50 mL of the total volume. This process was repeated three times. Then to the resulting solution of 2-{[3-(2-pyrrolidin-1-ylethoxy)phenyl]amino}pyrimidine-5-carboxyl chloride in ca. 50 mL of anhydrous toluene was added a solution of intermediate 60 (0.966 g, 3.07 mmol) and DMAP (0.375 g, 3.07 mmol) in 30 mL of anhydrous DMF. The reaction mixture was left to stir at ambient temperature for 2 days. Then it was poured into ca. 300 mL of H$_2$O and extracted with EtOAc (4×50 mL). The combined organic solutions were washed with brine (2×100 mL), dried over anhydrous Na$_2$SO$_4$ and filtered. Solvent was removed in vacuo to give a dark-yellow residue. The residue was re-dissolved in 10 mL of DMF, filtered through 0.2 u syringe filter and purified by reverse-phase preparative HPLC in CH$_3$CN/H$_2$O system containing 0.05% of TFA. Fractions, containing the product, were combined and poured into EtOAc (100 mL). The solution was treated with saturated aqueous NaHCO$_3$ (2×30 mL), washed with brine (2×30 mL), dried over anhydrous Na$_2$SO$_4$ and filtered. The filtrate was concentrated in vacuo to give the title compound as a white powder (288 mg, 15% yield).

$^1$H NMR (500 MHz, DMSO-d$_6$): δ 1.78 (br s, 4H), 2.82 (br s, 4H), 3.08 (br s, 2H), 4.15 (br s, 2H), 6.65 (dd, J=8.2, 2.0 Hz, 1H), 7.24 (t, J=8.2 Hz, 1H), 7.37 (d, J=9.2 Hz, 1H), 7.54 (s, 1H), 7.56 (d, J=8.8 Hz, 1H), 7.76-7.81 (m, 2H), 7.98 (d, J=7.8 Hz, 1H), 8.14 (d, J=2.4 Hz, 1H), 8.30 (d, J=8.0 Hz, 1H), 8.32 (s, 1H), 9.05 (s, 2H), 10.18 (s, 1H), 10.21 (s, 1H), 10.73 (s, 1H). MS (ES+): m/z 624, 625, 627, 628 (M+H)$^+$.

EXAMPLE 125

Synthesis of Methyl 2-(pyridin-3-ylamino)pyrimidine-5-carboxylate (Intermediate 65)

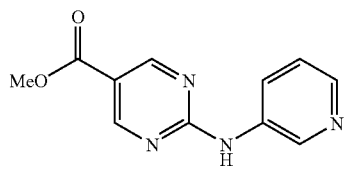

Two 20 mL microwave vials were each charged with methyl 2-aminopyrimidine-5-carboxylate (460.0 mg, 3.0 mmol), 3-bromopyridine (711.0 mg, 4.5 mmol), Pd$_2$(dba)$_3$ (110.0 mg, 0.12 mmol), XantPhos (208.3 mg, 0.36 mmol), Cs$_2$CO$_3$ (1.95 g, 6.0 mmol) and anhydrous dioxane (20 mL). The mixture was purged with argon gas for 15 min, then sealed and irradiated in a microwave (Initiator, Biotage) at 180° C. for 60 min. After cooling to room temperature, the cap was removed and the reaction mixtures were combined and diluted with ca. 100 mL of EtOAc. The resulting solution was concentrated in vacuo with ca. 15 g of silica gel. The loaded silica gel was taken to the ISCO system for further purification (80 g column, solid method, 0% to 20% MeOH gradient in DCM, 40 min method). Fractions, containing the product, were combined and concentrated in vacuo to give a reddish solid. The solid was washed with EtOAc (1×10 mL), Et$_2$O (3×40 mL) and dried in vacuo to give the title compound as a fine beige powder (0.98 g, 47% yield).

$^1$H NMR (500 MHz, DMSO-d$_6$): δ 3.83 (s, 3H), 7.36 (dd, J=8.4, 4.8 Hz, 1H), 8.17-8.20 (m, 1H), 8.25 (dd, J=4.6, 1.3 Hz, 1H), 8.89 (d, J=2.5 Hz, 1H), 8.92 (s, 2H), 10.48 (s, 1H).

EXAMPLE 126

Synthesis of
2-(Pyridin-3-ylamino)pyrimidine-5-carboxylic acid
(Intermediate 66)

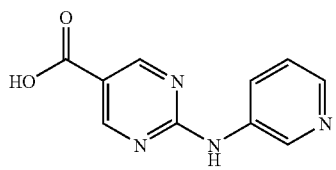

To a suspension of intermediate 65 (0.98 g, 4.26 mmol) in 30 mL of CH$_3$CN was added a solution of LiOH (238.0 mg, 9.94 mmol) in 30 mL of H$_2$O. The reaction mixture was stirred at ambient temperature for 18 hrs. The progress of the reaction was monitored by TLC and LC/MS. Then 12 N HCl (0.83 mL, 9.94 mmol) was added and solvent was removed in vacuo to give a beige solid. 100 mL of toluene were added and solvent was removed in vacuo until all solids were dry. Toluene addition and removal process was repeated three times to ensure a complete azeotropic removal of H$_2$O. The solid was dried in high vacuum for 1 hr and taken to the next step without further purification.

EXAMPLE 127

Synthesis of N-[2-Chloro-5-({[3-(trifluoromethyl)
phenyl]carbonyl}amino)phenyl]-2-(pyridin-3-
ylamino)pyrimidine-5-carboxamide (Compound
LVIII)

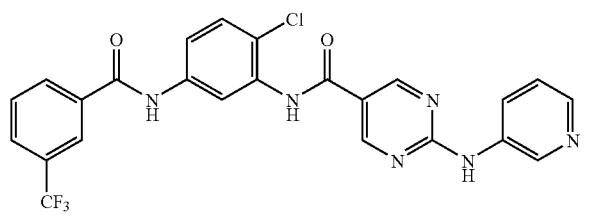

150 mL round-bottom flask was charged with intermediate 66 (0.92 g, 4.26 mmol) and 2.0 M solution of thionyl chloride in DCM (22 mL, 42.6 mmol, 10 equiv.) under argon atmosphere. A reflux condenser was inserted and the reaction mixture was refluxed under argon atmosphere for 6 hrs. Then ca. 100 mL of anhydrous toluene were added and the reaction mixture was concentrated in vacuo down to ca. 50 mL of the total volume. This process was repeated three times. Then to the resulting solution of 2-(pyridin-3-ylamino)pyrimidine-5-carboxyl chloride in ca. 80 mL of anhydrous toluene was added a solution of intermediate 60 (1.34 g, 4.26 mmol) and DMAP (0.52 g, 4.26 mmol) in 30 mL of anhydrous DMF. The reaction mixture was left to stir at ambient temperature for 2 days. Then it was poured into ca. 300 mL of H$_2$O and extracted with EtOAc (4×50 mL). The combined organic solutions were washed with brine (2×100 mL), dried over anhydrous Na$_2$SO$_4$ and filtered. Solvent was removed in vacuo to give a dark-yellow residue. The residue was re-dissolved in 10 mL of DMF, filtered through 0.2 u syringe filter and purified by reverse-phase preparative HPLC in CH$_3$CN/H$_2$O system containing 0.05% of TFA. Fractions, containing the product, were combined and poured into EtOAc (100 mL). The solution was treated with saturated aqueous NaHCO$_3$ (2×30 mL), washed with brine (2×30 mL), dried over anhydrous Na$_2$SO$_4$ and filtered. The filtrate was concentrated in vacuo to give the title compound as a white powder (463.0 mg, 21% yield).

$^1$H NMR (500 MHz, DMSO-d$_6$): δ 7.38 (dd, J=8.1, 4.7 Hz, 1H), 7.57 (dd, J=8.8, 0.8 Hz, 1H), 7.73-7.75 (m, 1H), 7.79 (t, J=7.8 Hz, 1H), 7.98 (d, J=7.8 Hz, 1H), 8.14 (dd, J=2.4, 0.7 Hz, 1H), 8.22-8.25 (m, 2H), 8.28 (d, J=7.9 Hz, 1H), 8.31 (s, 1H), 8.94 (d, J=1.8 Hz, 1H), 9.06 (s, 2H), 10.16 (s, 1H), 10.39 (s, 1H), 10.66 (s, 1H). MS (ES+): m/z 512, 513, 515 (M+H)$^+$.

EXAMPLE 128

Synthesis of 2-Chloro-N-[2-({4-[2-(1-oxidopyrroli-
din-1-yl)ethoxy]phenyl}amino)pyrimidin-5-yl]-5-({
[3-(trifluoromethyl)phenyl]carbonyl}amino)benza-
mide (Compound LIX)

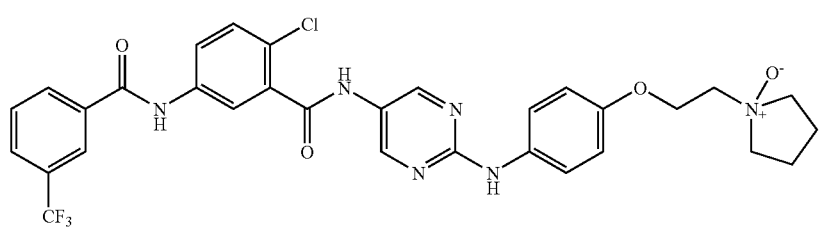

To a solution of compound XL described in Example 80 above (200 mg, 0.32 mmol) in 30 mL of DCM at 0° C. was added mCPBA (86 mg, 0.38 mmol, 77% purity). The reaction mixture was stirred at 0° C. for 2 hrs, and then it was allowed to warm up to ambient temperature and stirred at ambient temperature for 18 hrs. Then solvent was removed in vacuo and the residue was re-dissolved in 4 mL of DMF, filtered through 0.2 u syringe filter and purified by reverse-phase preparative HPLC in CH$_3$CN/H$_2$O system containing 0.05% of TFA. Fractions, containing the product, were combined and poured into EtOAc (100 mL). The solution was treated with saturated aqueous NaHCO$_3$ (1×50 mL), washed with brine (2×50 mL), dried over anhydrous Na$_2$SO$_4$ and filtered. The filtrate was concentrated in vacuo to give the title compound as an off-white powder (112.0 mg, 55% yield).
$^1$H NMR (500 MHz, DMSO-d$_6$): δ 1.90 (br s, 2H), 2.10 (br s, 2H), 3.29 (br s, 4H), 3.45 (br s, 4H), 3.65 (br s, 2H), 4.45 (t, J=4.6 Hz, 2H), 6.91 (d, J=9.1 Hz, 2H), 7.58 (d, J=8.8 Hz, 1H), 7.64 (d, J=9.0 Hz, 2H), 7.80 (t, J=7.8 Hz, 1H), 7.96-7.99 (m, 2H), 8.08 (d, J=2.5 Hz, 1H), 8.32 (d, J=8.0 Hz, 1H), 8.34 (s, 1H), 8.74 (s, 2H), 9.53 (s, 1H), 10.77 (s, 1H), 10.87 (s, 1H). MS (ES+): m/z 641, 643, 644 (M+H)$^+$.

EXAMPLE 129

Synthesis of (4-Methoxy-phenyl)-(5-nitro-pyrimidin-2-yl)-amine (Intermediate 67)

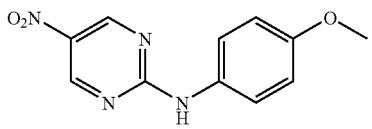

In a dry 50 mL round bottom flask 5-nitro-pyrimidin-2-ylamine (1.16 g, 8.3 mmol, 1 equiv), 4-bromo anisole (1.3 mL, 10.4 mmol, 1.25 equiv), cesium carbonate (5.4 g, 16.6 mmol, 2 equiv), 4,5-bis(diphenylphosphino)-9,9-dimethyl xanthene (0.479 g, 0.83 mmol, 0.1 equiv) and tris(dibenzylideneacetone) dipalladium (0.304 g, 0.33 mmol, 0.04 equiv) were combined. Reactants were flushed with argon, diluted with dioxane (15 mL) and outfitted with reflux condenser. Reaction was heated to reflux for 18 hours. Reaction was then filtered hot and solvents were evaporated to provide dark solids. Silica gel chromatography (1:4 EtOAc/Hexanes) provided desired product. Yellow powder (0.6 g, 30% yield). R$_f$=0.39 (20% EtOAc/Hexanes).

EXAMPLE 130

Synthesis of N-(4-Methoxy-phenyl)-pyrimidine-2,5-diamine (Intermediate 68)

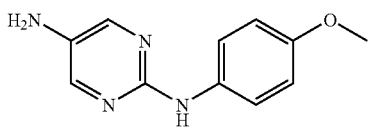

Intermediate 67 (0.3 g, 1.22 mmol, 1 equiv) was combined with 10% palladium on carbon (0.2 g) and flushed with argon. Reactants were then diluted with methanol (30 mL) and reaction atmosphere was evacuated and replaced with hydrogen. Hydrogen balloon was affixed and reaction was allowed to stir for 4 hours. Argon was then bubbled through reaction mixture and contents were filtered though a pad of Celite™. Solvents were evaporated to provide crude product. Trituration with heptane followed by filtration provided desired amine. Beige solids (0.245 g, 93% yield).

EXAMPLE 131

Synthesis of 2-Chloro-N-[2-(4-methoxy-phenylamino)-pyrimidin-5-yl]-5-(3-trifluoromethyl-benzoylamino)-benzamide (Compound LX)

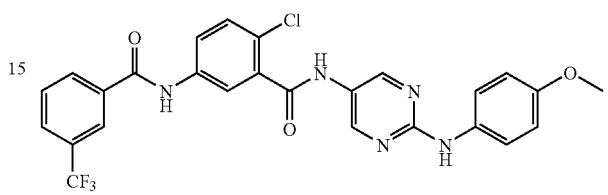

2-Chloro-5-(3-trifluoromethyl-benzoylamino)-benzoic acid (0.524 g, 1.53 mmol, 1.1 equiv) was combined with 2-chloro-4,6-dimethoxy-1,3,5-triazine (CDMT) (0.305 g, 1.74 mmol, 1.25 equiv) and diluted with DCM (10 mL). This was immediately treated with 4-methyl morpholine (0.458 mL, 4.16 mmol, 3 equiv) and allowed to stir at ambient temperature for 1 hour. Intermediate 68 (0.3 g, 1.38 mmol, 1 equiv) was then added in one portion. Stirring was continued overnight. After 18 h, reaction solvents were removed and resulting crude solids were purified via silica gel chromatography. Eluting with 1:1 EtOAc in Hexanes afforded desired product. Beige solids (0.19 g, 26%).
$^1$H NMR (DMSO-d$_6$): δ 3.70 (s, 1H), 6.88 (d, J=9.0 Hz, 2H), 7.59-7.62 (m, 3H), 7.81 (t, J=7.9 Hz, 1H), 7.95 (dd, J=8.8, 2.6 Hz, 1H), 8.00 (d, J=8.0 Hz, 1H), 8.04 (d, J=2.6 Hz, 1H), 8.28 (d, J=8.0 Hz, 1H), 8.32 (s, 1H), 8.72 (s, 2H), 9.45 (s, 1H), 10.6 (s, 1H), 10.7 (s, 1H).

EXAMPLE 132

Synthesis of 2-Chloro-N-[2-(4-hydroxy-phenylamino)-pyrimidin-5-yl]-5-(3-trifluoromethyl-benzoylamino)-benzamide (Compound LXI)

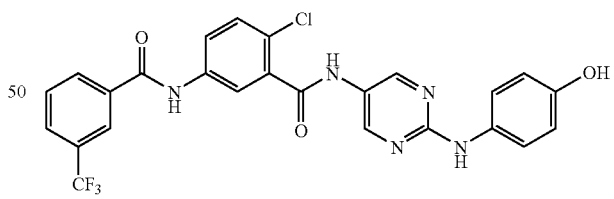

A stirring solution of compound LX (0.142 g, 0.264 mmol, 1 equiv) in DCM (10 mL) was treated with a 1M solution of BBr$_3$ in DCM (1.6 mL, 1.6 mmol, 6 equiv). After 6 hours reaction was quenched by adding a saturated sodium bicarbonate solution (ca. 5 mL) and sonicating for 2 minutes. Resulting orange-yellow precipitate was collected and dried, 0.125 g (90%).
$^1$H NMR (DMSO-d$_6$): δ 6.69 (d, J=9.0 Hz, 2H), 7.46 (d, J=9.0 Hz, 2H), 7.59 (d, J=8.82 Hz, 1H), 7.81 (t, J=7.9 Hz, 1H), 7.95 (dd, J=8.8, 2.6 Hz, 1H), 8.00 (d, J=8.0 Hz, 1H), 8.04 (d, J=2.6 Hz, 1H), 8.28 (d, J=8.0 Hz, 1H), 8.32 (s, 1H), 8.69 (s, 2H), 9.34 (br s, 1H), 10.6 (s, 1H), 10.7 (s, 1H).

EXAMPLE 133

Synthesis of Benzoic acid 4-{5-[2-chloro-5-(3-trifluoromethyl-benzoylamino)-benzoylamino]-pyrimidin-2-ylamino}-phenyl ester (Compound LXII)

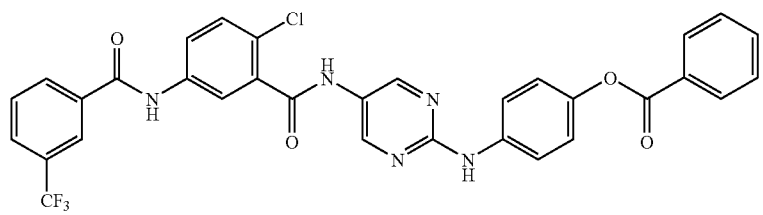

A slurry of compound LXI (0.152 g, 0.288 mmol, 1 equiv) in DCM (45 mL) was treated with triethylamine (0.088 mL, 0.63 mmol, 2.2 equiv) and stirred vigorously. A separate solution of benzoyl chloride (0.037 g, 0.26 mmol, 0.9 equiv) in DCM (6 mL) was then slowly added with stirring. After 3 hours, solvents were removed and crude material purified on silica gel column. White solid, 0.022 g (12%).

$^1$H NMR (DMSO-$d_6$): δ 7.21 (d, J=9.1 Hz, 2H), 7.59-7.62 (m, 3H), 7.73-7.78 (m, 1H), 7.81-7.83 (m, 3H), 7.96 (dd, J=8.8, 2.6 Hz, 1H), 8.00 (d, J=8.0 Hz, 1H), 8.05 (d, J=2.6 Hz, 1H), 8.13 (d, J=8.0 Hz, 2H), 8.29 (d, J=8.0 Hz, 1H), 8.32 (s, 1H), 8.8 (s, 2H), 9.79 (s, 1H), 10.6 (s, 1H), 10.7 (s, 1H).

EXAMPLE 134

Synthesis of 3-(3-(Trifluoromethyl)phenylcarbamoyl)benzoic acid (Intermediate 69)

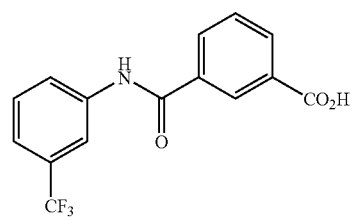

N-(3-Dimethylaminopropyl)-N'-ethylcarbodiimide hydrochloride (1.34 g, 7 mmol) was added to a stirring solution of isophthalic acid (1.66 g, 10 mmol) and 3-(trifluoromethyl)benzenamine (0.8 g, 5 mmol) in anhydrous $CH_2Cl_2$ (10 mL) and DMF (10 mL). The mixture was stirred at room temperature under argon for 2 h. The solvent was removed under reduced pressure and recrystalized from water to afford the title compound as a white solid after washed by $CHCl_3$ (1.5 g, 49%).

EXAMPLE 135

Synthesis of $N^1$-(2-(4-(3-(Pyrrolidin-1-yl)propylsulfonyl)phenylamino)pyrimidin-5-yl)-$N^3$-m-tolyl-isophthalamide (Compound LXIII)

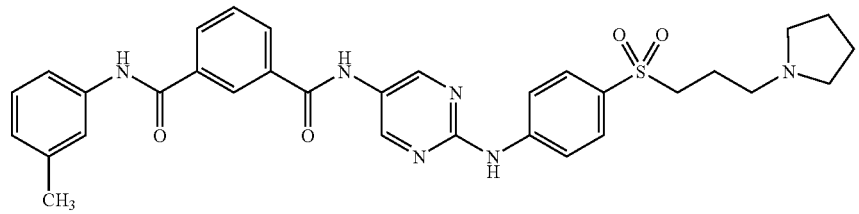

N-(3-Dimethylaminopropyl)-N'-ethylcarbodiimide hydrochloride (220 mg, 1.2 mmol) and 4-dimethylaminopyridine (200 mg) was added to a stirring solution of intermediate 69 (90 mg, 0.3 mmol) and N-[4-(3-pyrrolidin-1-yl-propane-1-sulfonyl)-phenyl]-pyrimidine-2,5-diamine (100 mg, 0.3 mmol) in anhydrous $CH_2Cl_2$ (5 mL) and DMF (2 mL). The mixture was stirred at room temperature under argon for 8 h. The organic solvent was removed and the crude product was purified by silica gel column with 20% $CH_3OH/CHCl_3$ as an eluent. The off-white solid was isolated by washed with acetone and dried in vacuo as an HCl salt (80 mg, 44%).

$^1$H NMR (DMSO-$d_6$) δ 1.70-2.20 (m, 6H), 2.80-3.80 (m, 8H), 7.62 (d, J=8.8 Hz, 1H), 7.48 (d, J=7.6 Hz, 1H), 7.63 (t, J=7.9 Hz, 1H), 7.75 (t, J=7.7 Hz, 1H), 7.81 (d, J=8.7 Hz, 2H), 8.17 (d, J=8.4 Hz, 1H), 8.21 (d, J=7.6 Hz, 2H), 8.35 (s, 1H), 8.78 (s, 1H), 9.04 (s, 2H), 10.31 (br s, 2H), 10.88 (br s, 1H), 10.91 (br s, 1H).

EXAMPLE 136

Testing of Kinase Inhibition

The ability of compounds of the present invention to inhibit the activity of various groups of kinases was tested. Kinases that were tested are described below. All kinase reactions were conducted in 96-well plates with a final reaction volume of 50 µl.

Src Family of Kinases, abl, and Ret

Recombinant human c-Src or Yes, or Fyn, or Lck (28 ng/well, Panvera/Invitrogen, Madison Wis.), ATP (3 µM), a tyrosine kinase substrate (PTK2, 250 µM, Promega Corp., Madison Wis.), and test agents (at concentrations ranging from about 1 nM/l to about 100 µM/l), in the presence of Src kinase reaction buffer (Upstate USA, Lake Placid N.Y.). After reacting for about 90 minutes at room temperature, residual ATP was determined using a luciferase-based assay (Kinase-Glo, Promega Corp.) as a measure of kinase activity. Data from four wells were then averaged and used to determine $IC_{50}$ values for the test compounds (Prism software package, GraphPad Software, San Diego Calif.).

Growth Factor Receptor Kinases

PDGFRβ (0.16 µg/well, Panvera/Invitrogen) 500 nM ATP and the PTK2 peptide (700 µM) were combined with compound and reaction buffer as noted above for Src. The reaction was incubated for 60 minutes at 37° C., and the residual ATP concentration was determined using the luciferase-based technique also noted above.

EGFR and VEGFR2 kinase assays were similarly performed. EGFR (76 ng/well, Panvera/Invitrogen) was combined with 12.5 mg/ml poly(glu4tyr) (Sigma) and 2.5 uM ATP. VEGFR2 (14.1 U/well, Cell Signaling/ProQinase) was used with 0.3 mg/ml poly(glu4tyr) and 1.5 uM ATP. Both were incubated for 60 minutes at 37° C., and the residual ATP was measured via luminescence, per the procedure described above.

The test results for inhibition of Src kinase and Vgegfr2 kinase are presented in Table 1, and the test results for inhibition of some other kinases are presented in Table 2. The abbreviation "$IC_{50}$" means that a particular compound of the invention, when present at the specified concentration, inhibited the kinase by 50%.

TABLE 1

Test Results of Inhibition of Src and Vegfr2 Kinases by Some Compounds of the Invention

| Structure | Src $IC_{50}$ (nM) | Vegfr2 $IC_{50}$ (nM) |
| --- | --- | --- |
| [structure 1] | 4.5 | |
| [structure 2] | 1.4 | 2.9 |
| [structure 3] | 2.1 | 2.7 |
| [structure 4] | 3.9 | 13.8 |

TABLE 1-continued

Test Results of Inhibition of Src and Vegfr2 Kinases by Some Compounds of the Invention

| Structure | Src IC$_{50}$ (nM) | Vegfr2 IC$_{50}$ (nM) |
|---|---|---|
| 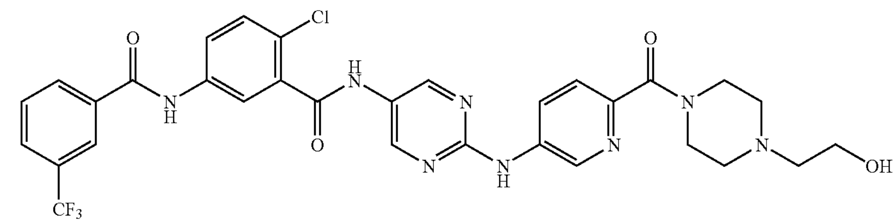 | 1.9 | 3.1 |
| 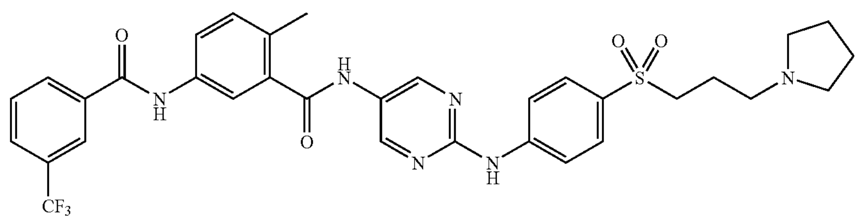 | 3.8 | 14.2 |
| 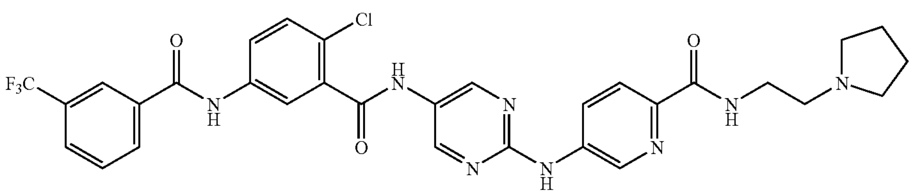 | 5 | |
| 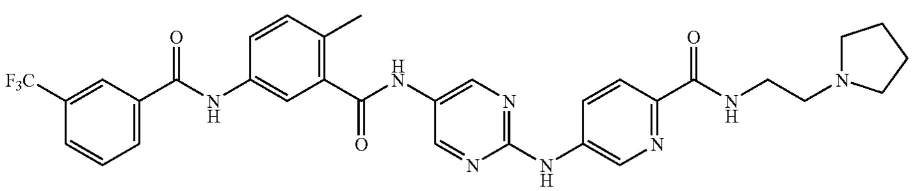 | 4.1 | 21 |
| 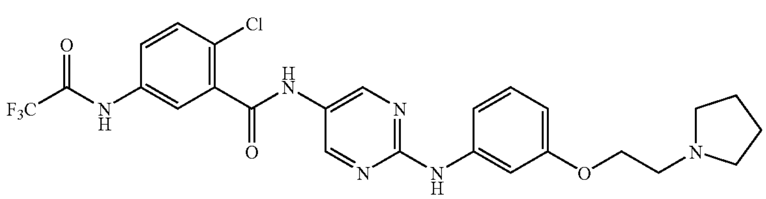 | 63.4 | |
| 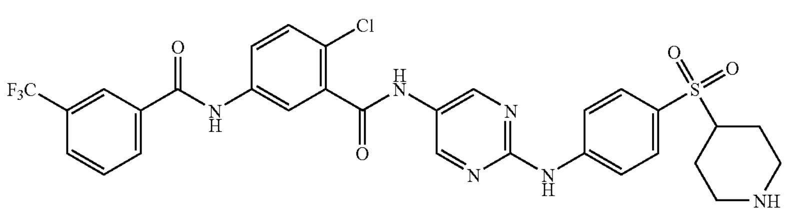 | 1.8 | 4.5 |
| 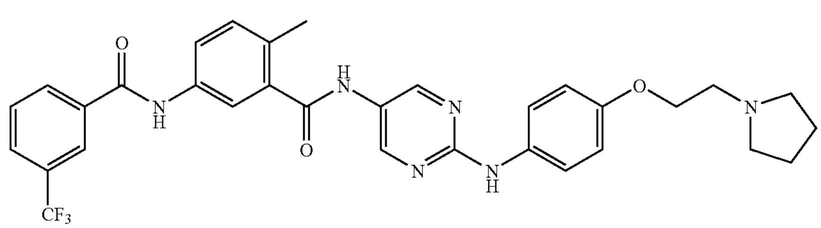 | 3.3 | 3.2 |

TABLE 1-continued

Test Results of Inhibition of Src and Vegfr2 Kinases by Some Compounds of the Invention

| Structure | Src IC$_{50}$ (nM) | Vegfr2 IC$_{50}$ (nM) |
|---|---|---|
| 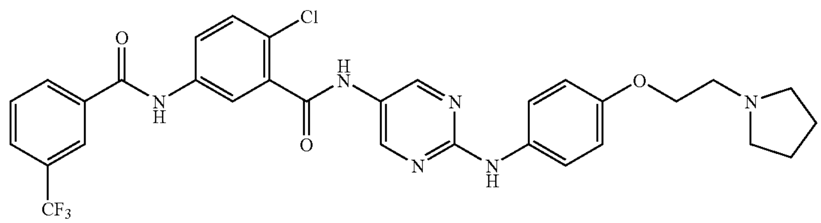 | 1.2 | 0.8 |
| 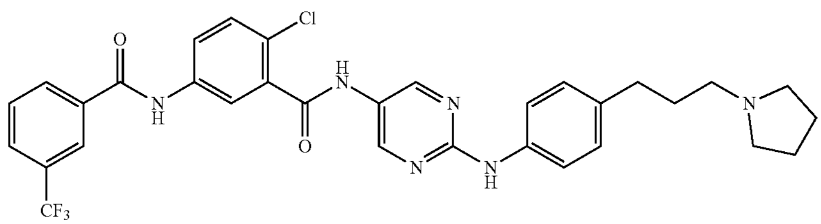 | 2.8 | 11.5 |
| 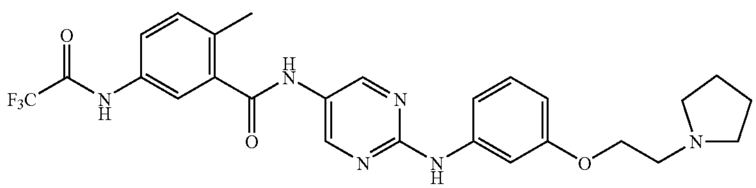 | 50.6 | |
| 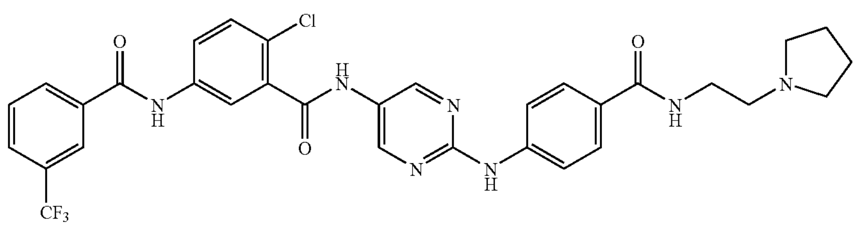 | 1.4 | 2.2 |
| 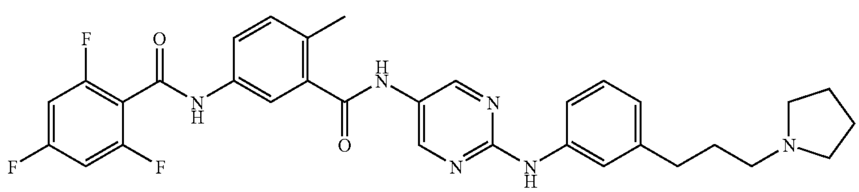 | 102 | |
| | 1.7 | |
| | 1.7 | 2.3 |

TABLE 1-continued

Test Results of Inhibition of Src and Vegfr2 Kinases by Some Compounds of the Invention

| Structure | Src IC$_{50}$ (nM) | Vegfr2 IC$_{50}$ (nM) |
|---|---|---|
| *(structure)* | 93.2 | |
| *(structure)* | 755 | |
| *(structure)* | 2.6 | 1.4 |
| *(structure)* | 4.5 | 9.6 |
| *(structure)* | 3 | 40.7 |
| *(structure)* | 11.6 | |
| *(structure)* | 1.8 | 73.1 |

TABLE 1-continued

Test Results of Inhibition of Src and Vegfr2 Kinases by Some Compounds of the Invention

| Structure | Src IC$_{50}$ (nM) | Vegfr2 IC$_{50}$ (nM) |
|---|---|---|
| 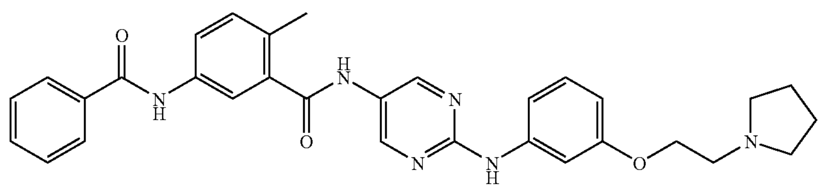 | 16.6 | |
| 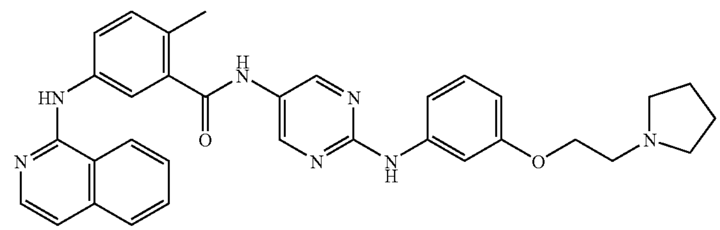 | 23.3 | 3347 |
| 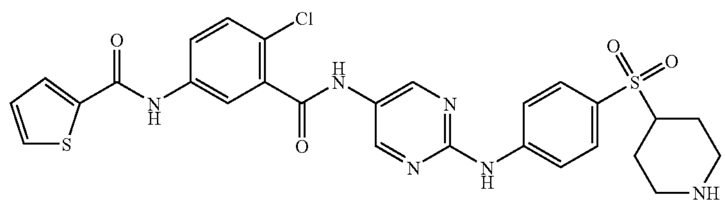 | 38.2 | |
| 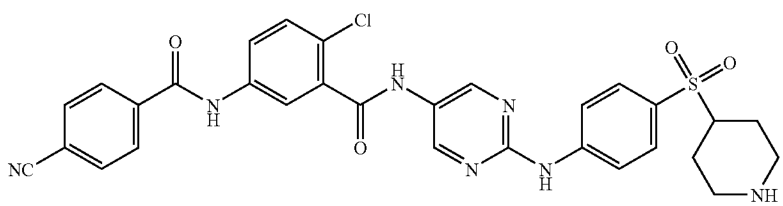 | 32 | |
| 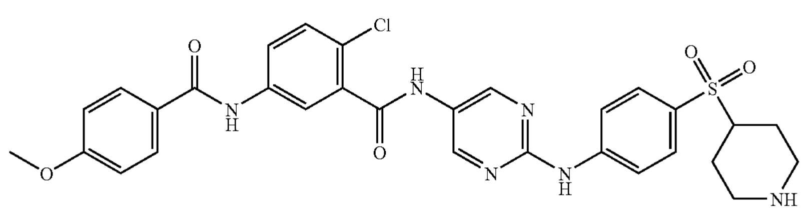 | 17.5 | |
| 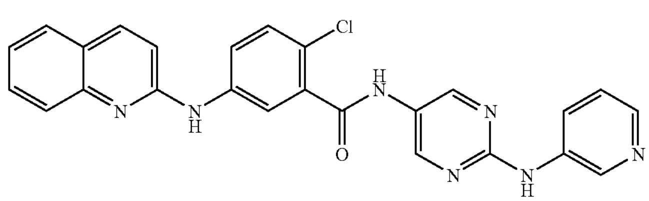 | 454 | |
| 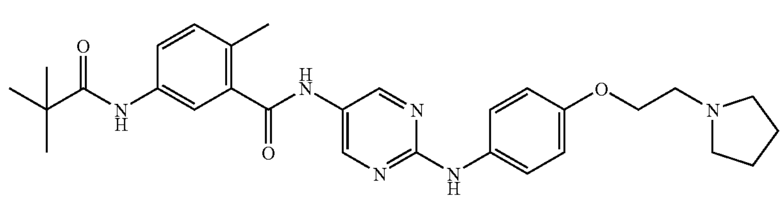 | >10000 | |

TABLE 1-continued

Test Results of Inhibition of Src and Vegfr2 Kinases by Some Compounds of the Invention

| Structure | Src IC$_{50}$ (nM) | Vegfr2 IC$_{50}$ (nM) |
|---|---|---|
| 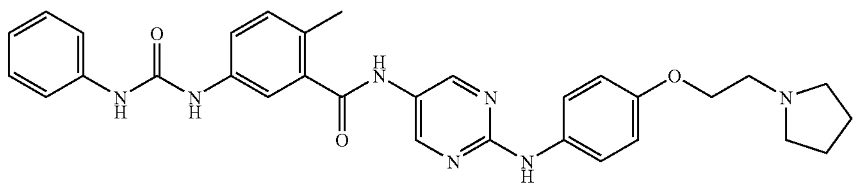 | 4.5 | 168 |
| 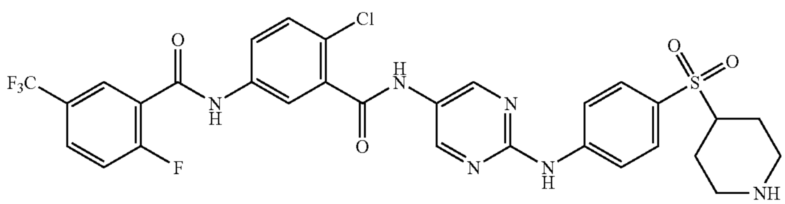 | 4.2 | 22.3 |
| 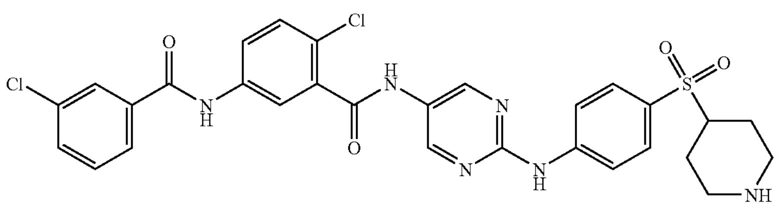 | 2.5 | 11.6 |
| 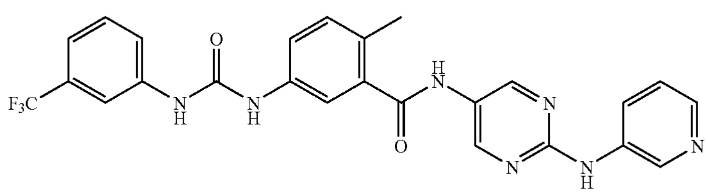 | 7.9 | 27.8 |
| 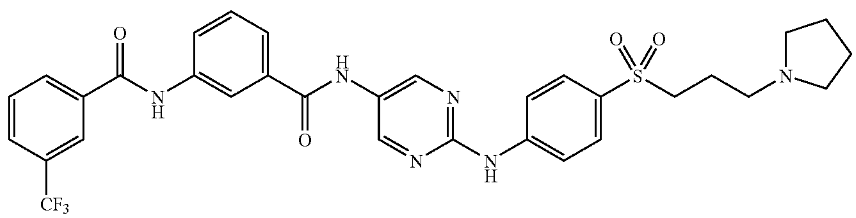 | 67.4 | |
| 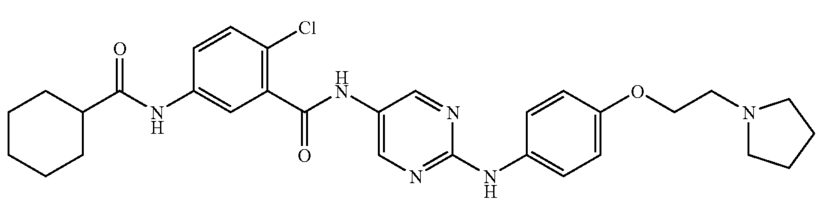 | 19.4 | |
| 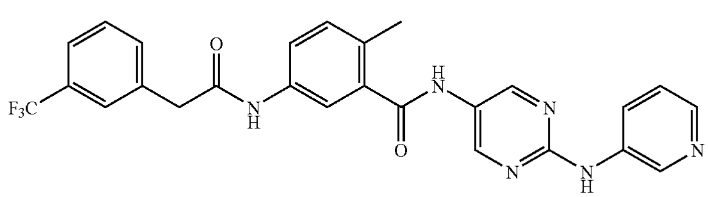 | 56.9 | |

TABLE 1-continued

Test Results of Inhibition of Src and Vegfr2 Kinases by Some Compounds of the Invention

| Structure | Src IC$_{50}$ (nM) | Vegfr2 IC$_{50}$ (nM) |
|---|---|---|
| 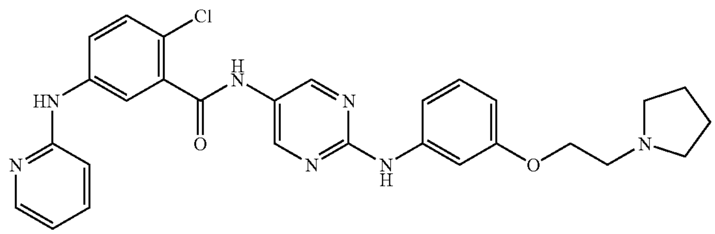 | 169 | |
| 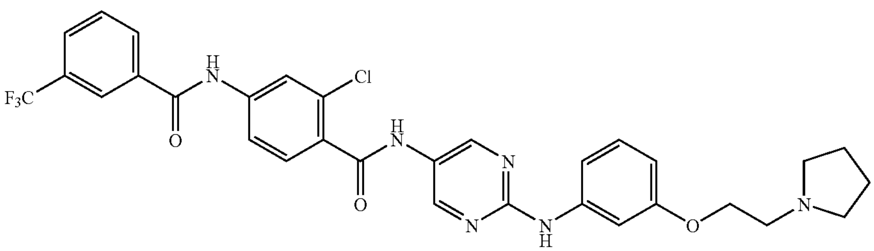 | 65.7 | |
| 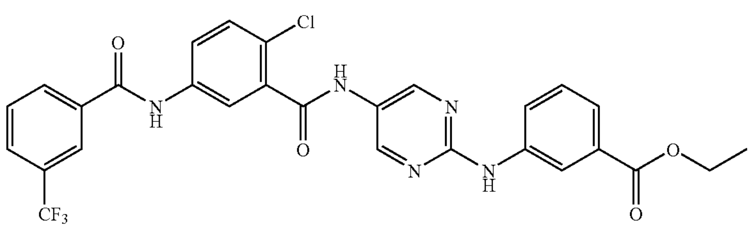 | 13.4 | |
| 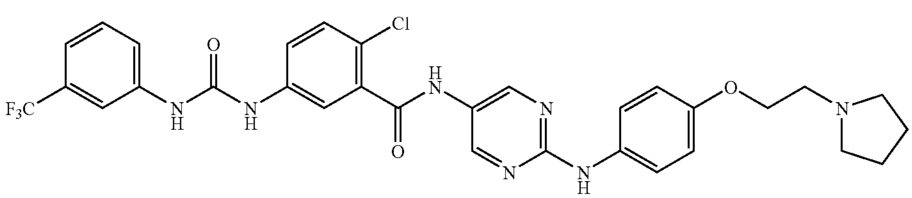 | 2.2 | 7.1 |
| 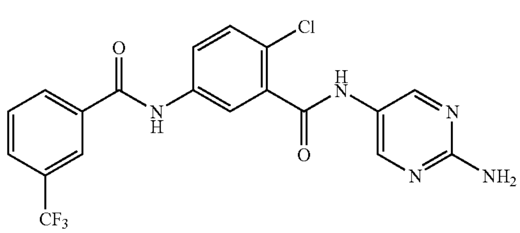 | 72 | |
| 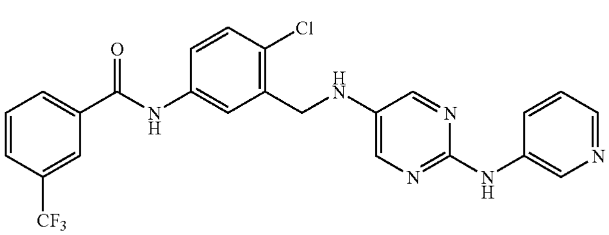 | 10.2 | 2.1 |

TABLE 1-continued

Test Results of Inhibition of Src and Vegfr2 Kinases by Some Compounds of the Invention

| Structure | Src IC$_{50}$ (nM) | Vegfr2 IC$_{50}$ (nM) |
|---|---|---|
| *[structure]* | 2600 | |
| *[structure]* | 407 | |
| *[structure]* | >10000 | |
| *[structure]* | 77.5 | |
| *[structure]* | 4 | 2.1 |
| *[structure]* | 3.3 | 12 |
| *[structure]* | 4.7 | 5.4 |

TABLE 1-continued

Test Results of Inhibition of Src and Vegfr2 Kinases by Some Compounds of the Invention

| Structure | Src IC$_{50}$ (nM) | Vegfr2 IC$_{50}$ (nM) |
|---|---|---|
| 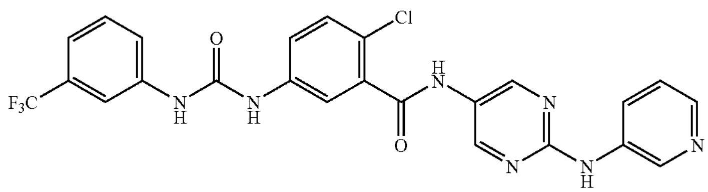 | 14.2 | 20.1 |
| 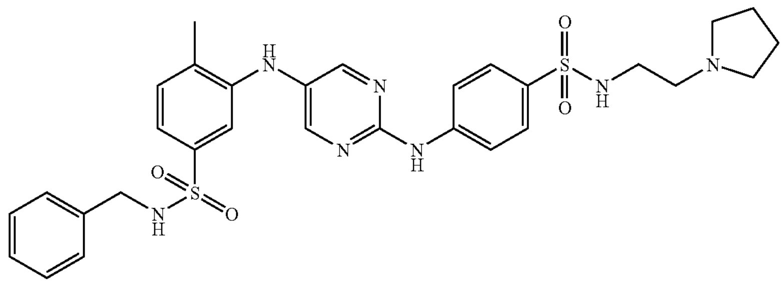 | 1300 | |
| 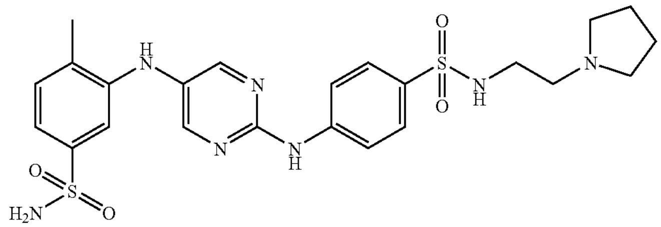 | ~10000 | |
| 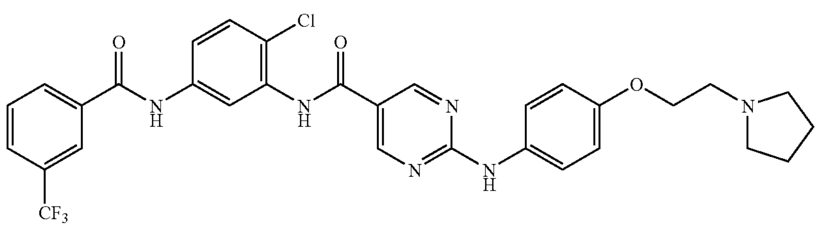 | 50 | 43 |
| 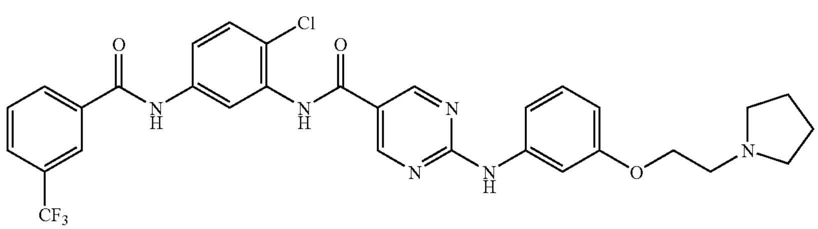 | 67 | 149 |
| 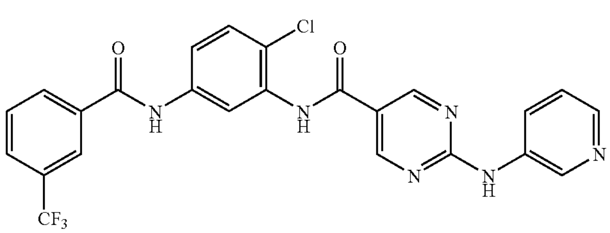 | 86 | 178 |

: TABLE 1-continued

Test Results of Inhibition of Src and Vegfr2 Kinases by Some Compounds of the Invention

| Structure | Src IC$_{50}$ (nM) | Vegfr2 IC$_{50}$ (nM) |
|---|---|---|
| | | |
| 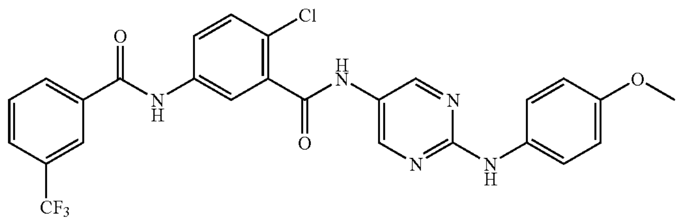 | 12 | 23 |
| 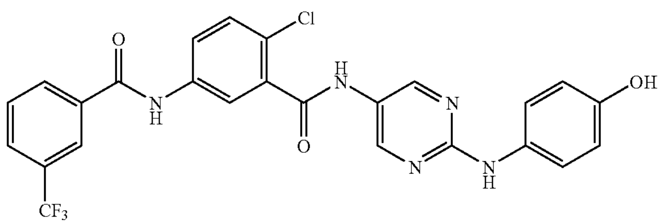 | 19 | 15 |
| 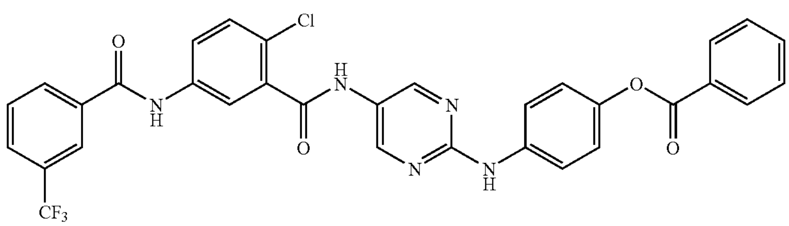 | 647 | 361 |
| | | 164 |

TABLE 2

Test Results of Inhibition of Various Kinases by Some Compounds of the Invention

| Structure | Yes IC$_{50}$ | Fyn IC$_{50}$ | Lck IC$_{50}$ | Abl IC$_{50}$ | PDGF R IC$_{50}$ | EGF R IC$_{50}$ | RET IC$_{50}$ |
|---|---|---|---|---|---|---|---|
| (structure 1) | | | | | | | 16 |
| (structure 2) | | 3 | | | | | |
| (structure 3) | 0.52 | | 1.7 | 1.1 | | | |
| (structure 4) | 0.93 | | 3.8 | | | | |
| (structure 5) | | | | | 154 | | |
| (structure 6) | 0.9 | | 4.5 | 0.2 | | | |
| (structure 7) | 1.3 | | 5.1 | 5.5 | | | |

TABLE 2-continued

Test Results of Inhibition of Various Kinases by Some Compounds of the Invention

| Structure | Yes IC$_{50}$ | Fyn IC$_{50}$ | Lck IC$_{50}$ | Abl IC$_{50}$ | PDGF R IC$_{50}$ | EGFR IC$_{50}$ | RET IC$_{50}$ |
|---|---|---|---|---|---|---|---|
| 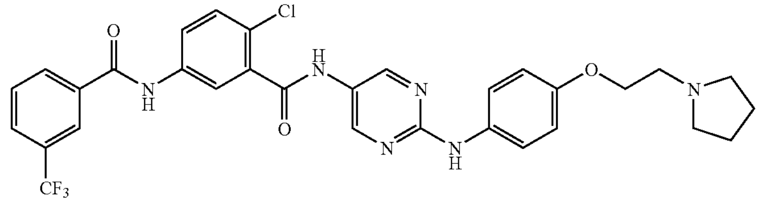 | 0.46 | 3.6 | 2.2 | 1.8 | 0.67 | 98 | |
| 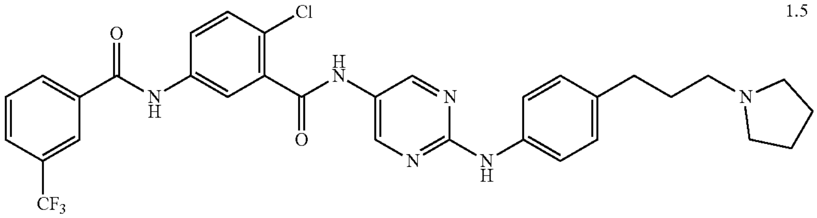 | 1.5 | | 15.5 | 3.8 | | | |
| | | | | 126 | | | |
| 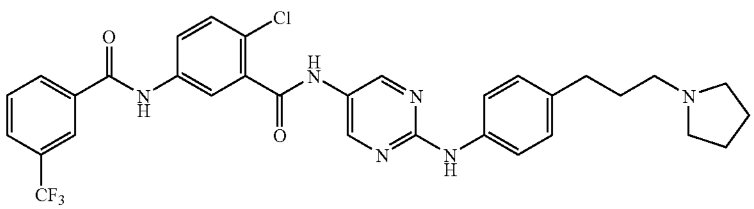 | 0.44 | | 2 | 1 | | 124 | |
| 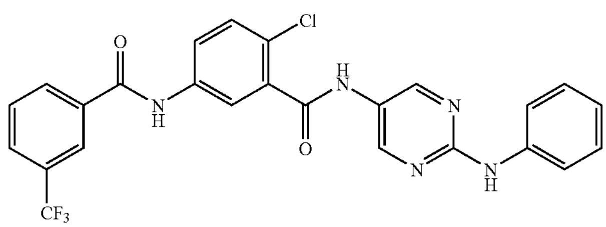 | 4.2 | | 32.2 | | | | |
| | | | 5.9 | | | | |
| 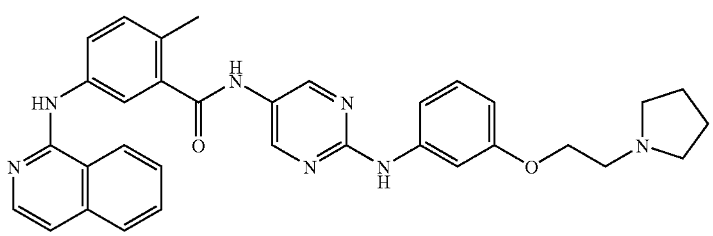 | 22.2 | | 309 | | | | |

TABLE 2-continued
Test Results of Inhibition of Various Kinases by Some Compounds of the Invention
| Structure | Yes IC$_{50}$ | Fyn IC$_{50}$ | Lck IC$_{50}$ | Abl IC$_{50}$ | PDGF R IC$_{50}$ | EGF R IC$_{50}$ | RET IC$_{50}$ |
|---|---|---|---|---|---|---|---|
| 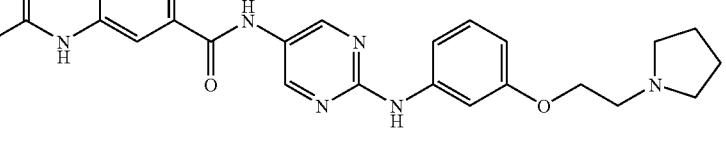 | 2.5 | 22.4 | | 1.4 | | 558 | |
TABLE 3
Test results with cellular data using human retinal micro vascular endothelial cells (hRMVEC) for selected compounds of the invention
| STRUCTURE | HRMVEC EC50 |
|---|---|
| 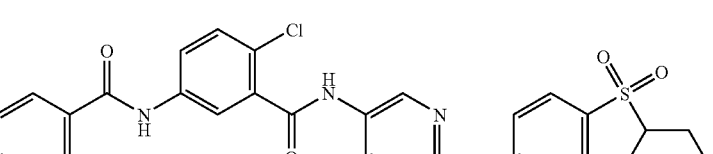 | 69 nM |
| 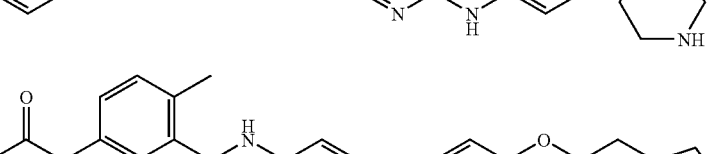 | 1153 nM |
| 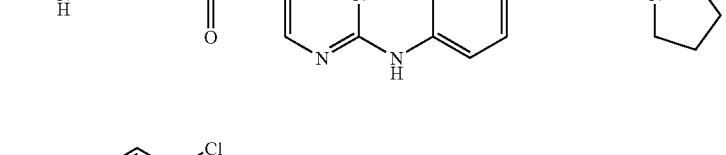 | 199 nM |
| 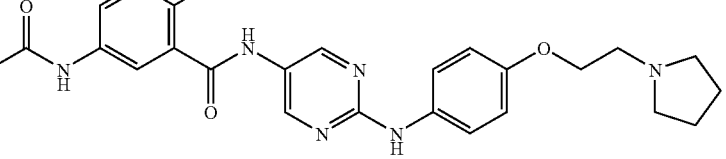 | 30 nM |
| 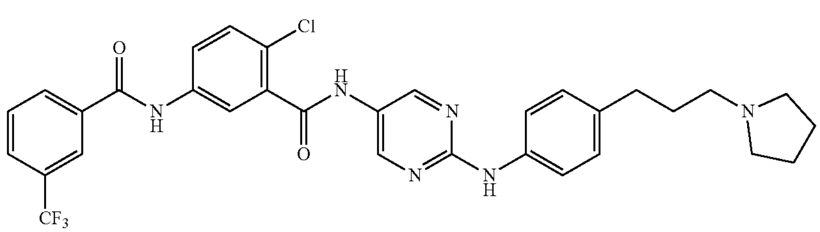 | 41 nM |

TABLE 3-continued

Test results with cellular data using human retinal micro vascular
endothelial cells (hRMVEC) for selected compounds of the invention

| STRUCTURE | HRMVEC EC50 |
|---|---|
| [Structure: chlorophenyl-bis-amide with pyrimidine-pyridine and CF3-benzamide] | 68 nM |

EXAMPLE 137

Testing of in Vivo Activity Using Compound XL

The following methods were used for testing of in vivo activity of compound XL in ocular applications.

Retinal Edema (Method #1)

Retinal edema was induced in rats by retinal ischemia. LE rats were injected i.v. with the photosensitizing dye Rose Bengal, followed by laser stimulation of a single retinal vein (in the right eye only) so as to induce thrombosis and thus retinal ischemia. Animals were dosed topically with either test compound or vehicle (10 μL eyedrops twice per day bilaterally) for a total of 5 dosings. Retinal edema was then measured by injecting animals i.p. with sodium fluorescein followed 45 later by ocular fluorophotometry to detect fluorescein leakage into the retina and vitreous chamber.

An Edema Index (EI) was calculated according to the following formula: $EI=(F_{od}-F_{os})/F_{os}$, where $F_{od}$=AUC value for fluorescence in the right eye, and $F_{os}$=AUC value for fluorescence in the left (treated but not thrombosed) eye. As can be seen from Table 4, animals treated with a 1% solution of compound XL showed an overall 55% reduction in retinal edema compared to vehicle-treated animals (P=0.008).

TABLE 4

| Treatment | N | Edema Index | SD | % Reduction vs. Vehicle |
|---|---|---|---|---|
| Vehicle | 12 | 5.2 | 3.1 | N/A |
| 1% of compound XL (topical bid × 5) | 12 | 2.3 | 1.6 | −55% (P = 0.008) |

Retinal Edema (Method #2)

Retinal edema was induced in rats by intravitreal injection of vascular endothelial growth factor (VEGF). LE rats were dosed topically (bilaterally) with either test compound or vehicle (10 μL eyedrops), followed by intravitreal injections of either saline (left eye) or VEGF (right eye). Five hours later, animals were again dosed topically with test compound or vehicle, and then injected i.p. with sodium fluorescein followed 45 later by ocular fluorophotometry to detect fluorescein leakage into the retina and vitreous chamber.

EI was calculated according to the following formula: $EI=(F_{od}-F_{os})/F_{os}$, where $F_{od}$=AUC value for fluorescence in the right eye, and $F_{os}$=AUC value for fluorescence in the left (saline injected) eye. As can be seen from Table 5, animals treated with a 1% solution of compound XL showed an overall 70% reduction in retinal edema compared to vehicle-treated animals (P=0.035).

TABLE 5

| Treatment | N | EI | SD | % Reduction vs. Vehicle |
|---|---|---|---|---|
| Vehicle | 11 | 0.363 | 0.208 | n/A |
| 1% of compound XL (topical bid × 5) | 13 | 0.110 | 0.307 | −70% (P = 0.035) |

Retinal Neovascularization

Retinal neovascularization was induced in mouse pups by cyclic exposure to normoxia-hyperoxia-normoxia. C57BL/6 mouse pups were exposed to hyperoxia (75% $O_2$ environment) for 5 days starting at from postnatal day 7, then returned to a normoxic environment. Dosing was also initiated at this time (bilateral topical application of test compound or vehicle as a 10 μL eyedrops twice per day). After 5 days of dosing, retinal wholemounts were prepared and stained with a fluorescently labeled lectin that specifically stains murine endothelium. Digital images were captured by fluorescence microscopy and used to quantify total vascular area. As shown in Table 6, animals treated with a 0.1% solution of compound XL showed an overall 29% reduction in retinal vascularization compared to vehicle-treated animals (P=0.009).

TABLE 6

| Treatment | N | Area (mm$^2$) | SD | % Reduction vs. Vehicle |
|---|---|---|---|---|
| Vehicle | 6 | 8.269 | 0.836 | N/A |
| 1% of compound XL (topical bid × 5) | 6 | 6.429 | 1.634 | −29% (P = 0.0.009) |

Choroidal Neovascularization

Choroidal neovasculariztion was induced in mice by laser injury. Laser photocoagulation was performed on the choroids of C57BL/6 mice, after which mice were dosed topically with test compound or vehicle for a total of 14 days (10 μL applied per eye twice per day). At the end of the 2 week dosing period, mice were perfused with fluorescein-labeled dextran ($2\times10^6$ average molecular weight), eyes were removed and fixed in formalin, and choroidal flatmounts prepared. Laser injury sites were photographed by fluorescence microscopy and digital images were used to quantify the area of choroidal neovascularization. As can be seen from table 7, animals treated with a 1% solution of compound XL showed an overall 42% reduction in choroidal neovascularization compared to vehicle-treated animals, however at the study power used this did not reach the level of statistical significance (P=0.112).

TABLE 7

| Treatment | N | Area (μm²) | SD | % Reduction vs. Vehicle |
|---|---|---|---|---|
| Vehicle | 12 | 16,192 | 12,473 | N/A |
| 1% of compound XL (topical bid × 5) | 12 | 9,388 | 6,408 | −42% (P = 0.112) |

Although the invention has been described with reference to the above examples, it will be understood that modification and variations are encompassed within the spirit and scope of the invention. Accordingly, the invention is limited only by the following claims.

What is claimed is:

1. A compound of structure A:

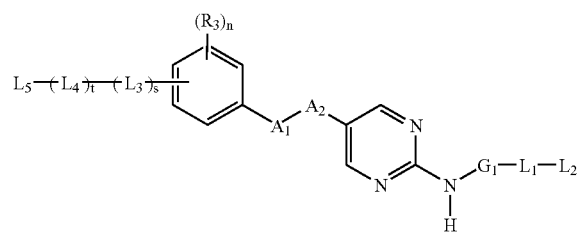

wherein:

$G_1$ is selected from a group consisting of an optionally substituted aryl or an optionally substituted heteroaryl;

the moiety $L_1$-$L_2$ is selected from a group consisting of:

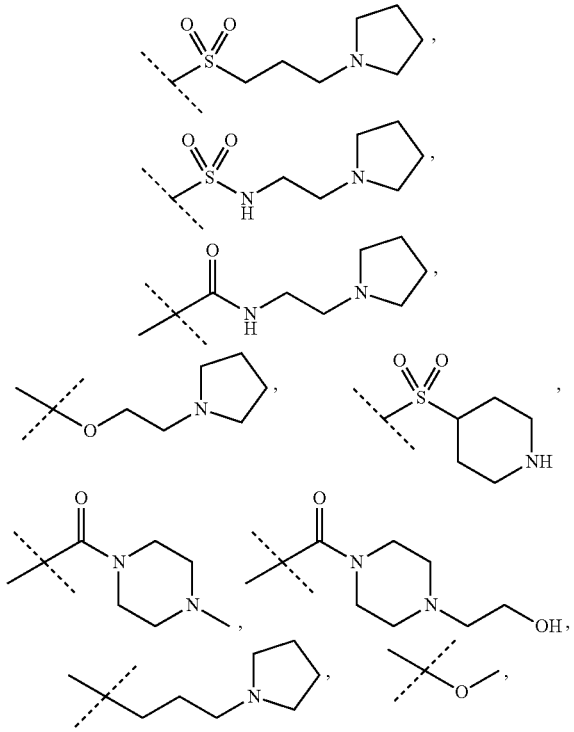

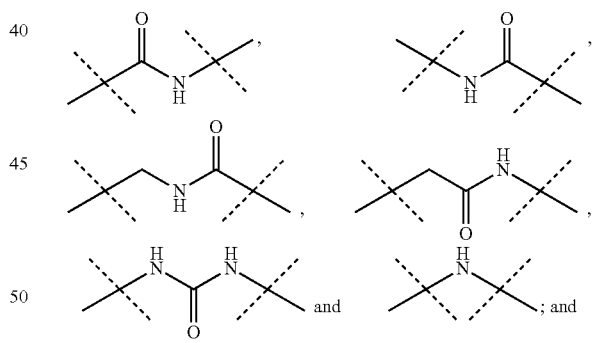

$A_1$ is selected from a group consisting of a bond, $NR_a$, C(O), S(O), S(O)$_2$, P(O)$_2$, O, S, and C(R$_a$)$_2$, wherein if $A_1$ is a bond, then the phenyl ring is directly connected to the group $A_2$;

$A_2$ is selected from a group consisting of NR, C(O), S(O), S(O)$_2$, P(O)$_2$, O, and S; and the connectivity between the phenyl ring, $A_1$, $A_2$ and the pyrimidine ring are chemically correct;

$R_a$ is selected from a group consisting of H, lower alkyl, branched alkyl, hydroxyalkyl, aminoalkyl, thioalkyl, alkylhydroxyl, alklythiol, and alkylamino;

$R_3$ is selected independently for each occurrence from a group consisting of hydrogen, alkyl, branched alkyl, alkoxy, halogen, CF$_3$, cyano, substituted alkyl, hydroxyl, alkylhydroxyl, thiol, alkylthiol, thioalkyl, amino, and aminoalkyl;

n is an integer having value between 0 and 4 inclusive;

the moiety

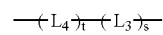

is selected from a group consisting of:

$L_5$ is selected from a group consisting of lower alkyl, branched alkyl, CF$_3$, cycloalkyl, optionally substituted aryl, optionally substituted heteroaryl, bicyclic aryl, bicyclic heteroaryl, bicyclic with one of the rings being aryl or heteroaryl and the other ring being nonaryl, and bicyclic with both rings being nonaryl;

wherein an optionally substituted aryl or heteroaryl, independently for each occurrence, can be substituted on 1, 2, 3, or 4 carbons by alkyl, branched alkyl, alkoxy, halogen, CF$_3$, cyano, substituted alkyl, hydroxyl, alkylhydroxyl, thiol, alkylthiol, thioalkyl, amino, and aminoalkyl;

or a pharmaceutically acceptable salt or stereoisomer thereof.

2. The compound of claim 1 having the structure

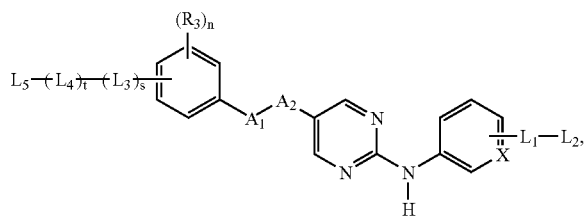

wherein X is selected from a group consisting of CH and N.

3. The compound of claim 1 having the structure

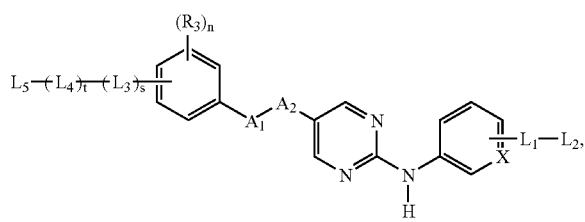

wherein each of $A_1$ and $A_2$ is independently selected from a group consisting of C=O and NH, with the further proviso that when $A_1$ is NH, $A_2$ is C=O, and when $A_2$ is NH, $A_1$ is C=O.

4. The compound of claim 3 having the structure

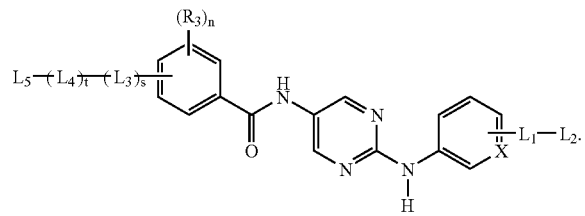

5. The compound of claim 4, wherein $L_5$ is selected from a group consisting of an optionally substituted aryl or an optionally substituted heteroaryl.

6. The compound of claim 3 having the structure

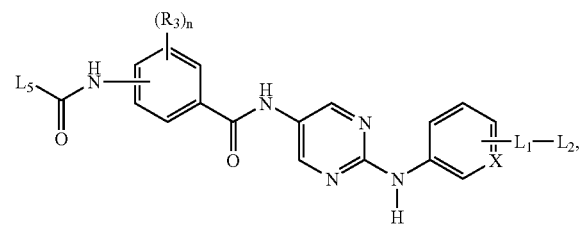

wherein $L_5$ is selected from a group consisting of an optionally substituted aryl or an optionally substituted heteroaryl.

7. The compound of claim 6, wherein $L_5$ is an optionally substituted aryl.

8. A compound having the structure:

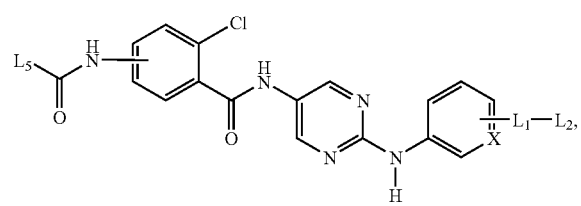

wherein $L_5$ is a phenyl optionally substituted on 1, 2, 3, 4, or 5 carbons with halogen, alkyl, or $CF_3$;

X is N or CH; and the moiety $L_1$-$L_2$ is selected from a group consisting of —$SO_2$-alkyl-heterocycle, —$SO_2$NH-alkyl-heterocycle; $SO_2$-heterocycle, —O-alkyl-heterocycle; —C(O)N-alkyl-heterocycle, —C(O)-alkylheterocycle, -alkyl-heterocycle; —O-alkyl; —C(O)O-alkyl; —OH; —OC(O)-phenyl; wherein the heterocycle or the phenyl can be optionally substituted with alkyl, alkoxy, hydroxyalkyl, or halogen;

or a pharmaceutically acceptable salt or stereoisomer thereof.

9. The compound of claim 8, wherein the optionally substituted heterocycle is selected from a group consisting of azetidine, pyrrolidine, morpholine, piperidine, piperazine, azepane, diazepane, and azocane.

10. A compound having the structure

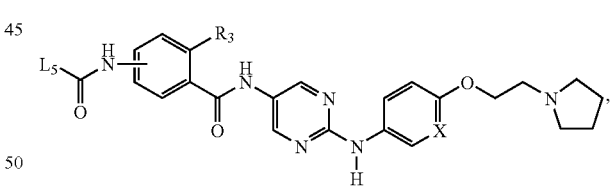

wherein $L_5$ is phenyl, optionally substituted with methyl, halogen, or $CF_3$;

$R_3$ is selected from a group consisting of methyl and chloro, and

X is selected from a group consisting of CH and N; or a pharmaceutically acceptable salt, or stereoisomer thereof.

11. The compound of claim 1, wherein the compound is selected from the group consisting of compounds X, XLV, XL, XXXVIII, and XXXIX, or a pharmaceutically acceptable salt thereof:

X
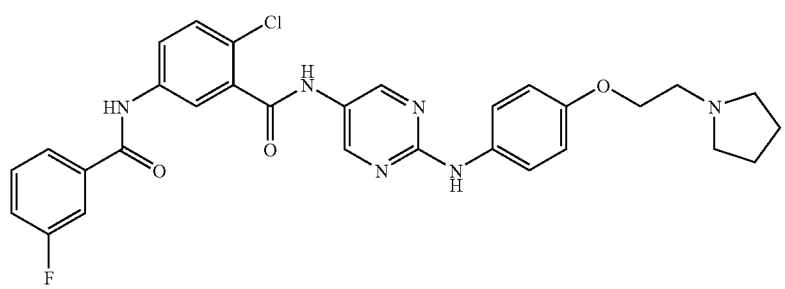
XLV
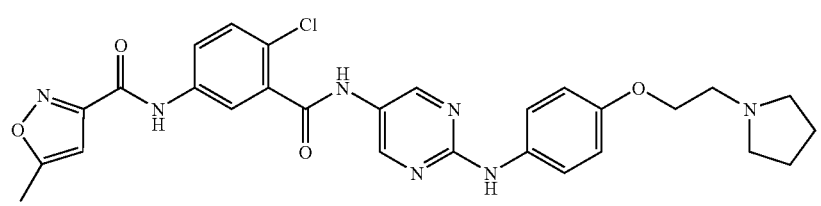
XL
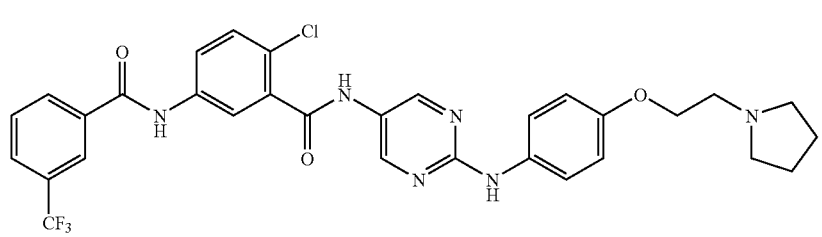
XXXVIII
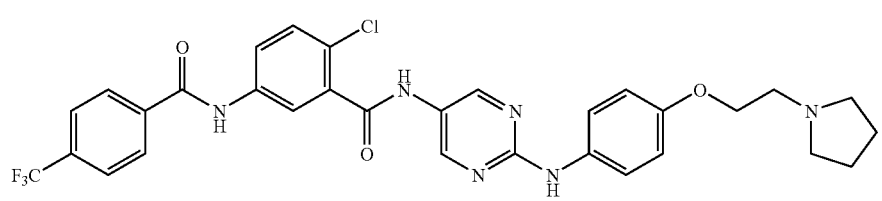
XXXIX
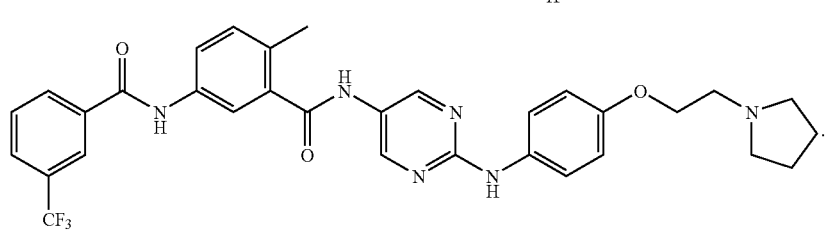
12. The compound of claim 1, wherein the compound is selected from the group consisting of compounds XXVIII and XLIV, or a pharmaceutically acceptable salt thereof:
XXVIII
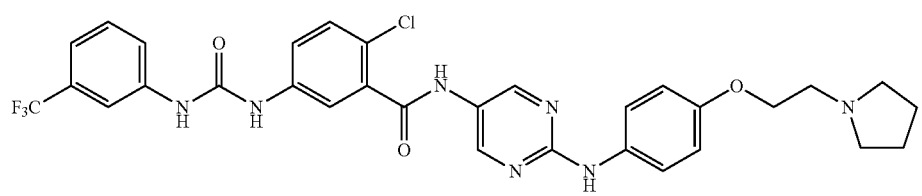
XLIV
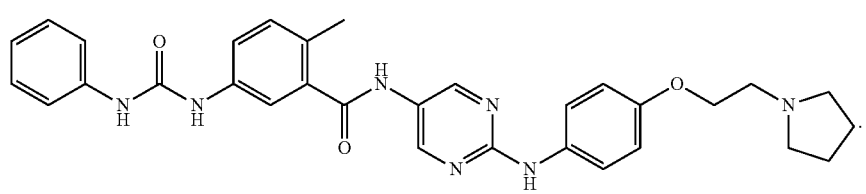

13. The compound of claim 1, wherein the compound is selected from the group consisting of compounds XLIII and XXXIV, or a pharmaceutically acceptable salt thereof:
XLIII
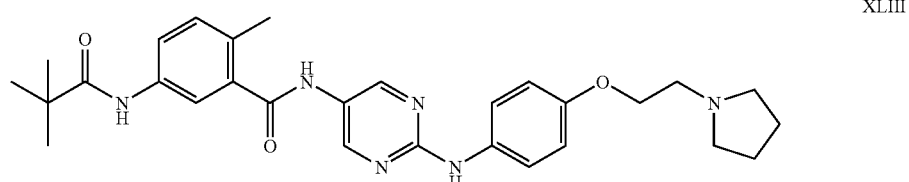
XXXIV
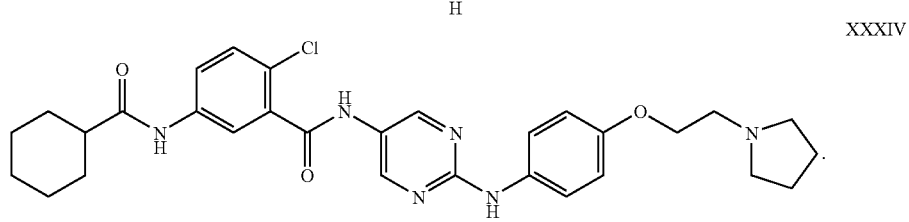
14. The compound of claim 1, wherein the compound is selected from the group consisting of compounds XVI, XVII, XX, and XXII, or a pharmaceutically acceptable salt thereof:
XVI
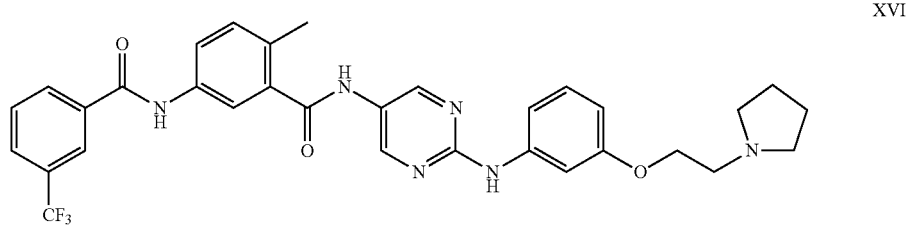
XVII
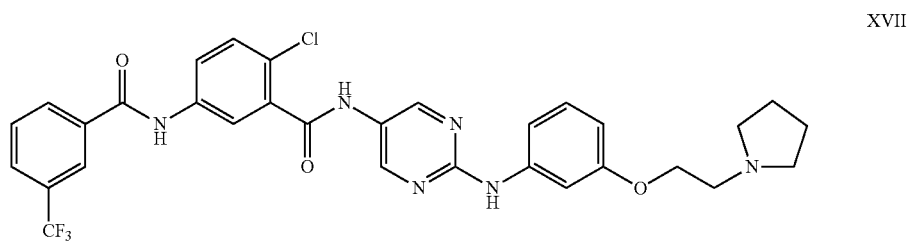
XX
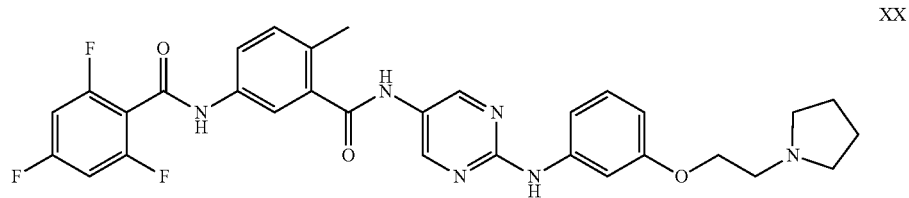
XXII
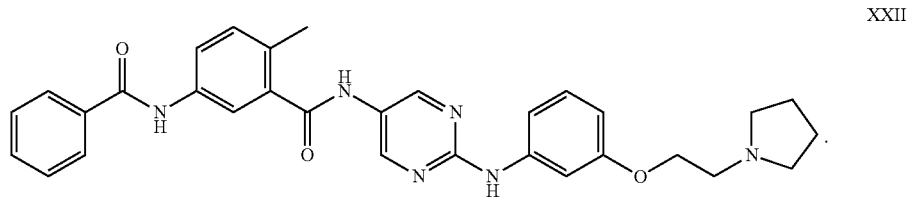

15. The compound of claim 1, wherein the compound is compound XXIII, or a pharmaceutically acceptable salt thereof:

XXIII

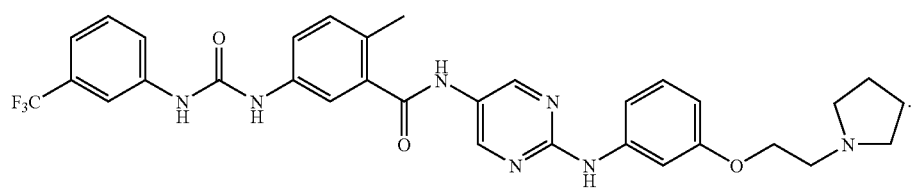

16. The compound of claim 1, wherein the compound is selected from the group consisting of compounds XVIII and XIX, or a pharmaceutically acceptable salt thereof:

XVIII

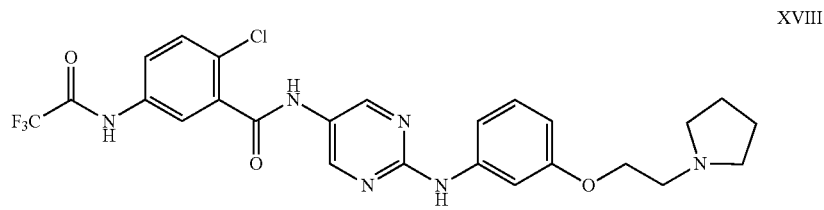

XIX

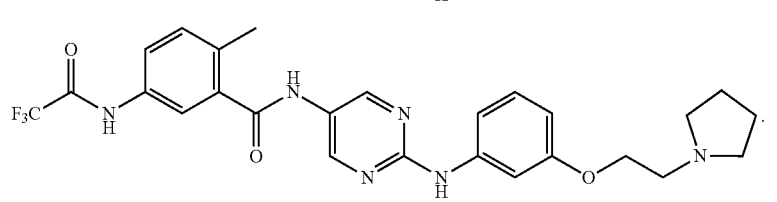

17. The compound of claim 1, wherein the compound is compound XXI, or a pharmaceutically acceptable salt thereof:

XXI

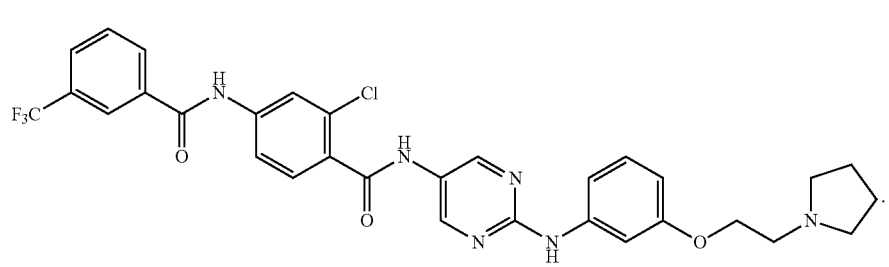

18. The compound of claim 1, wherein the compound is selected from the group consisting of compounds XXX and XXXI, or a pharmaceutically acceptable salt thereof:

XXX

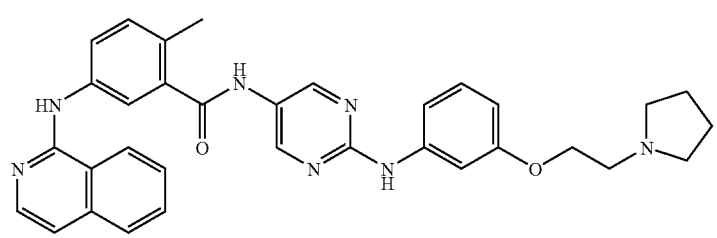

-continued
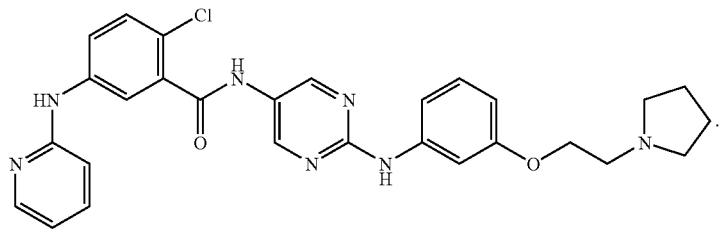
XXXI
19. The compound of claim 1, wherein the compound is selected from the group consisting of compounds I, II, III, and IV, or a pharmaceutically acceptable salt thereof:
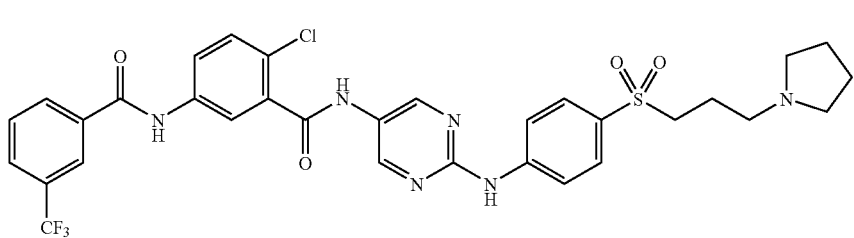
I
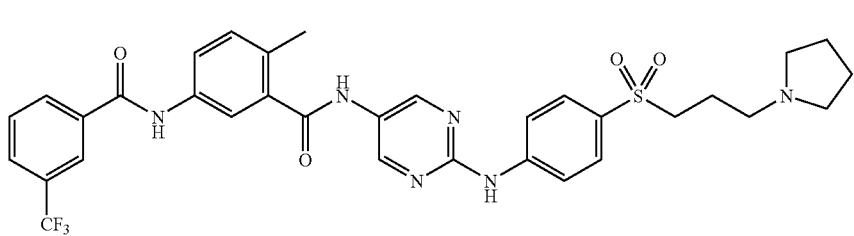
II
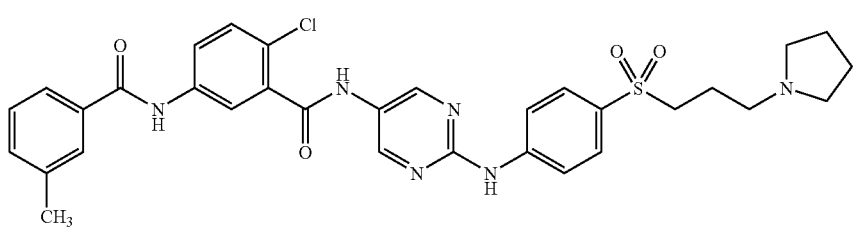
III
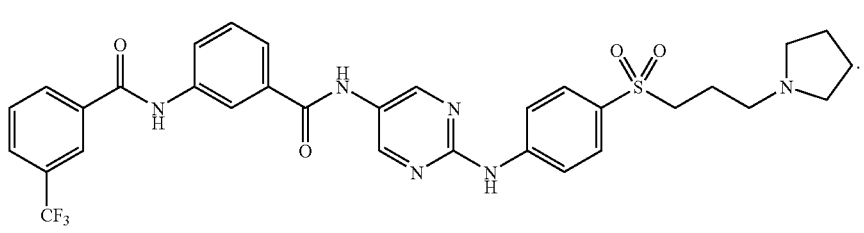
IV 20. The compound of claim 1, wherein the compound is selected from the group consisting of compounds VII, XI, XII, XIII, XIV, and XV, or a pharmaceutically acceptable salt thereof:
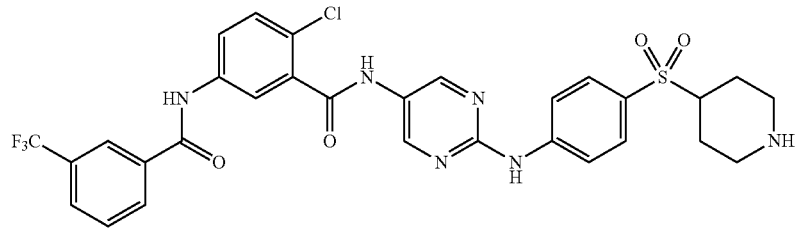
VII
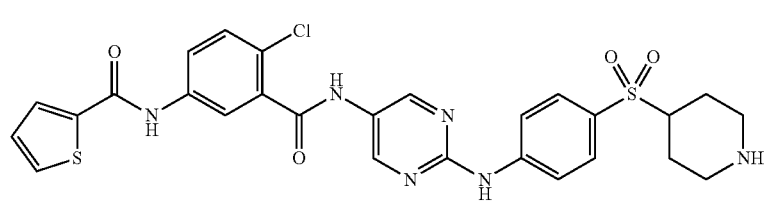
XI
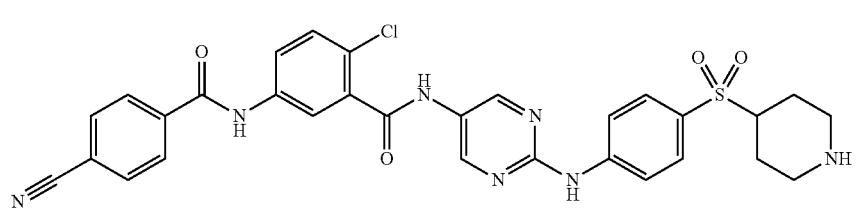
XII
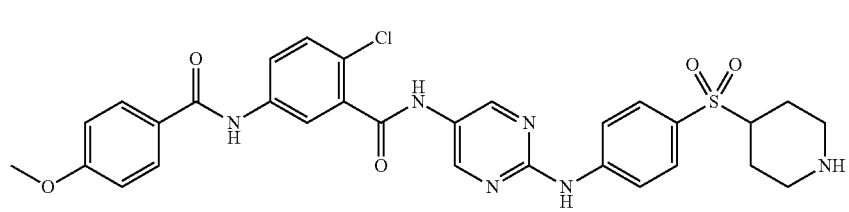
XIII
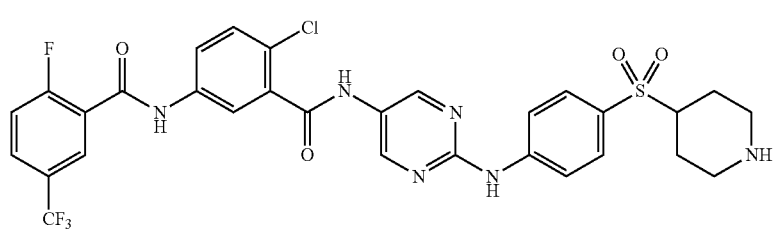
XIV
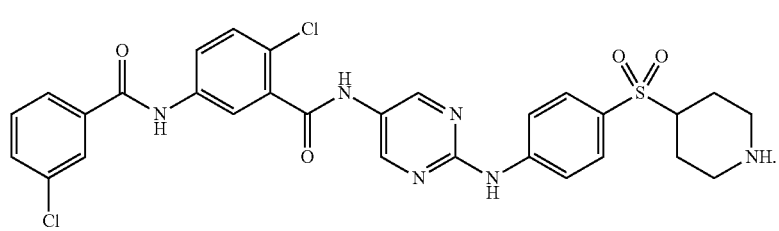
XV

21. The compound of claim 1, wherein the compound is compound LII, or a pharmaceutically acceptable salt thereof:

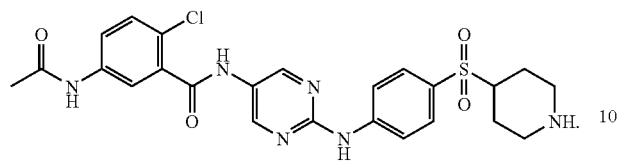

LII

22. The compound of claim 1, wherein the compound is compound XXIX, or a pharmaceutically acceptable salt thereof:

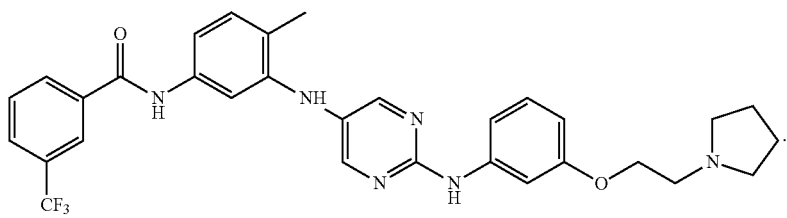

XXIX

23. The compound of claim 1, wherein the compound is selected from the group consisting of compounds VIII and IX, or a pharmaceutically acceptable salt thereof:

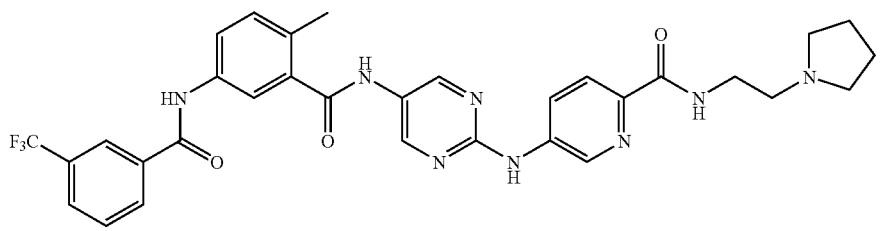

VIII

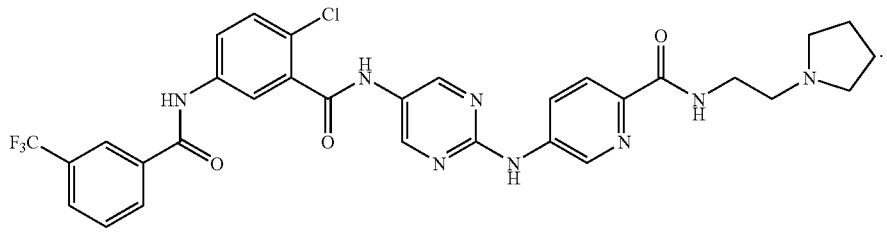

IX

24. The compound of claim 1, wherein the compound is compound XLVII, or a pharmaceutically acceptable salt thereof:

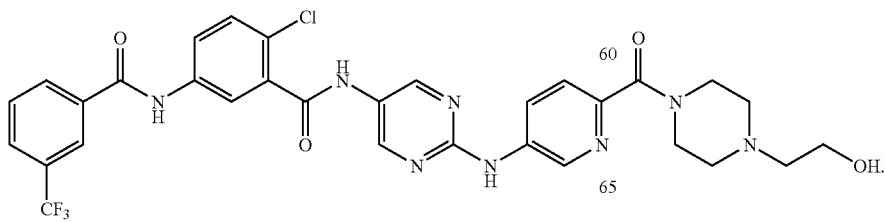

XLVII

25. The compound of claim 1, wherein the compound is compound V, or a pharmaceutically acceptable salt thereof:

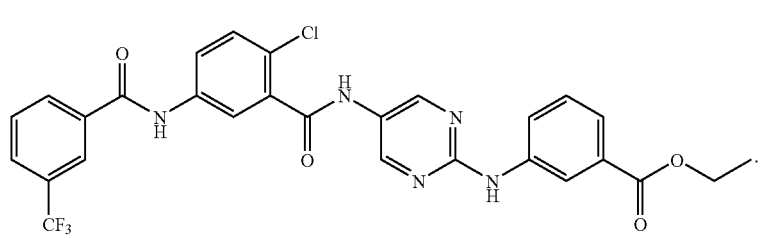

26. The compound of claim 1, wherein the compound is compound XLVI, or a pharmaceutically acceptable salt thereof:

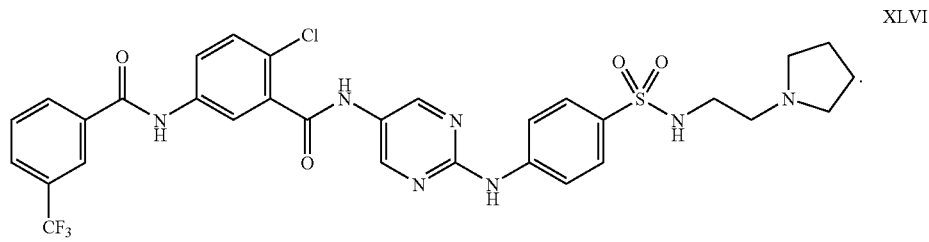

27. The compound of claim 1, wherein the compound is selected from the group consisting of compounds XLI and XLII, or a pharmaceutically acceptable salt thereof:

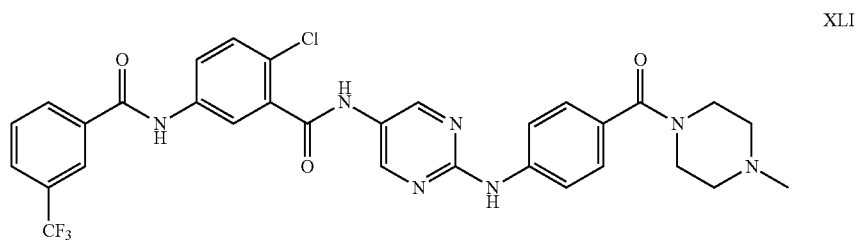

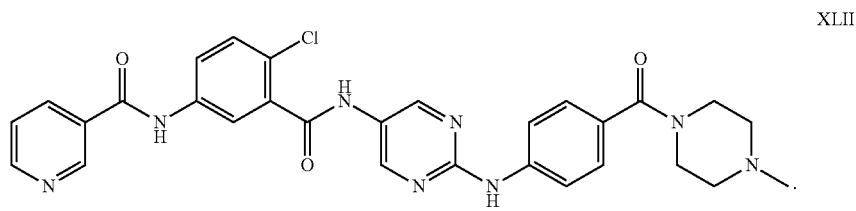

28. The compound of claim 1, wherein the compound is compound XXXVII, or a pharmaceutically acceptable salt thereof:

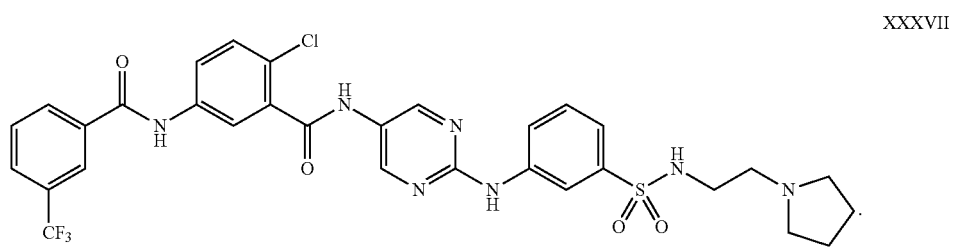

29. The compound of claim 1, wherein the compound is selected from the group consisting of compounds XXXII and XXIII, or a pharmaceutically acceptable salt thereof:

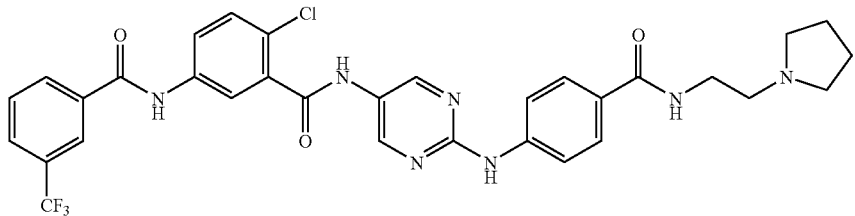

XXXII

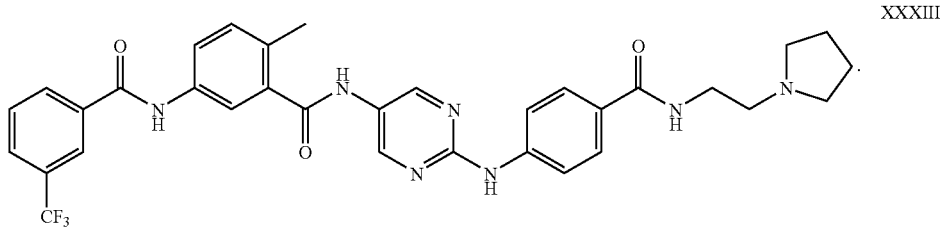

XXXIII

30. The compound of claim 1, wherein the compound is compound XL, or a pharmaceutically acceptable salt thereof:

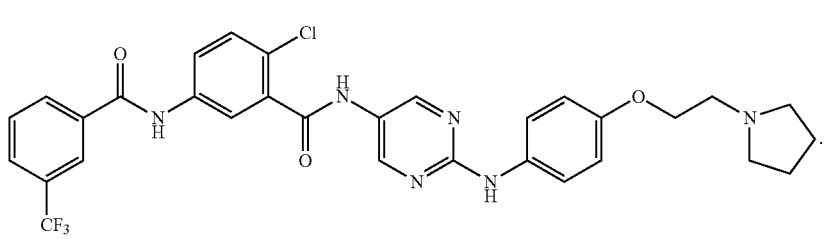

XL

31. The compound of claim 1, wherein the compound is selected from the group consisting of compounds LVI, LVII, and LX-LXIII, or a pharmaceutically acceptable salt thereof:

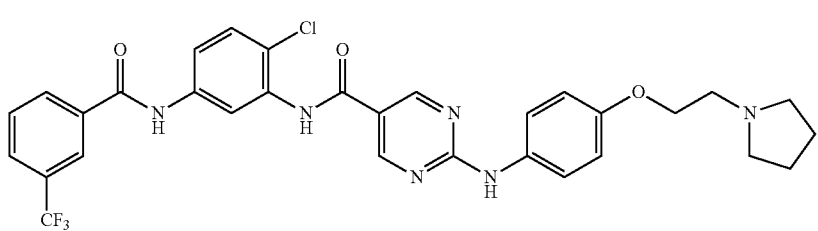

LVI

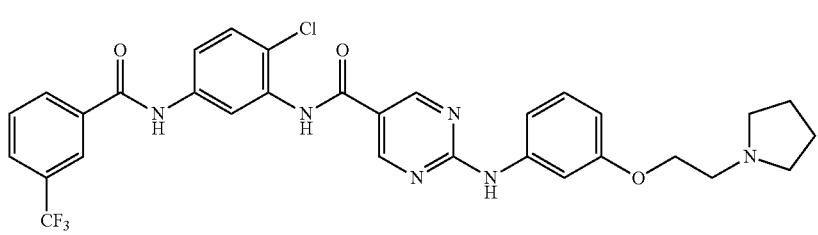

LVII

-continued

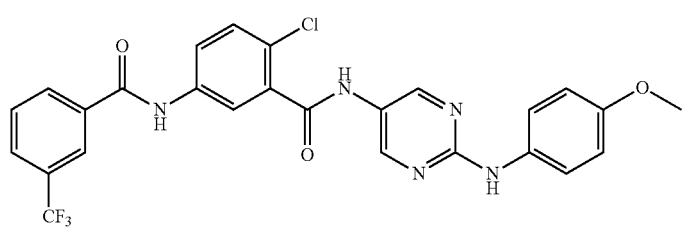

LX

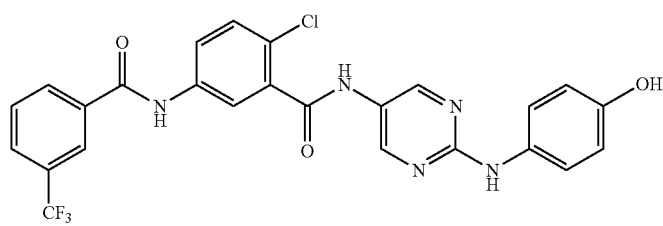

LXI

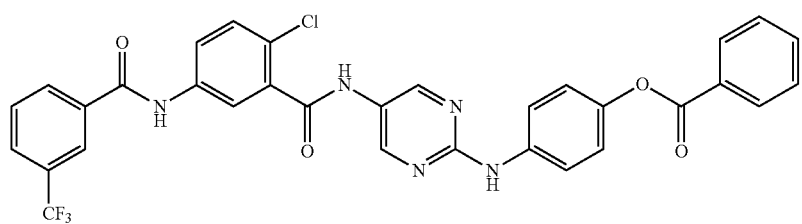

LXII

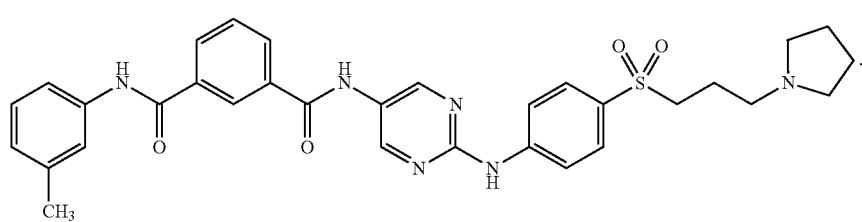

LXIII

32. A pharmaceutical composition comprising at least one compound represented by structure A according to claim 1 and a pharmaceutically acceptable carrier.

33. The pharmaceutical composition of claim 32, wherein said composition is suitable for oral administration, intravenous administration, topical administration, ocular administration or subcutaneous administration.

34. The pharmaceutical composition of claim 32, wherein said composition is suitable for ocular administration.

* * * * *

UNITED STATES PATENT AND TRADEMARK OFFICE
CERTIFICATE OF CORRECTION

| | | |
|---|---|---|
| PATENT NO. | : 8,030,487 B2 | Page 1 of 1 |
| APPLICATION NO. | : 11/772572 | |
| DATED | : October 4, 2011 | |
| INVENTOR(S) | : Noronha et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,010 days.

Signed and Sealed this
Sixth Day of March, 2012

David J. Kappos
*Director of the United States Patent and Trademark Office*